(12) United States Patent
Tanabe et al.

(10) Patent No.: US 11,959,058 B2
(45) Date of Patent: Apr. 16, 2024

(54) CELL PROCESSING SYSTEM AND CELL PROCESSING DEVICE

(71) Applicants: I Peace, Inc., Palo Alto, CA (US); Koji Tanabe, Palo Alto, CA (US)

(72) Inventors: Koji Tanabe, Palo Alto, CA (US); Ryoji Hiraide, Kyoto (JP)

(73) Assignee: I Peace, Inc., Palo Alto, CA (US)

( * ) Notice: Subject to any disclaimer, the term of this patent is extended or adjusted under 35 U.S.C. 154(b) by 17 days.

(21) Appl. No.: 17/815,022

(22) Filed: Jul. 26, 2022

(65) Prior Publication Data

US 2022/0356430 A1 Nov. 10, 2022

Related U.S. Application Data

(63) Continuation of application No. 16/485,409, filed as application No. PCT/JP2017/007577 on Feb. 27, 2017, now abandoned.

(51) Int. Cl.
| | | |
|---|---|---|
| *C12M 1/00* | (2006.01) | |
| *C12M 1/12* | (2006.01) | |
| *C12M 1/26* | (2006.01) | |

(52) U.S. Cl.
CPC ............ *C12M 23/34* (2013.01); *C12M 25/00* (2013.01); *C12M 29/04* (2013.01); *C12M 33/14* (2013.01)

(58) Field of Classification Search
CPC ...... C12M 23/34; C12M 25/00; C12M 29/04; C12M 33/14; C12M 41/12; C12M 41/34; C12N 15/09
See application file for complete search history.

(56) References Cited

U.S. PATENT DOCUMENTS

| | | |
|---|---|---|
| 4,999,298 A | 3/1991 | Wolfe et al. |
| 8,820,538 B1 | 9/2014 | Lin |
| 2006/0194193 A1 | 8/2006 | Tsuruta et al. |
| 2008/0032380 A1 | 2/2008 | Kleis et al. |
| 2009/0111179 A1 | 4/2009 | Hata et al. |
| 2010/0173394 A1 | 7/2010 | Colston, Jr. et al. |
| 2011/0212513 A1 | 9/2011 | Yokoi et al. |
| 2011/0250690 A1 | 10/2011 | Craig |
| 2012/0035742 A1 | 2/2012 | Vunjak-Novakovic et al. |
| 2012/0258487 A1 | 10/2012 | Chang et al. |
| 2013/0092630 A1 | 4/2013 | Wegener |
| 2013/0345094 A1 | 12/2013 | Noggle et al. |

(Continued)

FOREIGN PATENT DOCUMENTS

| | | |
|---|---|---|
| CN | 101300339 A | 11/2008 |
| EP | 2665807 A1 | 11/2013 |

(Continued)

*Primary Examiner* — Liban M Hassan
(74) *Attorney, Agent, or Firm* — Studebaker & Brackett PC

(57) ABSTRACT

A cell processing system comprising an enclosure 601, an outer enclosure 701 that envelops the enclosure 601, an intake air purification filter 602 provided in the enclosure 601, that purifies gas that has been drawn in from outside the enclosure 601, a circulating apparatus, inside the outer enclosure 701, that circulates gas inside and outside the enclosure 601 in such a manner that gas in the outer enclosure 701 is drawn into the enclosure 601 through the intake air purification filter 602 and gas inside the enclosure 601 is discharged into the outer enclosure 701, and a cell processing apparatus for processing of cells, disposed inside the enclosure 601.

4 Claims, 64 Drawing Sheets

(56) References Cited

U.S. PATENT DOCUMENTS

| | | | |
|---|---|---|---|
| 2015/0113927 A1 | 4/2015 | Wright et al. | |
| 2016/0017271 A1 | 1/2016 | Nozaki et al. | |
| 2018/0245041 A1* | 8/2018 | Tanabe | C12M 41/12 |

FOREIGN PATENT DOCUMENTS

| | | | |
|---|---|---|---|
| EP | 2812426 | A1 | 12/2014 |
| JP | S63-001415 | A | 1/1988 |
| JP | H01-285185 | A | 11/1989 |
| JP | H06-004125 | A | 1/1994 |
| JP | 2006-014693 | A | 1/2006 |
| JP | 4183742 | B1 | 11/2008 |
| JP | 2009-226047 | A | 10/2009 |
| JP | 2009-226048 | A | 10/2009 |
| JP | 2010-161931 | A | 7/2010 |
| JP | 2011-177091 | A | 9/2011 |
| JP | 2014-509854 | A | 4/2014 |
| JP | 2014-114997 | A | 6/2014 |
| JP | 2015-502747 | A | 1/2015 |
| JP | 2015-526269 | A | 9/2015 |
| JP | 2016-198035 | A | 12/2016 |
| WO | 2010/102059 | A1 | 9/2010 |
| WO | 2015/131087 | A1 | 9/2015 |
| WO | 2015/142378 | A1 | 9/2015 |
| WO | 2016/133209 | A1 | 8/2016 |
| WO | 2016/203598 | A1 | 12/2016 |
| WO | 2017/038837 | A1 | 3/2017 |
| WO | 2017/038887 | A1 | 3/2017 |

* cited by examiner (a) Suspension culture in gelled medium (b) Suspension culture in non-gelled medium (a) Colonies before reseeding onto feeder cells (b) Colonies 3 days after reseeding onto feeder cells (a) Dialysis tube, medium exchange (b) Dialysis tube, no medium exchange (c) No dialysis tube, no medium exchange ial Application No.
CELL PROCESSING SYSTEM AND CELL PROCESSING DEVICE

CROSS-REFERENCE TO RELATED APPLICATIONS

This application is a Continuation of U.S. patent application Ser. No. 16/485,409, filed on Aug. 12, 2019, which is the U.S. National Phase of International Application No. PCT/JP2017/007577, filed on Feb. 27, 2017, the entire contents of which are incorporated herein by reference.

FIELD

The present invention relates to cell technology, and specifically it relates to a cell processing system and a cell processing apparatus.

BACKGROUND

Embryonic stem cells (ES cells) are stem cells established from early embryos of human or mice. ES cells are pluripotent, being capable of differentiating into all cells in the body. At the current time, human ES cells are able to be used in cell transplantation therapy for numerous diseases including Parkinson's disease, juvenile onset diabetes and leukemia. However, certain barriers exist against transplantation of ES cells. In particular, transplantation of ES cells can provoke immunorejection similar to the rejection encountered after unsuccessful organ transplantation. Moreover, there are many ethical considerations as well as critical and dissenting opinions against the use of ES cell lines that have been established by destruction of human embryos.

It was against this background that Professor Shinya Yamanaka of Kyoto University successfully established a line of induced pluripotent stem cells (iPS cells) by transferring four genes: Oct3/4, Klf4, c-Myc and Sox2, into somatic cells. For this, Professor Yamanaka received the Nobel Prize in Physiology or Medicine in 2012 (see PTLs 1 and 2, for example). iPS cells are ideal pluripotent cells which are free of issues of rejection or ethical problems. Therefore, iPS cells are considered promising for use in cell transplantation therapy.

CITATION LIST

Patent Literature

PTL 1: Japanese Patent Publication No. 4183742
PTL 2: Japanese Unexamined Patent Publication No. 2014-114997

SUMMARY

Technical Problem

Induced stem cells such as iPS cells are established by introducing inducing factors such as genes into cells which are then subjected to amplifying culturing and cryopreservation. Stem cells have conventionally been produced manually by technicians in a cleanroom. Blood and inducing factors used for production of stem cells must be prevented from coming into contact with humans. Furthermore, because cells can potentially be infected with viruses and other pathogens, it is essential to keep the cells contained to prevent them from being released to the exterior. For example, when cells infected with hepatitis virus or human immunodeficiency virus (HIV) diffuse out they can have fatal effects on humans and animals. It is therefore necessary to prevent release of blood, inducing factors, preinduction cells and induced cells out of cleanrooms. In addition, iPS cells from only a single individual are prepared in the same cleanroom over a given period of time in order to prevent cross-contamination with iPS cells of other individuals.

It is therefore an object of the present invention to provide a cell processing system and a cell processing apparatus that allow treatment of cells without contamination of the surroundings.

Solution to Problem

According to one aspect of the invention there is provided a cell processing system comprising an enclosure, an outer enclosure that envelops the enclosure, an intake air purification filter provided in the enclosure, that purifies gas that has been drawn in from outside the enclosure, a circulating apparatus, inside the outer enclosure, that circulates gas inside and outside the enclosure in such a manner that gas in the outer enclosure is drawn into the enclosure through the intake air purification filter and gas inside the enclosure is discharged into the outer enclosure, and a cell processing apparatus for processing of cells, disposed inside the enclosure.

In this cell processing system, a pressure adjustment hole may be provided in the outer enclosure.

In this cell processing system, the circulating apparatus may comprise a gas discharger, provided in the enclosure, that draws in gas from the enclosure and discharges purified gas out of the enclosure.

In this cell processing system, the gas discharger may comprise an exhaust system that exhausts gas inside the enclosure to the exterior of the enclosure, and an exhaust purification filter that purifies gas that has been drawn in by the exhaust system.

In this cell processing system, the exhaust purification filter may be situated upstream from the exhaust system.

This cell processing system may further comprise a shielding member that can be attached to the exhaust purification filter so as to shield the exhaust purification filter.

In this cell processing system, the shielding member may comprise an enclosure side shielding member that can be attached to the exhaust purification filter so as to shield the exhaust purification filter from the enclosure interior, and an exhaust system side shielding member that can be attached to the exhaust purification filter so as to shield the exhaust purification filter from the exhaust system.

This cell processing system may further comprise a sterilizing device that sterilizes the exhaust purification filter.

This cell processing system may still further comprise a second exhaust purification filter disposed downstream from the exhaust system.

This cell processing system may still further comprise a shielding member that can be attached to the second exhaust purification filter so as to shield the second exhaust purification filter.

In this cell processing system, the shielding member may further comprise an exhaust system side shielding member that can be attached to the second exhaust purification filter, so as to shield the second exhaust purification filter from the exhaust system.

This cell processing system may further comprise a sterilizing device that sterilizes the second exhaust purification filter.

In this cell processing system, the circulating apparatus may comprise an injector, provided in the enclosure, that draws in gas that has been purified by the intake air purification filter, from out of the enclosure.

In this cell processing system, the intake air purification filter may be situated downstream from the injector.

This cell processing system may further comprise a shielding member that can be attached to the intake air purification filter so as to shield the intake air purification filter.

In this cell processing system, the shielding member may comprise an enclosure side shielding member that can be attached to the intake air purification filter so as to shield the intake air purification filter from the enclosure interior, and an injector side shielding member that can be attached to the intake air purification filter so as to shield the intake air purification filter from the injector.

This cell processing system may further comprise a sterilizing device that sterilizes the intake air purification filter.

In this cell processing system, the enclosure interior may be at negative pressure compared to the enclosure exterior.

Stem cells may be cultured in the cell processing apparatus of this cell processing system.

This cell processing system may still further comprise a sterilizing device that sterilizes the space in which the cell processing apparatus is disposed inside the enclosure.

This cell processing system may still further comprise a temperature regulating device that regulates the temperature in the space in which the cell processing apparatus is disposed inside the enclosure.

This cell processing system may still further comprise a carbon dioxide concentration control device that controls the carbon dioxide concentration of the space in which the cell processing apparatus is disposed inside the enclosure.

In this cell processing system, the enclosure interior may be demarcated into multiple zones.

The cell processing apparatus of this cell processing system may also comprise a preintroduction cell solution-feeding channel through which a cell-containing solution passes, a factor introducing device that is connected to the preintroduction cell solution-feeding channel and introduces a pluripotency inducing factor into cells to prepare inducing factor-introduced cells, and a cell mass preparation device in which the inducing factor-introduced cells are cultured to prepare a plurality of cell masses comprising stem cells.

This cell processing system may still further comprise an enclosure, an intake air purification filter provided in the enclosure, that purifies gas that has been drawn in from outside the enclosure, a returning member to return gas discharged from the enclosure back to the intake air purification filter, a circulating apparatus that circulates gas between the enclosure and the returning member, in such a manner that the gas inside the enclosure is discharged into the returning member and the gas in the returning member is drawn into the enclosure through the intake air purification filter, and a cell processing apparatus for processing of cells, disposed inside the enclosure.

The returning member in this cell processing system may have a shape that engages with the enclosure.

In this cell processing system, the returning member may comprise a base with a hollow interior, in contact with the bottom of the enclosure, a first cover that allows communication between a first opening provided in the base and a ventilation unit provided on the first end face of the enclosure, and a second cover that allows communication between a second opening provided in the base and a ventilation unit provided on a second end face of the enclosure.

The returning member in this cell processing system may be a duct.

In this cell processing system, the circulating apparatus may comprise a gas discharger, provided in the enclosure, that draws in gas from the enclosure and discharges purified gas into the returning member.

In this cell processing system, the gas discharger may comprise an exhaust system that exhausts gas inside the enclosure into the returning member, and an exhaust purification filter that purifies gas that has been drawn in by the exhaust system.

In this cell processing system, the exhaust purification filter may be situated upstream from the exhaust system.

This cell processing system may further comprise a shielding member that can be attached to the exhaust purification filter so as to shield the exhaust purification filter.

In this cell processing system, the shielding member may comprise an enclosure side shielding member that can be attached to the exhaust purification filter so as to shield the exhaust purification filter from the enclosure interior, and an exhaust system side shielding member that can be attached to the exhaust purification filter so as to shield the exhaust purification filter from the exhaust system.

This cell processing system may further comprise a sterilizing device that sterilizes the exhaust purification filter.

This cell processing system may still further comprise a second exhaust purification filter disposed downstream from the exhaust system.

This cell processing system may still further comprise a shielding member that can be attached to the second exhaust purification filter so as to shield the second exhaust purification filter.

In this cell processing system, the shielding member may further comprise an exhaust system side shielding member that can be attached to the second exhaust purification filter, so as to shield the second exhaust purification filter from the exhaust system.

This cell processing system may further comprise a sterilizing device that sterilizes the second exhaust purification filter.

In this cell processing system, the circulating apparatus may comprise an injector, provided in the enclosure, that draws in gas that has been purified by the intake air purification filter, from inside the returning member.

In this cell processing system, the intake air purification filter may be situated downstream from the injector.

This cell processing system may further comprise a shielding member that can be attached to the intake air purification filter so as to shield the intake air purification filter.

In this cell processing system, the shielding member may comprise an enclosure side shielding member that can be attached to the intake air purification filter so as to shield the intake air purification filter from the enclosure interior, and an injector side shielding member that can be attached to the intake air purification filter so as to shield the intake air purification filter from the injector.

This cell processing system may further comprise a sterilizing device that sterilizes the intake air purification filter.

In this cell processing system, the enclosure interior may be at negative pressure compared to the returning member interior.

Stem cells may be cultured in the cell processing apparatus of this cell processing system.

This cell processing system may still further comprise a sterilizing device that sterilizes the space in which the cell processing apparatus is disposed inside the enclosure.

This cell processing system may still further comprise a temperature regulating device that regulates the temperature in the space in which the cell processing apparatus is disposed inside the enclosure.

This cell processing system may still further comprise a carbon dioxide concentration control device that controls the carbon dioxide concentration of the space in which the cell processing apparatus is disposed inside the enclosure.

In this cell processing system, the enclosure interior may be demarcated into multiple zones.

The cell processing apparatus of this cell processing system may also comprise a preintroduction cell solution-feeding channel through which a cell-containing solution passes, a factor introducing device that is connected to the preintroduction cell solution-feeding channel and introduces a pluripotency inducing factor into cells to prepare inducing factor-introduced cells, and a cell mass preparation device in which the inducing factor-introduced cells are cultured to prepare a plurality of cell masses comprising stem cells.

According to one aspect of the invention there is additionally provided a cell processing apparatus comprising a cell processing instrument that processes cells, an embedding member that embeds the cell processing instrument, and a communicating solution-feeding channel that allows communication between the outside of the embedding member and the cell processing instrument inside the embedding member.

The embedding member in the cell processing apparatus may be made of glass or a resin.

The embedding member in the cell processing apparatus may also be made of a metal.

The cell processing apparatus may further comprise a driving unit disposed outside the embedding member, for feeding of a solution in the communicating solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the communicating solution-feeding channel.

The cell processing instrument in the cell processing apparatus may also comprise a mononuclear cell separating unit disposed inside the embedding member, that separates mononuclear cells from blood.

The cell processing apparatus may further comprise a blood storing unit, disposed outside the embedding member, that stores either or both blood and blood cells, and the communicating solution-feeding channel may also comprise a blood delivery channel that allows communication between the blood storing unit and the mononuclear cell separating unit.

The cell processing apparatus may still further comprise a separating agent storing unit, disposed outside the embedding member, that stores a separating agent for separation of mononuclear cells, and the communicating solution-feeding channel may further comprise a separating agent solution-feeding channel that allows communication between the separating agent storing unit and the mononuclear cell separating unit.

The cell processing instrument in the cell processing apparatus may also comprise a filter disposed inside the embedding member, that isolates cells.

The cell processing instrument in the cell processing apparatus may also comprise a mononuclear cell purifying filter disposed inside the embedding member.

The cell processing instrument in the cell processing apparatus may also comprise a mononuclear cell separating unit, disposed inside the embedding member, that separates mononuclear cells from blood, a mononuclear cell purifying filter disposed inside the embedding member, and a mononuclear cell solution-feeding channel disposed inside the embedding member, that allows communication between the mononuclear cell separating unit and the mononuclear cell purifying filter.

The cell processing apparatus may further comprise a driving unit disposed outside the embedding member, for feeding of a solution in the mononuclear cell solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the mononuclear cell solution-feeding channel.

The cell processing instrument in the cell processing apparatus may also comprise a factor introducing device, disposed inside the embedding member, that introduces a pluripotency inducing factor into cells to create inducing factor-introduced cells.

The cell processing apparatus may still further comprise a factor storing unit, disposed outside the embedding member, that stores the pluripotency inducing factor, and the communicating solution-feeding channel may comprise a factor solution-feeding channel that allows communication between the factor storing unit and the factor introducing device.

In the cell processing apparatus, the pluripotency inducing factor may be introduced into the cells by RNA lipofection at the factor introducing device.

The pluripotency inducing factor in the cell processing apparatus may be DNA, RNA or protein.

The pluripotency inducing factor in the cell processing apparatus may be incorporated into a vector.

The vector in the cell processing apparatus may be Sendai virus vector.

The cell processing instrument in the cell processing apparatus may further comprise a mononuclear cell separating unit, disposed inside the embedding member, that separates mononuclear cells from blood, a factor introducing device, disposed inside the embedding member, that introduces a pluripotency inducing factor into cells to create inducing factor-introduced cells, and a preintroduction cell solution-feeding channel, disposed inside the embedding member, that allows communication between the mononuclear cell separating unit and the factor introducing device.

The cell processing apparatus may further comprise a driving unit disposed outside the embedding member, for feeding of a solution in the preintroduction cell solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the preintroduction cell solution-feeding channel.

The cell processing instrument in the cell processing apparatus may further comprise a mononuclear cell purifying filter, disposed inside the embedding member, a factor introducing device, disposed inside the embedding member, that introduces a pluripotency inducing factor into cells to create inducing factor-introduced cells, and a preintroduction cell solution-feeding channel, disposed inside the embedding member, that allows communication between the mononuclear cell purifying filter and the factor introducing device.

The cell processing apparatus may further comprise a driving unit disposed outside the embedding member, for feeding of a solution in the preintroduction cell solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the preintroduction cell solution-feeding channel.

The cell processing instrument in the cell processing apparatus may also comprise an initializing culturing vessel, disposed inside the embedding member, that cultures the inducing factor-introduced cells into which the pluripotency inducing factor has been introduced.

The cell processing apparatus may still further comprise a blood cell culture medium storing unit, disposed outside the embedding member, that stores blood cell culture medium, and the communicating solution-feeding channel may also comprise a culture medium solution-feeding channel that allows communication between the blood cell culture medium storing unit and the initializing culturing vessel.

The blood cell culture medium in the cell processing apparatus may be continuously supplied to the initializing culturing vessel.

The blood cell culture medium in the cell processing apparatus may also be supplied to the initializing culturing vessel at a prescribed timing.

The cell processing apparatus may still further comprise a cold storage unit, disposed outside the embedding member, that keeps the blood cell culture medium in cold storage.

The cell processing apparatus may still further comprise a stem cell culture medium storing unit, disposed outside the embedding member, that stores stem cell culture medium, and the communicating solution-feeding channel may also comprise a culture medium solution-feeding channel that allows communication between the stem cell culture medium storing unit and the initializing culturing vessel.

The stem cell culture medium in the cell processing apparatus may be continuously supplied to the initializing culturing vessel.

The stem cell culture medium in the cell processing apparatus may also be supplied to the initializing culturing vessel at a prescribed timing.

The cell processing apparatus may still further comprise a cold storage unit, disposed outside the embedding member, that keeps the stem cell culture medium in cold storage.

The cell processing apparatus may still further comprise a waste liquid storage section, disposed outside the embedding member, that stores waste liquid, and the communicating solution-feeding channel may also comprise a waste liquid solution-feeding channel that allows communication between the initializing culturing vessel and the waste liquid storage section.

The initializing culturing vessel in the cell processing apparatus may also comprise a suspension culture vessel that comprises a dialysis tube in which the inducing factor-introduced cells and culture medium are to be accommodated, and a vessel in which the dialysis tube is to be placed, with the culture medium accommodable around the periphery of the dialysis tube.

The cell processing instrument in the cell processing apparatus may further comprise a factor introducing device, disposed inside the embedding member, that introduces a pluripotency inducing factor into cells to create inducing factor-introduced cells, an initializing culturing vessel, disposed inside the embedding member, that cultures the inducing factor-introduced cells, and an introduced cell solution-feeding channel, disposed inside the embedding member, that allows communication between the factor introducing device and the initializing culturing vessel.

The cell processing apparatus may further comprise a driving unit disposed outside the embedding member, for feeding of a solution in the introduced cell solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the introduced cell solution-feeding channel.

The driving unit and slave unit in the cell processing apparatus may also be connected by magnetic force.

The cell processing instrument in the cell processing apparatus may also comprise an amplifying culturing vessel, disposed inside the embedding member, that carries out amplifying culturing of a plurality of cell masses comprising established stem cells.

The cell processing apparatus may still further comprise a stem cell culture medium storing unit, disposed outside the embedding member, that stores stem cell culture medium, and the communicating solution-feeding channel may also comprise a culture medium solution-feeding channel that allows communication between the stem cell culture medium storing unit and the amplifying culturing vessel.

The stem cell culture medium in the cell processing apparatus may be continuously supplied to the amplifying culturing vessel.

The stem cell culture medium in the cell processing apparatus may also be supplied to the amplifying culturing vessel at a prescribed timing.

The cell processing apparatus may still further comprise a cold storage unit, disposed outside the embedding member, that keeps the stem cell culture medium in cold storage.

The cell processing apparatus may still further comprise a waste liquid storage section, disposed outside the embedding member, that stores waste liquid, and the communicating solution-feeding channel may also comprise a waste liquid solution-feeding channel that allows communication between the amplifying culturing vessel and the waste liquid storage section.

The amplifying culturing vessel in the cell processing apparatus may also comprise a suspension culture vessel that comprises a dialysis tube in which the inducing factor-introduced cells and culture medium are to be accommodated, and a vessel in which the dialysis tube is to be placed, with the culture medium accommodable around the periphery of the dialysis tube.

The cell processing instrument in the cell processing apparatus may also comprise an initializing culturing vessel, disposed inside the embedding member, that cultures the inducing factor-introduced cells, an amplifying culturing vessel, disposed inside the embedding member, that carries out amplifying culturing of a plurality of cell masses comprising established stem cells, and an introduced cell solution-feeding channel, disposed inside the embedding member, that allows communication between the initializing culturing vessel and the amplifying culturing vessel.

The cell processing apparatus may further comprise a driving unit disposed outside the embedding member, for feeding of a solution in the introduced cell solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the introduced cell solution-feeding channel.

The cell processing instrument in the cell processing apparatus may also comprise a cell dissociater, disposed inside the embedding member, for dissociation of the cell masses provided to the introduced cell solution-feeding channel.

The cell processing instrument in the cell processing apparatus may also comprise a solution exchanger that exchanges the solution surrounding the cells.

The cell processing apparatus may still further comprise a cryopreservation liquid storing unit, disposed outside the embedding member, that contains a cryopreservation liquid, and the communicating solution-feeding channel may also comprise a cryopreservation liquid-feeding channel that allows communication between the cryopreservation liquid storing unit and the solution exchanger.

The cell processing apparatus may still further comprise a cryopreservation vessel, disposed outside the embedding member, for storage of the cryopreservation liquid in which cell masses have been dispersed, and the communicating solution-feeding channel may also comprise a freezing cell solution-feeding channel, that allows communication between the solution exchanger and the cryopreservation vessel.

The cell processing instrument in the cell processing apparatus may further comprise an amplifying culturing vessel, disposed inside the embedding member, that carries out amplifying culturing of a plurality of cell masses comprising established stem cells, a solution exchanger that exchanges the solution surrounding the cells, and an introduced cell solution-feeding channel, disposed inside the embedding member, that allows communication between the amplifying culturing vessel and the solution exchanger.

The cell processing apparatus may further comprise a driving unit disposed outside the embedding member, for feeding of a solution in the introduced cell solution-feeding channel.

The driving unit in the cell processing apparatus may be connected to an outer wall of the embedding member.

The cell processing apparatus may also be provided with a slave unit in the embedding member, to which driving force from the driving unit is transmitted, with the slave unit being connected to the introduced cell solution-feeding channel.

The cell processing instrument in the cell processing apparatus may also comprise a cell dissociater, disposed inside the embedding member, for dissociation of the cell masses provided to the introduced cell solution-feeding channel.

The cell processing instrument in the cell processing apparatus may also comprise a cell mass dissociater that dissociates cell masses.

Advantageous Effects of Invention

According to the invention it is possible to provide a cell processing system and a cell processing apparatus that allow treatment of cells without contamination of the surroundings.

DESCRIPTION OF EMBODIMENTS

Figure 1:
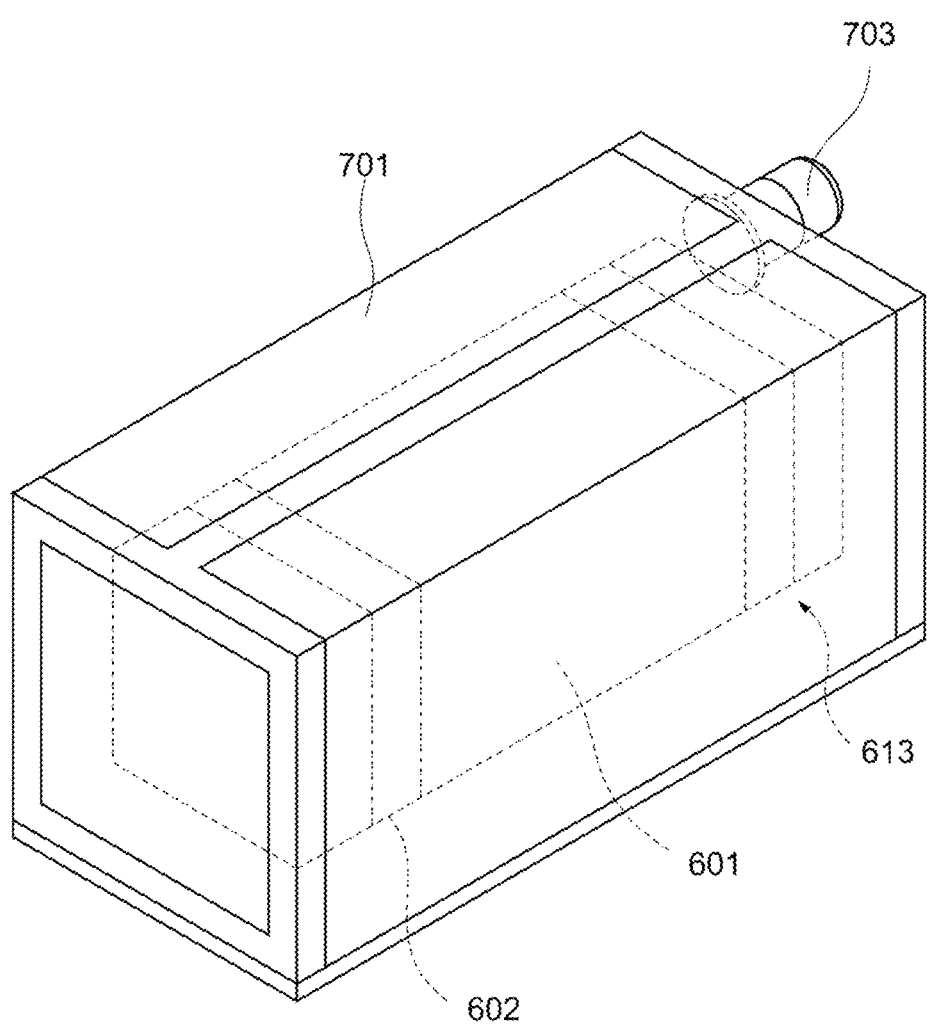
FIG. 1 is a schematic perspective view of a cell processing system according to an embodiment of the invention.

An embodiment of the invention will now be explained. In the accompanying drawings, identical or similar parts will be indicated by identical or similar reference numerals. However, the drawings are only schematic representations. The specific dimensions, therefore, should be judged in light of the following explanation. Furthermore, this naturally includes parts that have different dimensional relationships and proportions between drawings.

The present disclosure includes an invention that has been provisionally filed in the U.S. (62/356,199), and has already been issued a foreign application permit.

Figure 2:
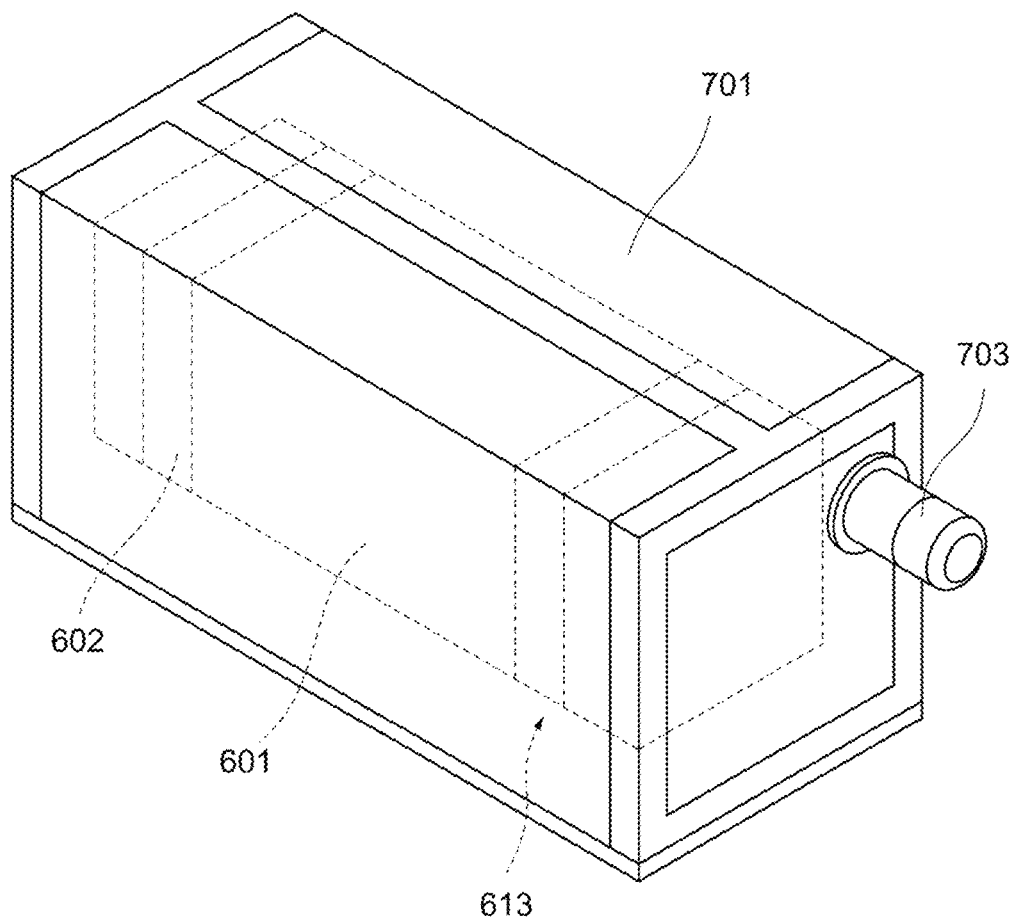
FIG. 2 is a schematic perspective view of a cell processing system according to an embodiment.
Figure 3:
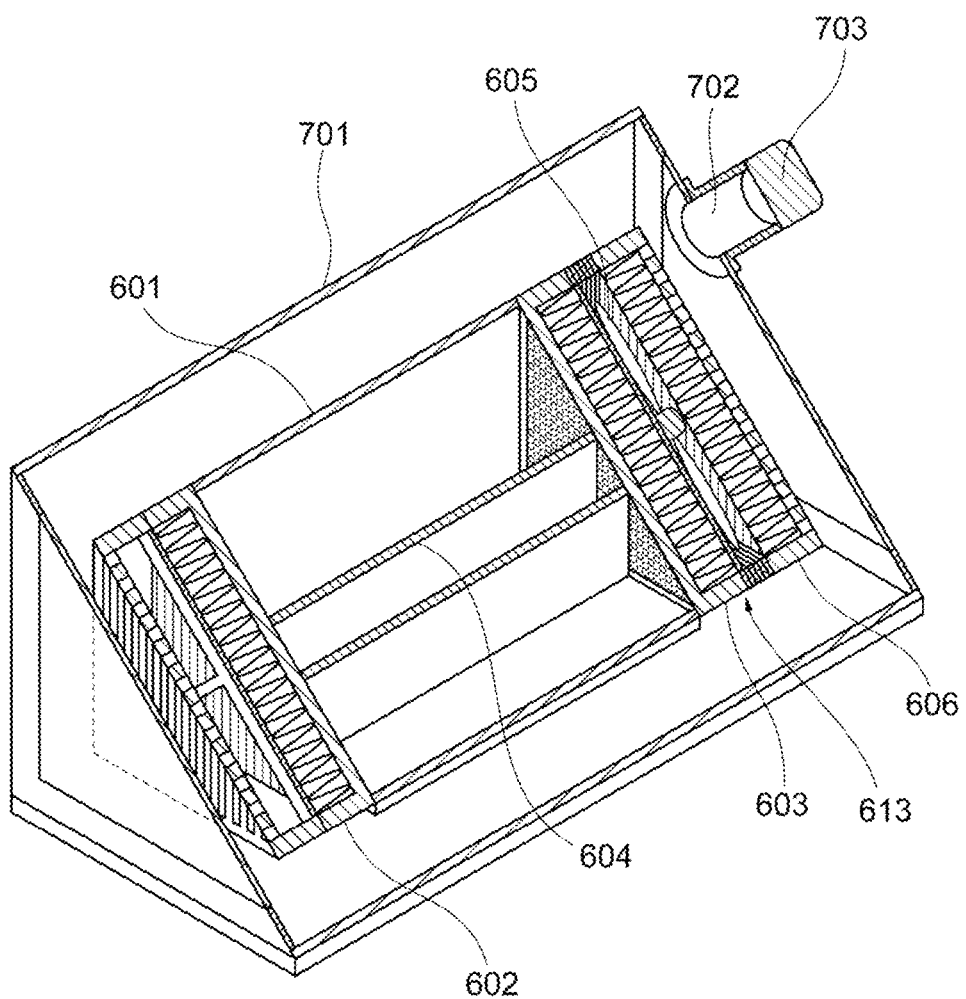
FIG. 3 is a schematic cross-sectional perspective view of a cell processing system according to an embodiment.

As shown in FIG. 1 to FIG. 3, the cell processing system according to this embodiment comprises an enclosure 601, an outer enclosure 701 that envelops the enclosure 601, an intake air purification filter 602 provided in the enclosure 601, that purifies gas that has been drawn in from outside the enclosure 601, a circulating apparatus, inside the outer enclosure 701, that circulates gas inside and outside the enclosure 601 in such a manner that gas in the outer enclosure 701 is drawn into the enclosure 601 through the intake air purification filter 602 and gas inside the enclosure 601 is discharged into the outer enclosure 701, and a cell processing apparatus for processing of cells, disposed inside the enclosure 601.

The enclosure 601 has a rectangular solid shape, for example, but this is not limitative. The enclosure 601 is made of a material that is able to withstand heat sterilization and ultraviolet sterilization, for example, but this is also not limitative. At least a portion of the enclosure 601 may be transparent so that the interior can be observed from outside. The enclosure 601 has an openable and closeable structure to allow the cell processing apparatus to be inserted into and removed from it.

The circulating apparatus comprises, for example, a gas discharger 613, provided in the enclosure 601, that draws in gas from inside the enclosure 601 and discharges purified gas out of the enclosure 601. The intake air purification filter 602 and gas discharger 613 are situated opposite each other, for example. Examples to be used for the intake air purification filter 602 include, but are not limited to, HEPA (High Efficiency Particulate Air) filters and URPA (Ultra Low Particulate Air) filters. A MEPA (Medium Efficiency Particulate Air) filter may also be used as the intake air purification filter 602, depending on the usage environment. The intake air purification filter 602 purifies gas that is to be drawn into the enclosure 601 from outside the enclosure 601.

As shown in FIG. 3, the gas discharger 613 comprises an exhaust system 605 that exhausts gas inside the enclosure 601 to the exterior of the enclosure 601, and an exhaust purification filter 603 that purifies gas that has been drawn in by the exhaust system 605. The exhaust system 605 comprises a fan, for example. The exhaust purification filter 603 may be situated facing the interior of the enclosure 601, upstream from the exhaust system 605. It is often difficult to accomplish sterilization of the exhaust system 605, which is an electrical device. Therefore, the exhaust purification filter 603 may be arranged upstream from the exhaust system 605, making it possible to inhibit contamination of the exhaust system 605. The gas discharger 613 may also comprise a second exhaust purification filter 606 disposed downstream from the exhaust system 605.

The materials of the exhaust purification filter 603 and the second exhaust purification filter 606 may be the same as for the intake air purification filter 602, for example. Even if the enclosure 601 interior becomes contaminated by the cell processing apparatus, the gas purified by the exhaust purification filter 603 and second exhaust purification filter 606 is exhausted to the outside of the enclosure 601. For example, even if the gas inside the enclosure 601 includes blood components or viruses, such impurities are captured by the exhaust purification filter 603. Moreover, even if the exhaust system 605 causes contamination of dust and the like in the gas, the dust is captured by the second exhaust purification filter 606.

As shown in FIG. 1 to FIG. 3, the outer enclosure 701 has a rectangular solid shape, for example, although this is not limitative. The outer enclosure 701 is made of a material that is able to withstand heat sterilization and ultraviolet sterilization, for example, but this is also not limitative. At least a portion of the outer enclosure 701 may be transparent so that the interior can be observed from outside. The outer enclosure 701 has an openable and closeable structure to allow the enclosure 601 to be inserted into and removed from it. However, the outer enclosure 701 preferably has an openable and closeable structure wherein the interior is completely closed when the pressure adjustment hole 702 is in the closed state, as described below.

As shown in FIG. 3, the outer enclosure 701 may be provided with a pressure adjustment hole 702 for adjustment of the pressure inside the outer enclosure 701. An occluding member 703 capable of occluding the pressure adjustment hole 702 is also preferably attached to the outer enclosure 701. A filter is disposed in the pressure adjustment hole 702. The material of the filter disposed in the pressure adjustment hole 702 is the same as for the intake air purification filter 602, for example.

Gas is able to flow through the pressure adjustment hole 702 when the gas pressure in the outer enclosure 701 is the same as outside the outer enclosure 701, for example. Gas that has exited out from the outer enclosure 701 through the pressure adjustment hole 702 is purified by the filter disposed in the pressure adjustment hole 702. Gas that has entered into the outer enclosure 701 through the pressure adjustment hole 702 is also purified by the filter disposed in the pressure adjustment hole 702.

Figure 4:
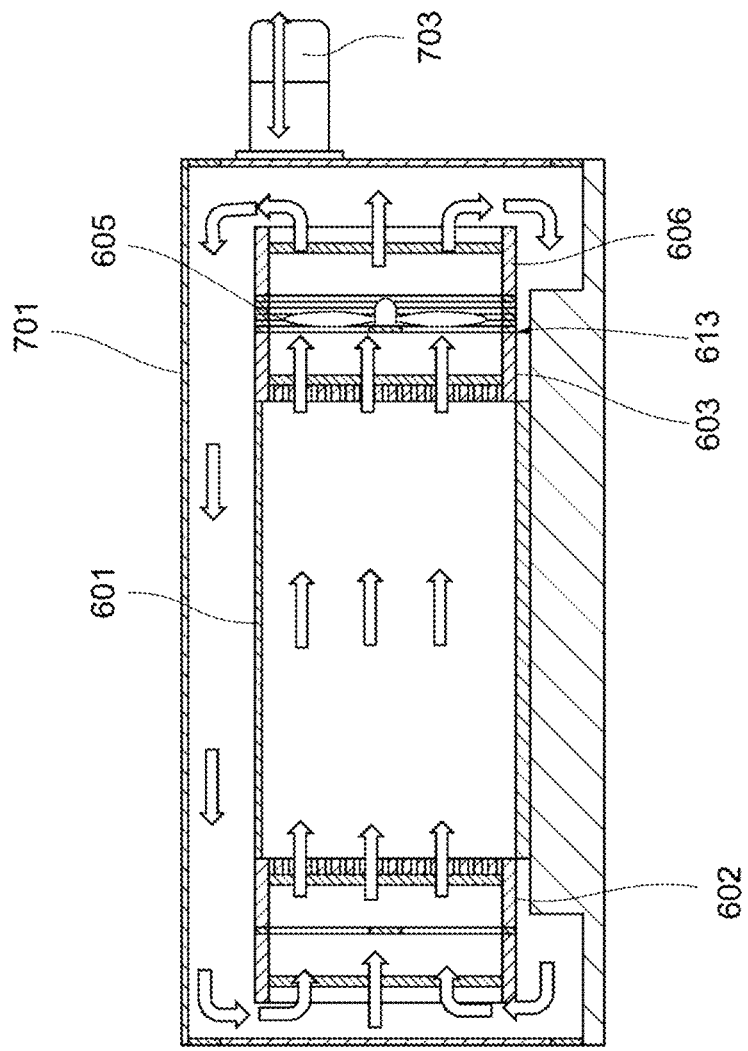
FIG. 4 is a schematic cross-sectional view of a cell processing system according to an embodiment.

As shown in FIG. 4, gas in the outer enclosure 701 is drawn into the enclosure 601 through the intake air purification filter 602. The gas inside the enclosure 601 is also discharged into the outer enclosure 701 by the gas discharger 613. Gas is therefore circulated inside and outside the enclosure 601 in the outer enclosure 701. Circulation of gas inside and outside the enclosure 601 in the outer enclosure 701 purifies not only gas inside the enclosure 601, but also gas inside the outer enclosure 701 which is outside of the enclosure 601, by the intake air purification filter 602, the exhaust purification filter 603 and the second exhaust purification filter 606. A cell processing system can thus be constructed wherein the cleanliness of the air inside the enclosure 601 and inside the outer enclosure 701 conforms to, for example, class ISO1 to ISO6 based on ISO standard 14644-1.

Figure 5:
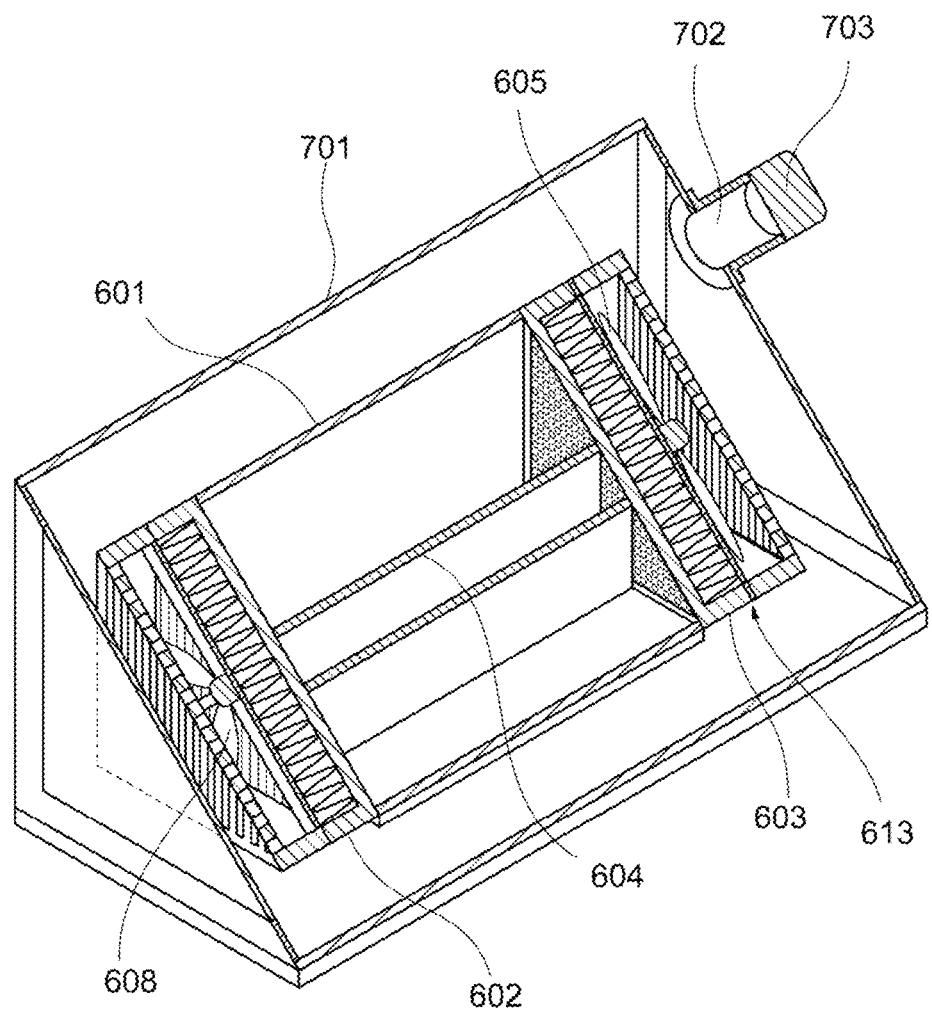
FIG. 5 is a schematic cross-sectional perspective view of a cell processing system according to an embodiment.
Figure 6:
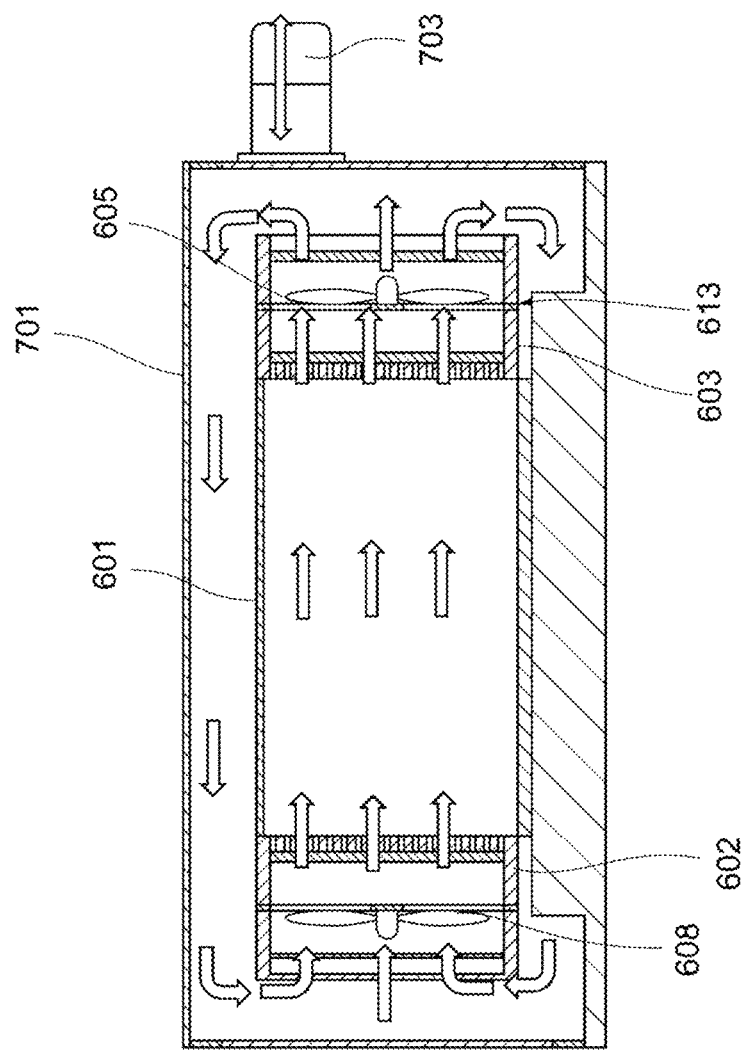
FIG. 6 is a schematic cross-sectional view of a cell processing system according to an embodiment.

As shown in FIG. 5 and FIG. 6, the second exhaust purification filter 606 may be omitted, depending on the usage environment. In addition, the circulating apparatus may further comprise an injector 608, provided in the enclosure 601, that draws in gas purified by the intake air purification filter 602, to the outside of the enclosure 601. The injector 608 comprises a fan, for example. The intake air purification filter 602 may be situated facing the interior of the enclosure 601, downstream from the injector 608.

Figure 7:
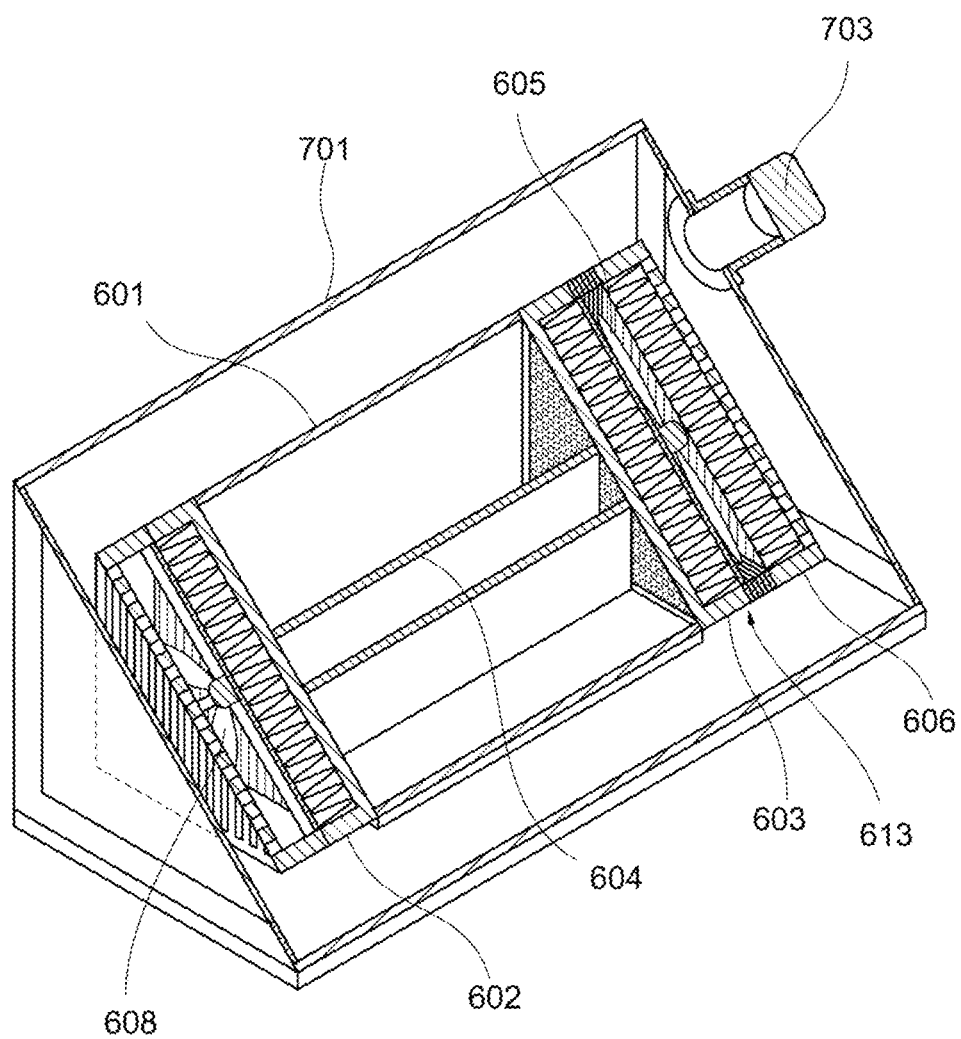
FIG. 7 is a schematic cross-sectional perspective view of a cell processing system according to an embodiment.
Figure 8:
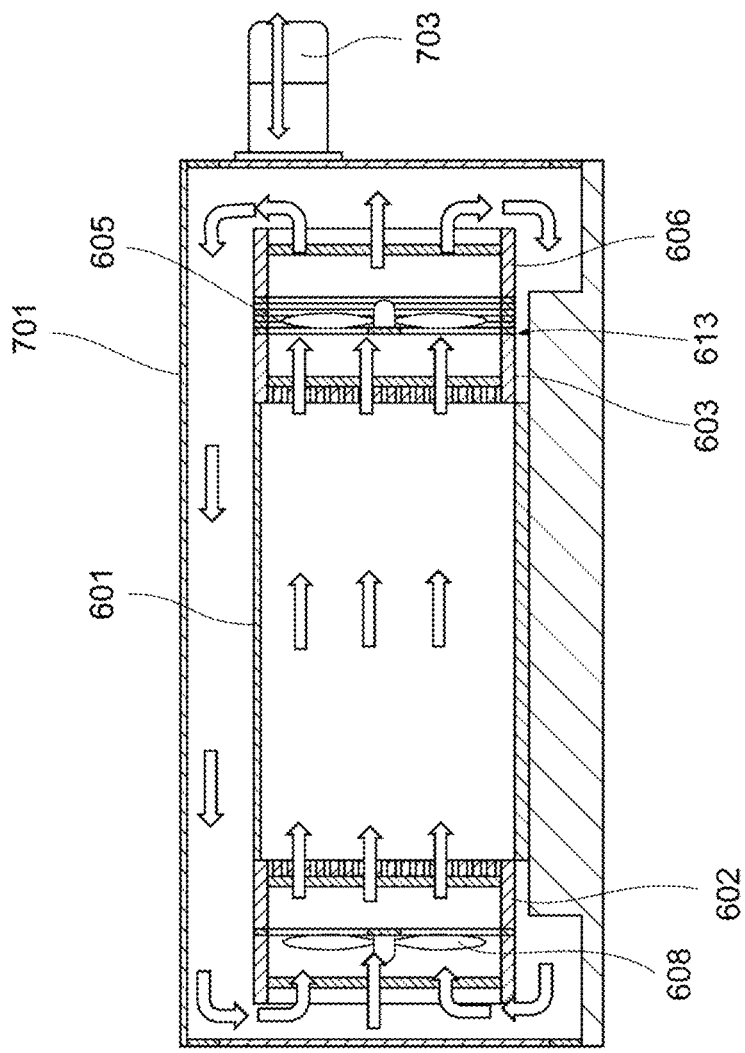
FIG. 8 is a schematic cross-sectional view of a cell processing system according to an embodiment.

Incidentally, as shown in FIG. 7 and FIG. 8, the cell processing system may comprise both the injector 608 and the second exhaust purification filter 606. The circulating apparatus may comprise both the injector 608 and the gas discharger 613, or it may comprise only either one.

Either or both the exhaust system 605 and injector 608 stream gas so that the enclosure 601 interior is at negative pressure compared to the enclosure 601 exterior. This can help prevent impurities in the enclosure 601 from diffusing to the outside of the enclosure 601. Depending on the usage environment, however, the enclosure 601 interior may be at positive pressure compared to the enclosure 601 exterior.

The cell processing system may also comprise a cleanliness sensor that monitors the cleanliness of gas inside the enclosure 601.

The cell processing system may further comprise a carbon dioxide concentration control device that controls the concentration of carbon dioxide ($CO_2$) inside the enclosure 601. The carbon dioxide concentration control device may control the carbon dioxide concentration so that the carbon dioxide concentration inside the enclosure 601 is at a prescribed value, such as 5%, for example. The carbon dioxide concentration control device may also comprise a carbon dioxide concentration sensor that monitors the carbon dioxide concentration of the gas inside the enclosure 601.

The cell processing system may further comprise an oxygen concentration control device that controls the concentration of oxygen ($O_2$) inside the enclosure 601. For example, the oxygen concentration control device controls the oxygen concentration so that the oxygen concentration inside the enclosure 601 is at a low oxygen state of no greater than 20%. The oxygen concentration control device may also comprise an oxygen concentration sensor that monitors the oxygen concentration of the gas inside the enclosure 601.

The cell processing system may further comprise a temperature regulating device that regulates the temperature inside the enclosure 601. The temperature regulating device may regulate the temperature so that the temperature inside the enclosure 601 is a prescribed value such as 37° C., for example. The temperature regulating device comprises, for example, a Peltier element. The temperature regulating device may also comprise a temperature sensor that monitors the temperature of the gas inside the enclosure 601.

The cell processing system may still further comprise a sterilizing device that performs sterilization inside the enclosure 601. The sterilizing device may be a dry heat sterilizing device. Alternatively, the sterilizing device may atomize or release a sterilizing gas such as ozone gas, hydrogen peroxide gas or formalin gas or a sterilizing solution such as ethanol, into the enclosure 601, to sterilize the interior of the enclosure 601. Also alternatively, the sterilizing device may irradiate ultraviolet rays (UV) or an electron beam into the enclosure 601 to sterilize the enclosure 601 interior. Sterilization of the enclosure 601 interior allows repeated culturing of cells to be carried out inside the enclosure 601. It can also minimize contamination of the enclosure 601 exterior and infection of operating personnel. The cell processing system may also comprise a sterilizing device that performs sterilization of the outer enclosure 701.

The enclosure 601 interior may be demarcated into multiple zones by partitions 604 or the like.

Figure 9:
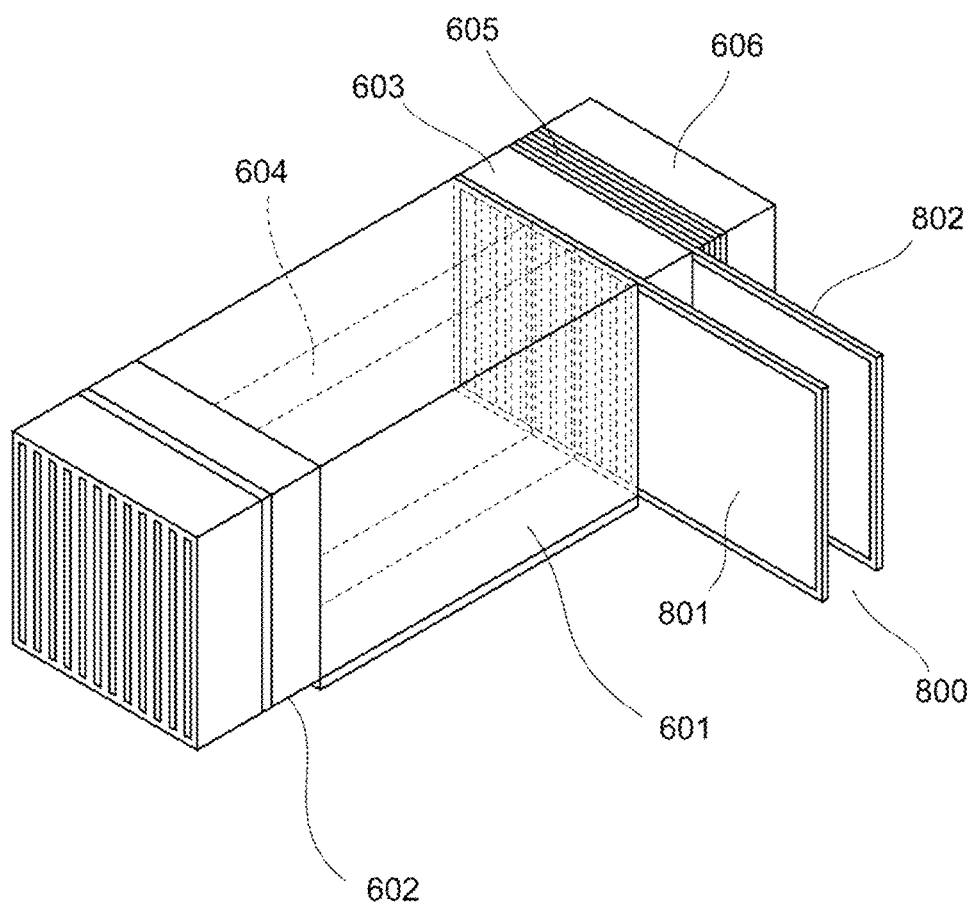
FIG. 9 is a schematic perspective view of a cell processing system according to an embodiment of the invention.
Figure 10:
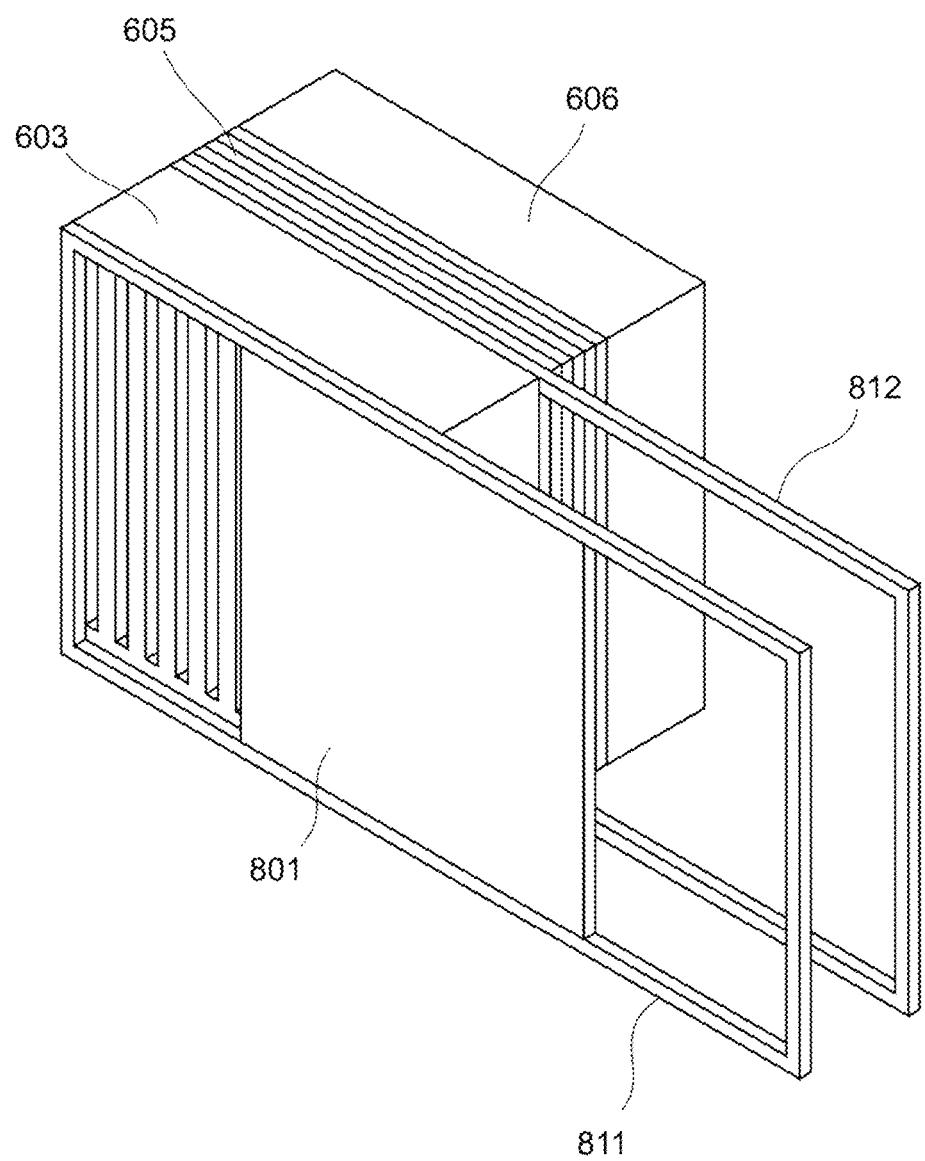
FIG. 10 is a schematic perspective view of a cell processing system according to an embodiment of the invention.
Figure 11:
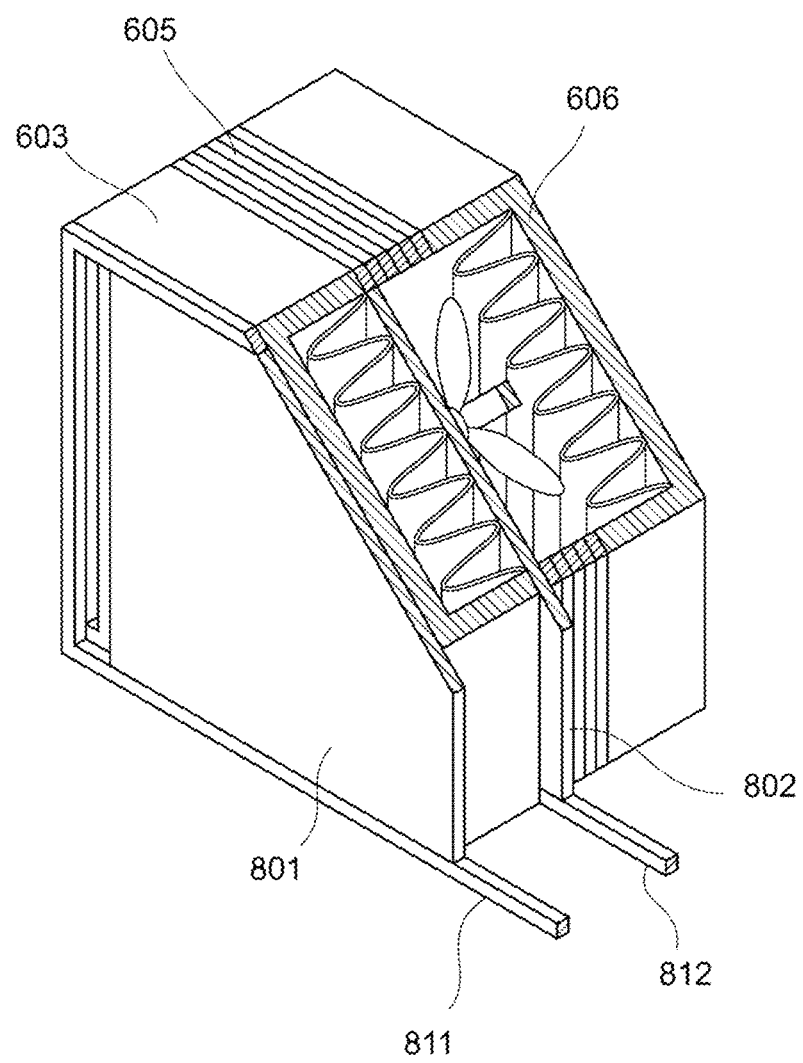
FIG. 11 is a schematic cross-sectional perspective view of a cell processing system according to an embodiment.

The cell processing system may also comprise a shielding member 800 that can be attached to the exhaust purification filter 603 so as to shield the exhaust purification filter 603, as shown in FIG. 9, FIG. 10 and FIG. 11. For example, the shielding member 800 comprises an enclosure side shielding member 801 that can be attached to the exhaust purification filter 603 so as to shield the exhaust purification filter 603 from the interior of the enclosure 601, and an exhaust system side shielding member 802 that can be attached to the exhaust purification filter 603 so as to shield the exhaust purification filter 603 from the exhaust system 605.

This cell processing system may further comprise a sterilizing device that sterilizes the exhaust purification filter 603 that is shielded by the shielding member 800. The sterilizing device sterilizes the exhaust purification filter 603 that is shielded by the shielding member 800, by the same method as for sterilization of the interior of the enclosure 601. Sterilization of the exhaust purification filter 603 with the sterilizing device can help prevent contamination of operating personnel during exchange of the exhaust purification filter 603.

Sterilization of the exhaust purification filter 603 that is shielded by the shielding member 800 can also help prevent exposure of the exhaust system 605 to the sterilization environment that may result in damage to the exhaust system 605. When the sterilizing device is a dry heat sterilizing device, the shielding member 800 may be made of an insulating material, for example. The shape of the shielding member 800 is not particularly restricted, and it may be in the form of a plate or a film.

The enclosure side shielding member 801 may be movable by a guide 811, as shown in FIG. 10 and FIG. 11. For example, the enclosure side shielding member 801 may move back and forth along the guide 811, between a location that does not shield the exhaust purification filter 603 and a location that does shield the exhaust purification filter 603.

The exhaust system side shielding member 802 may also be movable by a guide 812. For example, the exhaust system side shielding member 802 may move back and forth along the guide 812, between a location that does not shield the exhaust purification filter 603 and a location that does shield the exhaust purification filter 603.

Figure 12:
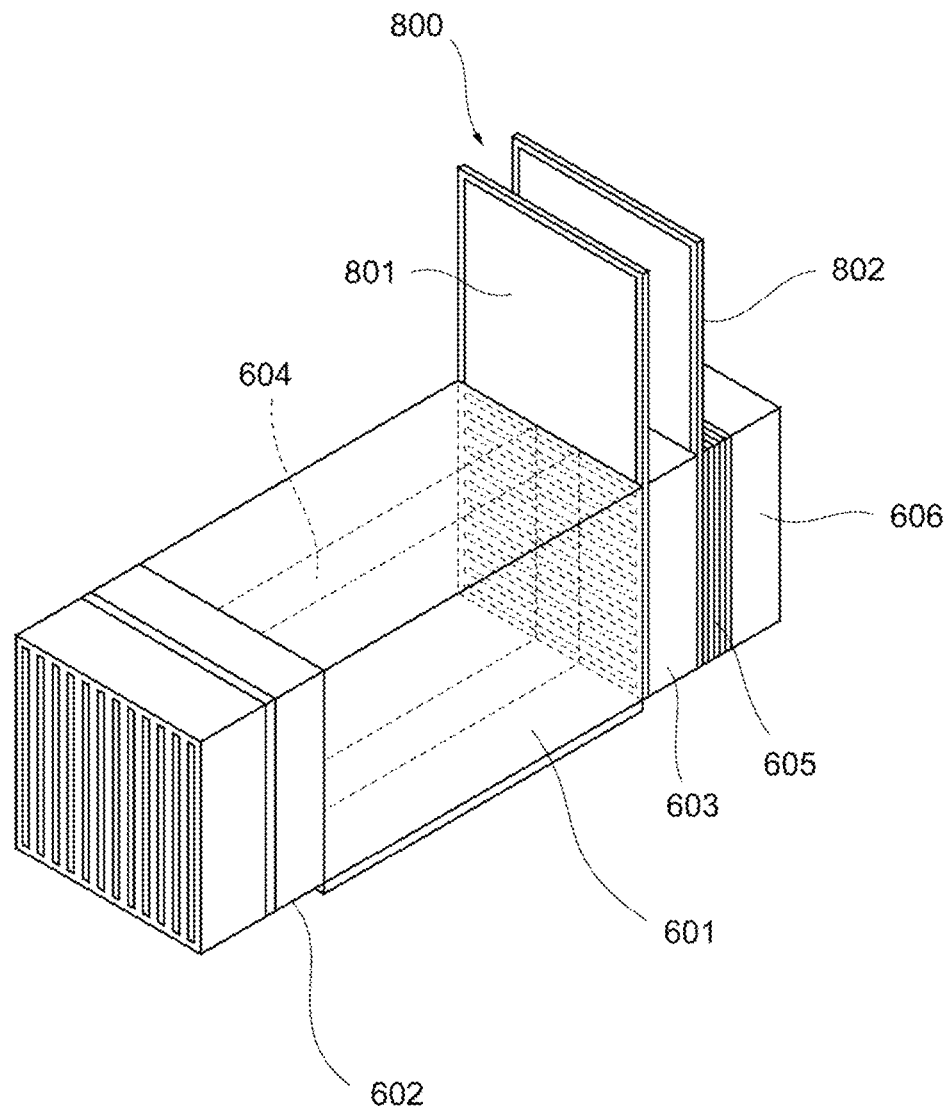
FIG. 12 is a schematic perspective view of a cell processing system according to an embodiment of the invention.

The enclosure side shielding member 801 and the exhaust system side shielding member 802 may be movable in the lateral direction with respect to the enclosure 601, or as shown in FIG. 12, they may be movable in the vertical direction with respect to the enclosure 601.

This cell processing system may still further comprise a shielding member that can be attached to the second exhaust purification filter 606 so as to shield the second exhaust purification filter 606. The shielding member that can be attached to the second exhaust purification filter 606 may comprise, for example, an exhaust system side shielding member that can be attached to the second exhaust purification filter 606 so as to shield the second exhaust purification filter 606 from the exhaust system 605.

The cell processing system may further comprise a sterilizing device that sterilizes the second exhaust purification filter 606 that is shielded by the shielding member. The sterilizing device sterilizes the second exhaust purification filter 606 that is shielded by the shielding member, by the same method as for sterilization of the interior of the enclosure 601. Sterilization of the second exhaust purification filter 606 with the sterilizing device can help prevent contamination of operating personnel during exchange of the second exhaust purification filter 606.

Sterilization of the second exhaust purification filter 606 that is shielded by the shielding member can also help prevent exposure of the exhaust system 605 to the sterilization environment that may result in damage to the exhaust system 605. When the sterilizing device is a dry heat sterilizing device, the shielding member that shields the second exhaust purification filter 606 may be made of an insulating material, for example. The shape of the shielding member that shields the second exhaust purification filter 606 is not particularly restricted, and it may be in the form of a plate or a film.

The shielding member that shields the second exhaust purification filter 606 may also be movable by a guide. For example, the shielding member may move back and forth along the guide, between a location that does not shield the second exhaust purification filter 606 and a location that does shield the second exhaust purification filter 606.

This cell processing system may still further comprise a shielding member that can be attached to the intake air purification filter 602 so as to shield the intake air purification filter 602. For example, the shielding member that can be attached to the intake air purification filter 602 comprises an enclosure side shielding member that can be attached to the intake air purification filter 602 so as to shield the intake air purification filter 602 from the interior of the enclosure 601, and an injector side shielding member that can be attached to the intake air purification filter 602 so as to shield the intake air purification filter 602 from the injector 608.

This cell processing system may further comprise a sterilizing device that sterilizes the intake air purification filter 602 that is shielded by the shielding member. The sterilizing device sterilizes the intake air purification filter 602 that is shielded by the shielding member, by the same method as for sterilization of the interior of the enclosure 601. Sterilization of the intake air purification filter 602 with the sterilizing device can help prevent contamination of operating personnel during exchange of the intake air purification filter 602.

Sterilization of the intake air purification filter 602 that is shielded by the shielding member can also can help prevent exposure of the injector 608 to the sterilization environment that may result in damage to the injector 608. When the sterilizing device is a dry heat sterilizing device, the shielding member that shields the intake air purification filter 602 may be made of an insulating material, for example. The shape of the shielding member that shields the intake air purification filter 602 is not particularly restricted, and it may be in the form of a plate or a film.

The shielding member that shields the intake air purification filter 602 may also be movable by a guide. For example, the shielding member may move back and forth along the guide, between a location that does not shield the intake air purification filter 602 and a location that does shield the intake air purification filter 602.

Figure 13:
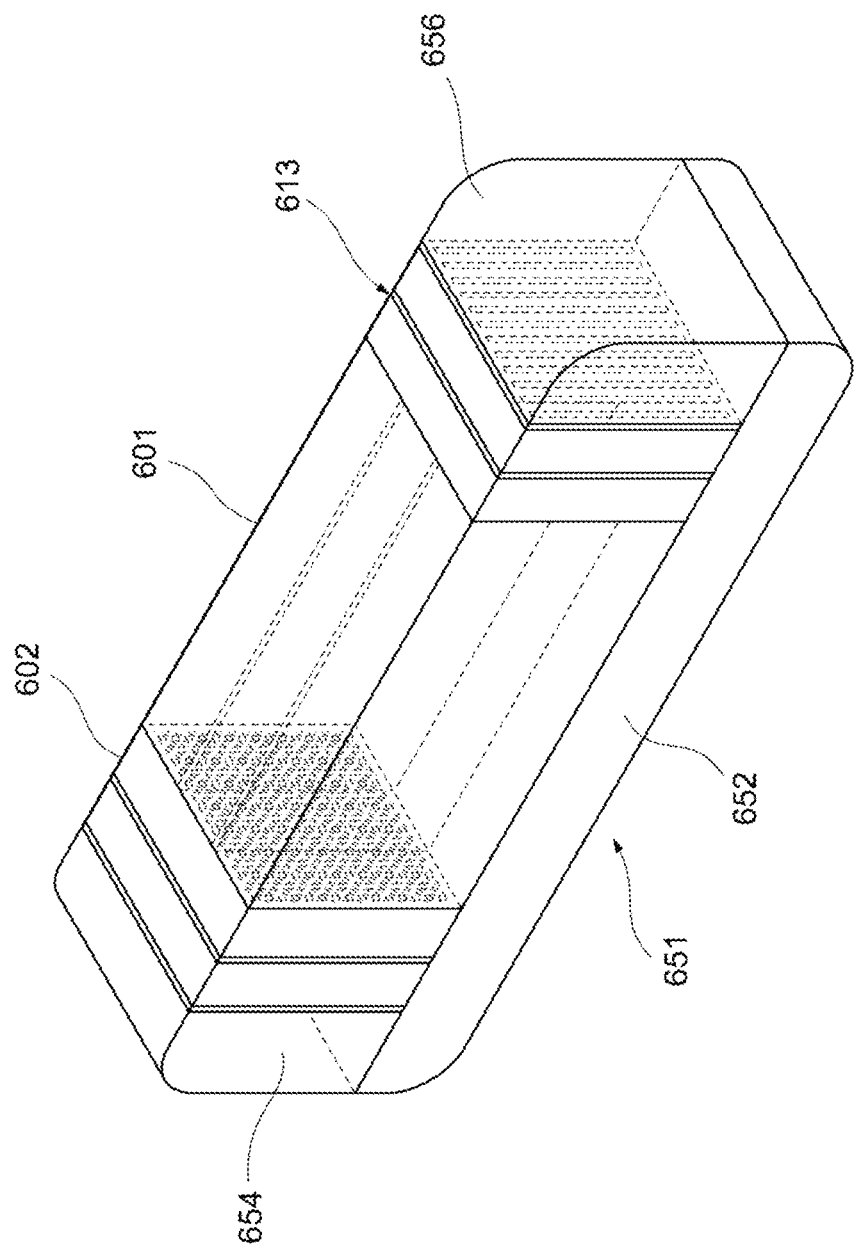
FIG. 13 is a schematic perspective view of a cell processing system according to an embodiment of the invention.
Figure 14:
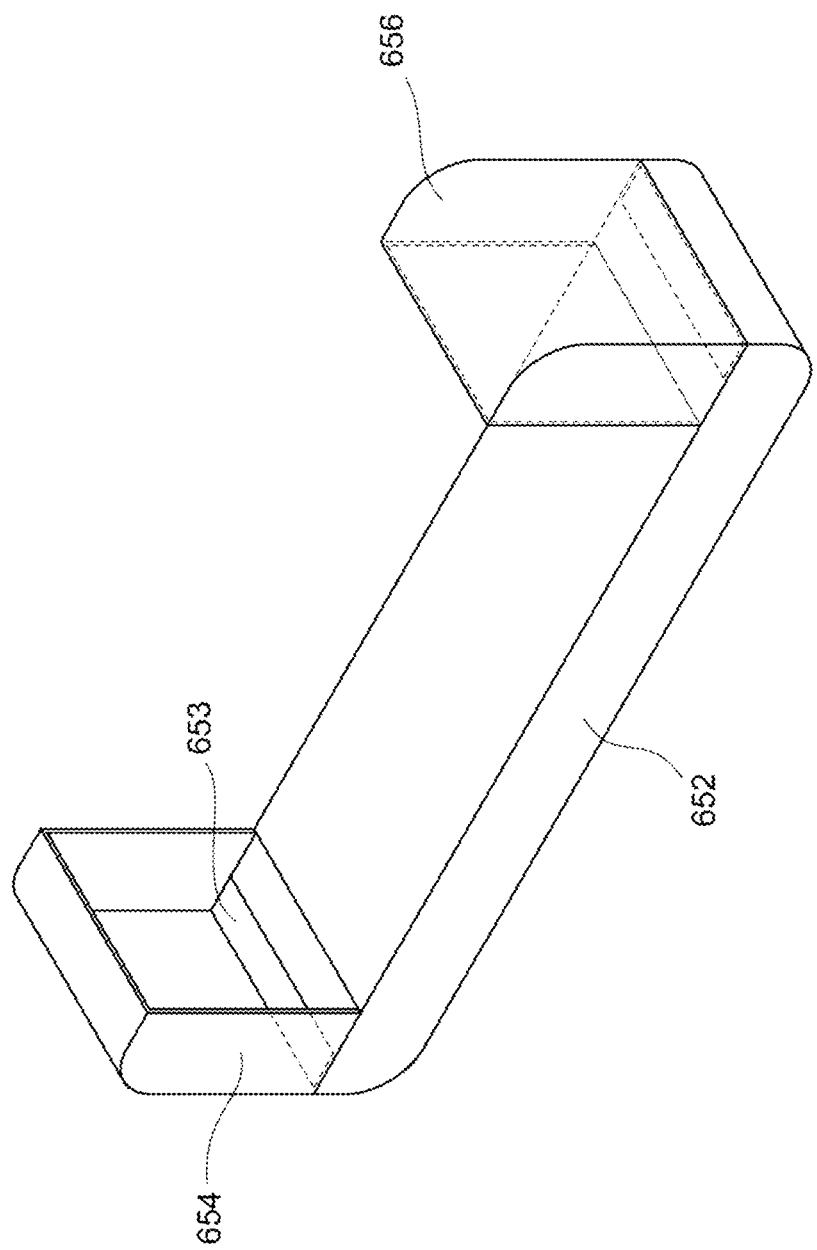
FIG. 14 is a schematic perspective view of a cell processing system according to an embodiment of the invention.
Figure 15:
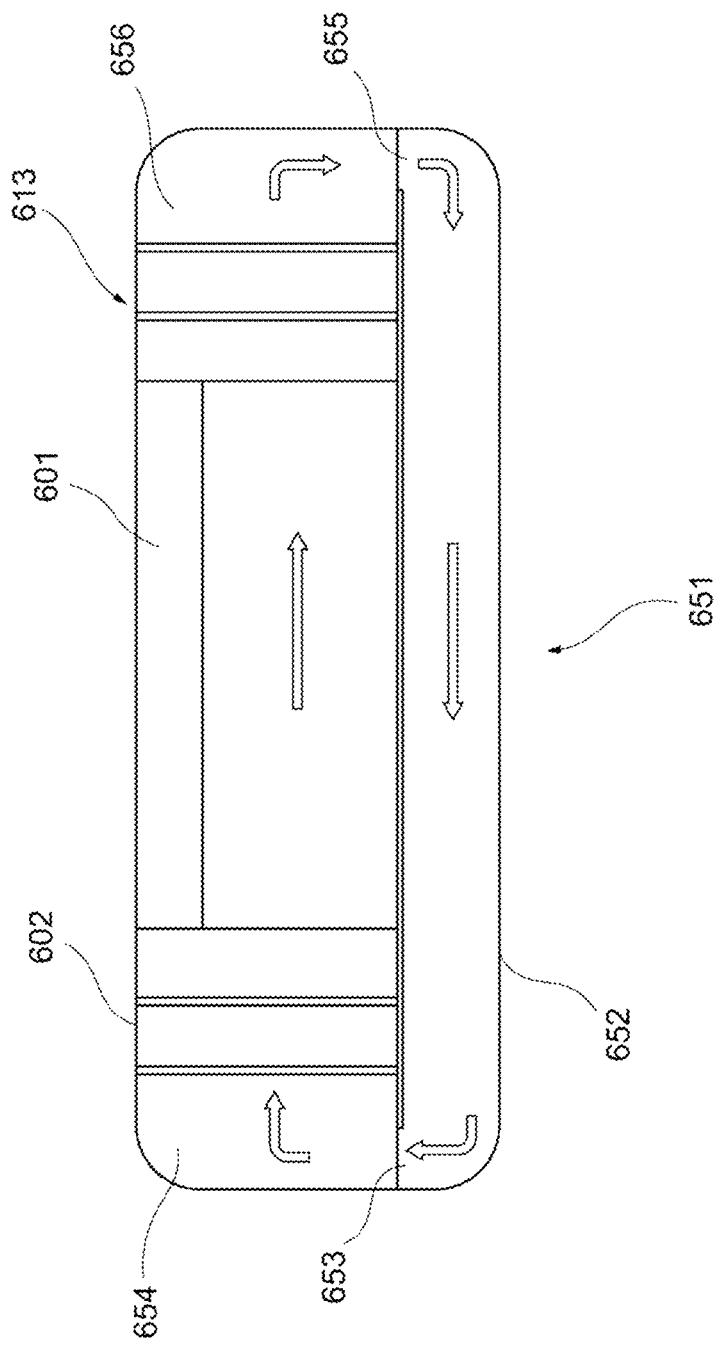
FIG. 15 is a schematic cross-sectional view of a cell processing system according to an embodiment.

Alternatively, as shown in FIG. 13 to FIG. 15, the cell processing system according to this embodiment may comprise an enclosure 601, an intake air purification filter 602 provided in the enclosure 601, that purifies gas that has been drawn in from outside the enclosure 601, a returning member 651 with a hollow interior, to return gas discharged from the enclosure 601 back to the intake air purification filter 602, a circulating apparatus that circulates gas between the enclosure and the returning member, in such a manner that the gas inside the enclosure 601 is discharged into the returning member 651 and the gas in the returning member 651 is drawn into the enclosure 601 through the intake air purification filter 602, and a cell processing apparatus for processing of cells, disposed inside the enclosure 601.

The enclosure 601 shown in FIG. 13 to FIG. 15 may have the same construction as the enclosure 601 explained using FIG. 1 to FIG. 9. The enclosure 601 therefore has a rectangular solid shape, for example, although this is not limitative. The enclosure 601 is made of a material that is able to withstand the sterilization mentioned above, for example, although this is also not limitative. At least a portion of the enclosure 601 may be transparent so that the interior can be observed from outside. The enclosure 601 has an openable and closeable structure to allow the cell processing apparatus to be inserted into and removed from it.

The circulating apparatus comprises, for example, a gas discharger 613, provided in the enclosure 601, that draws in gas from inside the enclosure 601 and discharges purified gas out of the enclosure 601. The intake air purification filter 602 and gas discharger 613 are situated opposite each other, for example. Examples to be used for the intake air purification filter 602 include, but are not limited to, HEPA (High Efficiency Particulate Air) filters and URPA (Ultra Low Particulate Air) filters. A MEPA (Medium Efficiency Particulate Air) filter may also be used as the intake air purification filter 602, depending on the usage environment. The intake air purification filter 602 purifies gas that is to be drawn into the enclosure 601 from outside the enclosure 601.

In the cell processing system illustrated in FIG. 13 to FIG. 15, the gas discharger 613 comprises an exhaust system 605 that exhausts gas inside the enclosure 601 into the returning member 651, and an exhaust purification filter 603 that purifies gas that has been drawn in by the exhaust system 605, as shown in FIG. 3. The exhaust system 605 comprises a fan, for example. The exhaust purification filter 603 may be situated facing the interior of the enclosure 601, upstream from the exhaust system 605. It is often difficult to accomplish sterilization of the exhaust system 605, which is an electrical device. By therefore arranging the exhaust purification filter 603 upstream from the exhaust system 605, it is possible to inhibit contamination of the exhaust system 605. The gas discharger 613 may also comprise a second exhaust purification filter 606 disposed downstream from the exhaust system 605.

The materials of the exhaust purification filter 603 and the second exhaust purification filter 606 may be the same as for the intake air purification filter 602, for example. Even if the enclosure 601 interior becomes contaminated by the cell processing apparatus, the gas purified by the exhaust purification filter 603 and second exhaust purification filter 606 is exhausted into the returning member 651. For example, even if the gas inside the enclosure 601 includes blood components or viruses, such impurities are captured by the exhaust purification filter 603. Moreover, even if the exhaust system 605 causes contamination of dust and the like in the gas, the dust is captured by the second exhaust purification filter 606.

As shown in FIG. 13 to FIG. 15, the returning member 651 has a shape that engages with the enclosure 601, for example, although this is not limitative. The returning member 651 comprises, for example, a base 652 with a hollow interior, in contact with the bottom of the enclosure 601, a first cover 654 that allows communication between a first opening 653 provided in the base 652 and a ventilation unit provided on the first end face of the enclosure 601, and a second cover 656 that allows communication between a second opening 655 provided in the base 652 and a ventilation unit provided in the enclosure 601.

The first cover 654 covers the intake air purification filter 602 serving as the ventilation unit provided on the first end face. The second cover 656 covers the gas discharger 613 serving as the ventilation unit provided on the second end face.

The returning member 651 is made of a material that is able to withstand sterilization, similar to the enclosure 601, although this is not limitative. The returning member in this cell processing system may be a duct.

As shown in FIG. 15, the gas inside the enclosure 601 is also discharged into the returning member 651 by the gas discharger 613. Also, the gas in the returning member 651 is drawn into the enclosure 601 through the intake air purification filter 602. The gas therefore circulates between the enclosure 601 and the returning member 651. Circulation of gas between the enclosure 601 and the returning member 651 purifies not only gas inside the enclosure 601, but also gas inside the returning member 651 which is outside of the enclosure 601, by the intake air purification filter 602, the exhaust purification filter 603 and the second exhaust purification filter 606. A cell processing system can thus be constructed wherein the cleanliness of the air inside the enclosure 601 and inside the returning member 651 conforms to, for example, class ISO1 to ISO6 based on ISO standard 14644-1.

In the cell processing system illustrated in FIG. 13 to FIG. 15 as well, the second exhaust purification filter 606 may be omitted as was shown in FIG. 5 and FIG. 6, depending on the usage environment. In addition, the circulating apparatus may further comprise an injector 608, provided in the enclosure 601, that draws in gas purified by the intake air purification filter 602, from inside the returning member 651. The injector 608 comprises a fan, for example. The intake air purification filter 602 may be situated facing the interior of the enclosure 601, downstream from the injector 608.

The cell processing system illustrated in FIG. 13 to FIG. 15 as well, may comprise both the injector 608 and the second exhaust purification filter 606, as was shown in FIG. 7 and FIG. 8. The circulating apparatus may comprise both the injector 608 and the gas discharger 613, or it may comprise only either one.

Either or both the exhaust system 605 and injector 608 stream gas so that the enclosure 601 interior is at negative pressure compared to the enclosure 601 exterior. This can help prevent impurities in the enclosure 601 from diffusing to the outside of the enclosure 601. Depending on the usage environment, however, the enclosure 601 interior may be at positive pressure compared to the enclosure 601 exterior.

Similar to the cell processing system illustrated in FIG. 1 to FIG. 9, the cell processing system shown in FIG. 13 to FIG. 15 may also comprise one or all of a cleanliness sensor that monitors the cleanliness of gas inside the enclosure 601, a carbon dioxide concentration control device that controls the concentration of carbon dioxide ($CO_2$) inside the enclosure 601, an oxygen concentration control device that controls the concentration of oxygen ($O_2$) inside the enclosure 601, a temperature regulating device that regulates the temperature inside the enclosure 601, and a sterilizing device that sterilizes the interior of the enclosure 601.

The enclosure 601 interior may be demarcated into multiple zones by partitions 604 or the like.

The cell processing system shown in FIG. 13 to FIG. 15 as well may comprise a shielding member 800 that can be attached to the exhaust purification filter 603 so as to shield the exhaust purification filter 603, as shown in FIG. 9, FIG. 10 and FIG. 11. For example, the shielding member 800 comprises an enclosure side shielding member 801 that can be attached to the exhaust purification filter 603 so as to shield the exhaust purification filter 603 from the interior of the enclosure 601, and an exhaust system side shielding member 802 that can be attached to the exhaust purification filter 603 so as to shield the exhaust purification filter 603 from the exhaust system 605.

The cell processing system shown in FIG. 13 to FIG. 15 as well may further comprise a sterilizing device that sterilizes the exhaust purification filter 603 that is shielded by the shielding member 800, as shown in FIG. 9, FIG. 10 and FIG. 11. The sterilizing device sterilizes the exhaust purification filter 603 that is shielded by the shielding member 800, by the same method as for sterilization of the interior of the enclosure 601. Sterilization of the exhaust purification filter 603 with the sterilizing device can help prevent contamination of operating personnel during exchange of the exhaust purification filter 603.

Sterilization of the exhaust purification filter 603 that is shielded by the shielding member 800 can also help prevent exposure of the exhaust system 605 to the sterilization environment that may result in damage to the exhaust system 605. When the sterilizing device is a dry heat sterilizing device, the shielding member 800 may be made of an insulating material, for example. The shape of the shielding member 800 is not particularly restricted, and it may be in the form of a plate or a film.

In the cell processing system shown in FIG. 13 to FIG. 15 as well, the enclosure side shielding member 801 may be movable by a guide 811, as shown in FIG. 10 and FIG. 11. For example, the enclosure side shielding member 801 may move back and forth along the guide 811, between a location that does not shield the exhaust purification filter 603 and a location that does shield the exhaust purification filter 603.

The exhaust system side shielding member 802 may also be movable by the guide 812. For example, the exhaust system side shielding member 802 may move back and forth along the guide 812, between a location that does not shield the exhaust purification filter 603 and a location that does shield the exhaust purification filter 603.

The enclosure side shielding member 801 and the exhaust system side shielding member 802 may be movable in the lateral direction with respect to the enclosure 601, or as shown in FIG. 12, they may be movable in the vertical direction with respect to the enclosure 601.

The cell processing system shown in FIG. 13 to FIG. 15 as well may further comprise a shielding member that can be attached to the second exhaust purification filter 606 so as to shield the second exhaust purification filter 606, as shown in FIG. 12. The shielding member that can be attached to the second exhaust purification filter 606 may comprise, for example, an exhaust system side shielding member that can be attached to the second exhaust purification filter 606 so as to shield the second exhaust purification filter 606 from the exhaust system 605.

The cell processing system shown in FIG. 13 to FIG. 15 may further comprise a sterilizing device that sterilizes the second exhaust purification filter 606 that is shielded by the shielding member, as shown in FIG. 12. The sterilizing device sterilizes the second exhaust purification filter 606 that is shielded by the shielding member, by the same method as for sterilization of the interior of the enclosure 601. Sterilization of the second exhaust purification filter 606 with the sterilizing device can help prevent contamination of operating personnel during exchange of the second exhaust purification filter 606.

Sterilization of the second exhaust purification filter 606 that is shielded by the shielding member can also help prevent exposure of the exhaust system 605 to the sterilization environment that may result in damage to the exhaust system 605. When the sterilizing device is a dry heat sterilizing device, the shielding member that shields the second exhaust purification filter 606 may be made of an insulating material, for example. The shape of the shielding member that shields the second exhaust purification filter 606 is not particularly restricted, and it may be in the form of a plate or a film.

The shielding member that shields the second exhaust purification filter 606 may also be movable by a guide. For example, the shielding member may move back and forth along the guide, between a location that does not shield the second exhaust purification filter 606 and a location that does shield the second exhaust purification filter 606.

The cell processing system shown in FIG. 13 to FIG. 15 as well may further comprise a shielding member that can be attached to the intake air purification filter 602 so as to shield the intake air purification filter 602, as shown in FIG. 12. For example, the shielding member that can be attached to the intake air purification filter 602 comprises an enclosure side shielding member that can be attached to the intake air purification filter 602 so as to shield the intake air purification filter 602 from the interior of the enclosure 601, and an injector side shielding member that can be attached to the intake air purification filter 602 so as to shield the intake air purification filter 602 from the injector 608.

The cell processing system shown in FIG. 13 to FIG. 15 as well may further comprise a sterilizing device that sterilizes the intake air purification filter 602 that is shielded by the shielding member. The sterilizing device sterilizes the intake air purification filter 602 that is shielded by the shielding member, by the same method as for sterilization of the interior of the enclosure 601. Sterilization of the intake air purification filter 602 with the sterilizing device can help prevent contamination of operating personnel during exchange of the intake air purification filter 602.

Sterilization of the intake air purification filter 602 that is shielded by the shielding member can also can help prevent exposure of the injector 608 to the sterilization environment that may result in damage to the injector 608. When the sterilizing device is a dry heat sterilizing device, the shielding member that shields the intake air purification filter 602 may be made of an insulating material, for example. The shape of the shielding member that shields the intake air purification filter 602 is not particularly restricted, and it may be in the form of a plate or a film.

The shielding member that shields the intake air purification filter 602 may also be movable by a guide. For example, the shielding member may move back and forth along the guide, between a location that does not shield the intake air purification filter 602 and a location that does shield the intake air purification filter 602.

Figure 16:
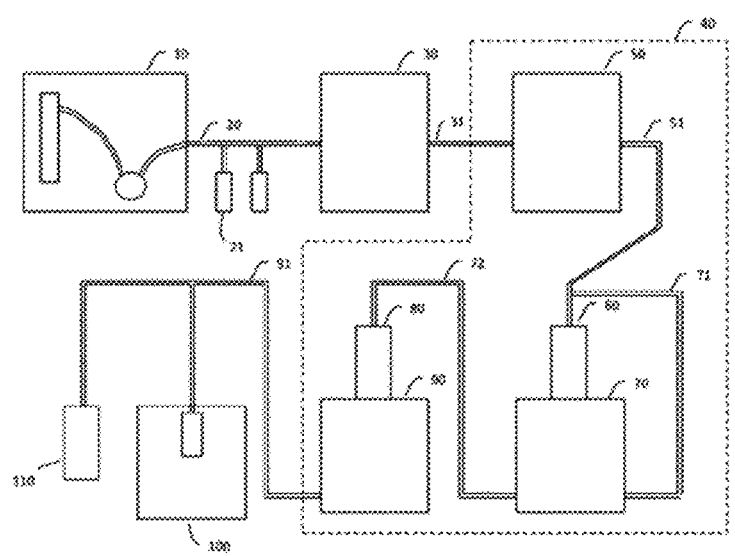
FIG. 16 is a schematic view of a cell processing apparatus according to an embodiment.

The cell processing apparatus disposed inside the enclosure 601 comprises, as shown in FIG. 16, a separating device 10 that separates cells from blood, a preintroduction cell solution-feeding channel 20 through which a cell-containing solution that has been separated by the separating device 10 passes, an inducing factor solution-feeding mechanism 21 that introduces a pluripotency inducing factor into the preintroduction cell solution-feeding channel 20, a factor introducing device 30 connected to the preintroduction cell solution-feeding channel 20, that introduces the pluripotency inducing factor into the cells to prepare inducing factor-introduced cells, a cell mass preparation device 40 that cultures the inducing factor-introduced cells to prepare a plurality of cell masses comprising stem cells, and a packaging device 100 that packages each of the plurality of cell masses in order.

The separating device 10 receives vials containing human blood, for example. The separating device 10 comprises an anticoagulant tank that stores anticoagulants such as ethylenediaminetetraacetic acid (EDTA), heparin and biologically standardized blood storage Solution A (ACD Solution A, product of Terumo Corp.), for example. The separating device 10 employs a pump or the like to add an anticoagulant to human blood from the anticoagulant tank.

In addition, the separating device 10 comprises a separating reagent tank that stores a mononuclear cell separating reagent such as Ficoll-Paque PREMIUM® (product of GE Healthcare, Japan). The separating device 10 employs a pump or the like to inject 5 mL of mononuclear cell separating reagent from the separating reagent tank into each of two 15 mL tubes, for example. Resin bags may also be used instead of tubes.

The separating device 10 also comprises a buffering solution tank that stores a buffering solution such as phosphate-buffered saline (PBS). The separating device 10 employs a pump to add 5 mL of buffering solution from the buffering solution tank to 5 mL of human blood, for example, to dilute it. In addition, the separating device 10 employs a pump or the like to add 5 mL of the diluted human blood to each of the mononuclear cell separating reagents in the tubes.

The separating device 10 further comprises a temperature-adjustable centrifuge. The centrifuge may be set to 18° C., for example. The separating device 10 employs a moving apparatus or the like to place the tubes in which the mononuclear cell separating reagent and human blood have been placed, into holders of the centrifuge. The centrifuge performs centrifugation of the solutions in the tubes for 30 minutes at 400×g, for example. Resin bags may also be centrifuged instead of tubes.

After centrifugation, the separating device 10 collects the intermediate layers that have become turbid and white by the mononuclear cells in the solutions in the tubes, using a pump or the like. The separating device 10 employs a pump or the like to deliver the recovered mononuclear cell suspensions to the preintroduction cell solution-feeding channel 20. Alternatively, the separating device 10 also adds 12 mL of PBS, for example, to 2 mL of the recovered mononuclear cell solutions, and places the tubes in holders of the centrifuge. The centrifuge performs centrifugation of the solutions in the tubes for 10 minutes at 200×g, for example.

After centrifugation, the separating device 10 employs a pump or the like to remove the supernatants of the solutions in the tubes by suction, and adds 3 mL of mononuclear cell culture medium such as X-VIVO 10® (Lonza, Japan) to the mononuclear cell solutions in the tubes to prepare suspensions. The separating device 10 employs a pump or the like to deliver the mononuclear cell suspensions to the preintroduction cell solution-feeding channel 20. The separating device 10 may also employ a dialysis membrane to separate the mononuclear cells from the blood. When using somatic cells such as fibroblasts previously separated from skin or the like, the separating device 10 is not necessary.

The separating device 10 may also separate cells suitable for induction by a method other than centrifugal separation. For example, if the cells to be separated are T cells, cells that are CD3-, CD4- or CD8-positive may be separated by panning. If the cells to be separated are vascular endothelial precursor cells, then cells that are CD34-positive may be separated by panning. If the cells to be separated are B cells, then cells that are CD10-, CD19- or CD20-positive may be separated by panning. The separation may also be carried out by a magnetic-activated cell sorting (MACS) method or flow cytometry, without limitation to panning. Moreover, the cells suitable for induction are not limited to cells derived from blood.

The inducing factor solution-feeding mechanism 21 comprises an inducing factor introducing reagent tank that stores an inducing factor introducing reagent solution. The inducing factor introducing reagent solution such as a gene transfer reagent solution includes, for example, an electroporation solution such as Human T Cell Nucleofector® (Lonza, Japan), a supplement solution, and a plasmid set. The plasmid set includes, for example, 0.83 µg of pCXLE-hOCT3/4-shp53-F, 0.83 µg of pCXLE-hSK, 0.83 µg of pCE-hUL and 0.5 µg of and pCXWB-EBNA1. The inducing factor solution-feeding mechanism 21 employs a micropump or the like to deliver the inducing factor introducing reagent solution to the preintroduction cell solution-feeding channel 20, in such a manner that the mononuclear cell suspension is suspended in the inducing factor introducing reagent solution.

The inner wall of the preintroduction cell solution-feeding channel 20 may be coated with poly-HEMA (poly 2-hydroxyethyl methacrylate) to render it non-cell-adherent, so that the cells do not adhere. Alternatively, a material resistant to cell adhesion may be used as the material for the preintroduction cell solution-feeding channel 20. Also, by using a material with good thermal diffusivity and $CO_2$ permeability as the material of the preintroduction cell solution-feeding channel 20, the conditions in the preintroduction cell solution-feeding channel 20 will be equivalent to the controlled temperature and $CO_2$ concentration in the enclosure 601. In addition, a back-flow valve may be provided in the preintroduction cell solution-feeding channel 20 from the viewpoint of preventing contamination.

The factor introducing device 30 connected to the preintroduction cell solution-feeding channel 20 is an electroporator, for example, and it receives a liquid mixture of the inducing factor introducing reagent solution and mononuclear cell suspension and carries out plasmid electroporation in the mononuclear cells. After carrying out electroporation, the factor introducing device 30 adds mononuclear cell culture medium to the solution containing the plasmid-electroporated mononuclear cells. The factor introducing device 30 employs a pump or the like to deliver the solution containing the plasmid-electroporated mononuclear cells (hereunder referred to as "inducing factor-introduced cells") to the introduced cell solution-feeding channel 31.

The factor introducing device 30 is not limited to an electroporator. The factor introducing device 30 may also introduce RNA coding for an initializing factor into the cells by a lipofection method. A lipofection method is a method in which a complex of nucleic acid as a negatively charged substance with positively charged lipids, is formed by electrical interaction, and the complex is incorporated into cells by endocytosis or membrane fusion. Lipofection is advantageous as it creates little damage to cells and has excellent introduction efficiency, while operation is convenient and less time is required. In addition, since there is no possibility of the initializing factor being inserted into the genome of the cells in lipofection, there is no need to confirm the presence or absence of insertion of exogenous genes by full genome sequencing of the obtained stem cells. Initializing factor RNA used as a pluripotency inducing factor may include, for example, Oct3/4 mRNA, Sox2 mRNA, Klf4 mRNA, and c-Myc mRNA.

Lipofection of initializing factor RNA uses small interfering RNA (siRNA) or a lipofection reagent, for example. An siRNA lipofection reagent or mRNA lipofection reagent may be used as an RNA lipofection reagent. More specifically, the RNA lipofection reagent used may be Lipofectamine® RNAiMAX (Thermo Fisher Scientific), Lipofectamine® MessengerMAX (Thermo Fisher Scientific), Lipofectamin® 2000, Lipofectamin® 3000, NeonTransfection System (Thermo Fisher scientific), Stemfect RNA transfection reagent (Stemfect), NextFect® RNA Transfection Reagent (BiooSientific), Amaxa® Human T cell Nucleofector® kit (Lonza, VAPA-1002), Amaxa® Human CD34 cell Nucleofector® kit (Lonza, VAPA-1003), or ReproRNA® transfection reagent STEMCELL Technologies).

When the factor introducing device 30 is to introduce an initializing factor into cells by lipofection, the initializing factor RNA and reagents are introduced into the preintroduction cell solution-feeding channel 20 by the inducing factor solution-feeding mechanism 21.

Figure 17:
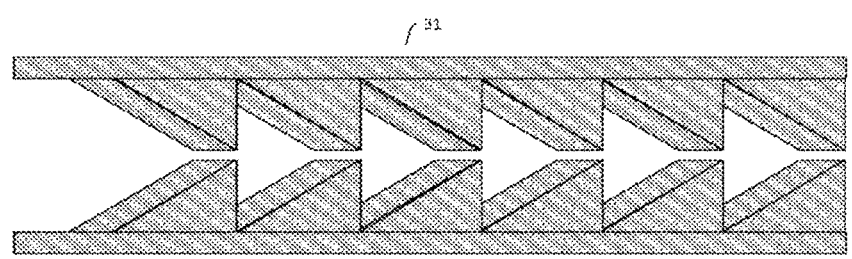
FIG. 17 is a schematic cross-sectional view of an example of an introduced cell solution-feeding channel in a cell processing apparatus according to an embodiment.
Figure 18:
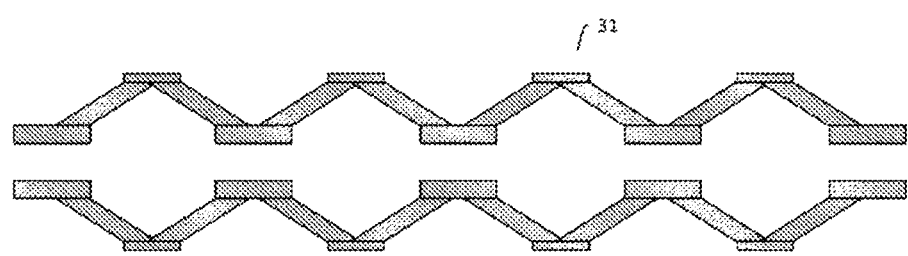
FIG. 18 is a schematic cross-sectional view of an example of an introduced cell solution-feeding channel in a cell processing apparatus according to an embodiment.

The inner wall of the introduced cell solution-feeding channel 31 may be coated with poly-HEMA to render it non-adhesive, so that the cells do not adhere. Alternatively, a material resistant to cell adhesion may be used as the material for the introduced cell solution-feeding channel 31. Also, by using a material with good thermal diffusivity and $CO_2$ permeability as the material for the introduced cell solution-feeding channel 31, the conditions in the introduced cell solution-feeding channel 31 will be equivalent to the controlled temperature and $CO_2$ concentration in the enclosure 601. In addition, a back-flow valve may be provided in the introduced cell solution-feeding channel 31 from the viewpoint of preventing contamination. Numerous cells die after electroporation, and cell masses of dead cells often result. Therefore, a filter may be provided in the introduced cell solution-feeding channel 31 to remove the dead cell masses. Alternatively, as shown in FIG. 17, one or a plurality of folds may be formed in the interior of the introduced cell solution-feeding channel 31 to intermittently vary the inner diameter. As another alternative, the inner diameter of the introduced cell solution-feeding channel 31 may be intermittently varied, as shown in FIG. 18.

As shown in FIG. 16, the cell mass preparation device 40 connected to the introduced cell solution-feeding channel 31 comprises an initializing culturing apparatus 50 that cultures the inducing factor-introduced cells prepared at the factor introducing device 30, a first dissociating mechanism 60 that dissociates the cell masses comprising stem cells (cell colonies) established at the initializing culturing apparatus 50 into a plurality of cell masses, an amplifying culturing apparatus 70 that carries out amplifying culturing of the plurality of cell masses that have been dissociated at the first dissociating mechanism 60, a second dissociating mechanism 80 that dissociates the cell masses comprising stem cells that have been amplifying cultured at the amplifying culturing apparatus 70 into a plurality of cell masses, and a cell mass transport mechanism 90 that delivers the plurality of cell masses in order to the packaging device 100.

The initializing culturing apparatus 50 can house a well plate in its interior. The initializing culturing apparatus 50 also comprises a pipetting machine. The initializing culturing apparatus 50 receives the solution containing the inducing factor-introduced cells from the introduced cell solution-feeding channel 31, and allocates the solution into the wells with the pipetting machine. The initializing culturing apparatus 50 adds stem cell culture medium such as StemFit® (Ajinomoto Co., Inc.) on the 3rd, 5th and 7th days, for example, after allocating the inducing factor-introduced cells to the wells. Basic fibroblast growth factor (basic FGF) may also be added to the culture medium as a supplement. Sustained-release beads, such as StemBeads FGF2 (Funakoshi Corp.), may also be added to the culture medium, for continuous supply of the FGF-2 (basic FGF, bFGF, FGF-b) to the culture medium. Also, since FGF is often unstable, a heparin-like polymer may be conjugated with the FGF to stabilize the FGF. Transforming growth factor beta (TGF-β), activin or the like may also be added to the culture medium. At the initializing culturing apparatus 50, the culture medium is exchanged on the 9th day, for example, after allocating the inducing factor-introduced cells to the wells, and thereafter the culture medium is exchanged every 2 days until the iPS cell masses (colonies) exceed 1 mm Exchange of the medium may be partial exchange of the culture medium, or it may be replenishment.

When cell masses form, the initializing culturing apparatus 50 collects the cell masses with a pipetting machine, and adds a trypsin-substituting recombinant enzyme such as TrypLE Select® (Life Technologies Corp.) to the collected cell masses. In addition, the initializing culturing apparatus 50 places a vessel containing the collected cell masses in an incubator, and reacts the cell masses with the trypsin-substituting recombinant enzyme for 10 minutes at 37° C., 5% $CO_2$. When the cell masses are to be physically disrupted, there is no need for a trypsin-substituting recombinant enzyme. For example, the initializing culturing apparatus 50 disrupts the cell masses by pipetting with a pipetting machine. Alternatively, the initializing culturing apparatus 50 may disrupt the cell masses by passing the cell masses through a pipe provided with a filter, or a pipe that intermittently varies the inner diameter, similar to the introduced cell solution-feeding channel 31 shown in FIG. 17 or FIG. 18. Next, the initializing culturing apparatus 50 adds culture medium for pluripotent stem cells such as StemFit® (Ajinomoto Co., Inc.), to the solution containing the disrupted cell masses.

Culturing in the initializing culturing apparatus 50 may be carried out in a $CO_2$-permeable bag instead of a well plate. The culturing may be by adhesion culture or suspension culture. In the case of suspension culture, agitation culture may be carried out. The culture medium may also be in the form of agar. Agar culture media include gellan gum polymers and deacylated gellan gum polymers. When an agar culture medium is used, there is no settling or adhesion of cells, and therefore agitation is not necessary even though it is suspension culture, and it is possible to form a single cell mass deriving from one cell, while the culturing in the initializing culturing apparatus 50 can also be by hanging drop culture.

The initializing culturing apparatus 50 may also comprise a first culture medium supply device that supplies culture medium including culture solution to a well plate or a $CO_2$-permeable bag. The first culture medium supply device collects the culture solution in the well plate or $CO_2$-permeable bag, and it may use a filter or dialysis membrane to filter the culture solution, to allow reuse of the purified culture solution. During this time, growth factors or the like may be added to the culture solution that is to be reused. Furthermore, the initializing culturing apparatus 50 may also comprise a temperature regulating device that regulates the temperature of the culture medium, and a humidity control device that controls the humidity in the vicinity of the culture medium.

Figure 19:
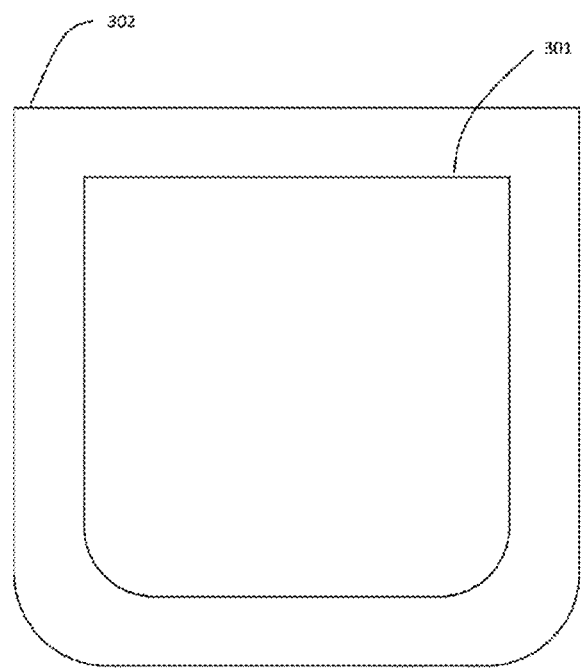
FIG. 19 is a schematic view of a culturing bag to be used in a cell processing apparatus according to an embodiment.

In the initializing culturing apparatus 50, the cells may be placed in a culture solution-permeable bag 301 such as a dialysis membrane as shown in FIG. 19, for example, and the culture solution-permeable bag 301 may be placed in a culture solution-impermeable $CO_2$-permeable bag 302, so that the culture solution is placed in bags 301, 302. The initializing culturing apparatus 50 may have multiple bags 302 prepared containing fresh culture solution, and the bag 302 in which the cell-containing bag 301 is placed may be replaced by a bag 302 containing fresh culture solution, at prescribed intervals of time.

Figure 20:
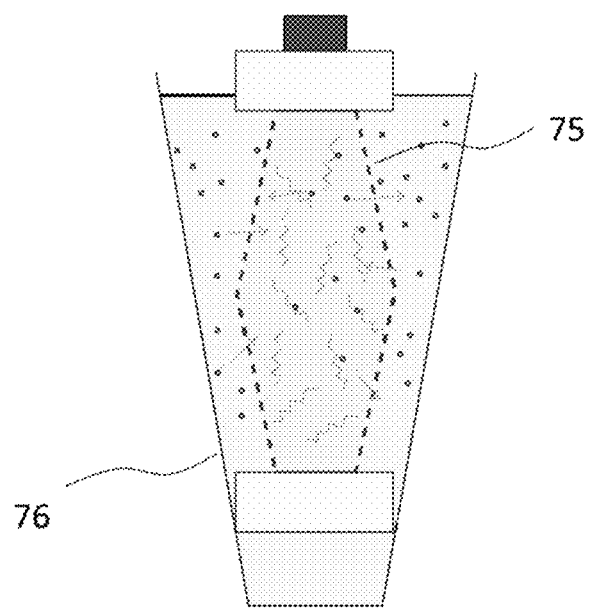
FIG. 20 is a schematic view of a suspension culture vessel according to an embodiment.

The method of culturing in the initializing culturing apparatus 50 is not limited to the method described above, and a suspension culture vessel such as shown in FIG. 20 may be used. The suspension culture vessel shown in FIG. 20 comprises a dialysis tube 75 in which the inducing factor-introduced cells and gel medium are to be inserted, and a vessel 76 in which the dialysis tube 75 is to be placed, with the gel medium accommodable around the periphery of the dialysis tube 75. The suspension culture vessel may also comprise a pH sensor that measures the hydrogen ion exponent (pH) of the gel medium surrounding the dialysis tube 75.

The dialysis tube 75 is made of a semipermeable membrane, and it allows permeation of ROCK inhibitor, for example. The molecular cutoff of the dialysis tube 75 is ≥0.1 KDa, ≥10 KDa, or ≥50 KDa. The dialysis tube 75 is made of, for example, cellulose ester, ethyl cellulose, a cellulose ester derivative, regenerated cellulose, polysulfone, polyacrylnitrile, polymethyl methacrylate, ethylenevinyl alcohol copolymer, polyester-based polymer alloy, polycarbonate, polyamide, cellulose acetate, cellulose diacetate, cellulose triacetate, copper ammonium rayon, saponified cellulose, a Hemophan membrane, a phosphatidylcholine membrane or a vitamin E coated membrane.

The vessel 76 used may be a conical tube such as a centrifugation tube. The vessel 76 is made of polypropylene, for example. The vessel 76 may also be $CO_2$-permeable. G-Rex® (Wilson Wolf) may be used as a $CO_2$-permeable vessel 76.

The inducing factor-introduced cells are placed in the dialysis tube 75. The gel medium is not agitated. Also, the gel medium does not include feeder cells. A solution-feeding channel may be connected to the dialysis tube 75 to feed cell-containing culture medium into the dialysis tube 75. A solution-feeding channel may also be connected to the dialysis tube 75 to feed the cell-containing culture medium in the dialysis tube 75 to the outside of the vessel.

The gel medium is prepared, for example, by adding deacylated gellan gum to the blood cell culture medium or stem cell culture medium, to a final concentration of 0.5 wt % to 0.001 wt %, 0.1 wt % to 0.005 wt % or 0.05 wt % to 0.01 wt %. At the start of initializing culturing, for example, gel medium prepared from the blood cell culture medium is used, and then gel medium prepared from stem cell culture medium is used.

The stem cell culture medium used may be human ES/iPS culture medium such as Primate ES Cell Medium (ReproCELL), for example.

The stem cell culture medium is not limited to this, however, and various stem cell culture media may be used. For example, Primate ES Cell Medium, Reprostem, ReproFF, ReproFF2, ReproXF (Reprocell), mTeSR1, TeSR2, TeSRE8, ReproTeSR (STEMCELL Technologies), PluriSTEM® Human ES/iPS Medium (Merck), NutriStem® XF/FF Culture Medium for Human iPS and ES Cells, Pluriton reprogramming medium (Stemgent), PluriSTEM®, Stemfit AK02N, Stemfit AK03 (Ajinomoto), ESC-Sure® serum and feeder free medium for hESC/iPS (Applied StemCell) and L7® hPSC Culture System (LONZA) may be used.

The gel medium may include one or more high molecular compounds selected from the group consisting of gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts of the foregoing. The gel medium may also include methyl cellulose. Including methyl cellulose allows greater control of aggregation between the cells.

Alternatively, the gel medium may include at least one temperature sensitive gel selected from among poly(glycerol monomethacrylate) (PGMA), poly(2-hydroxypropyl methacrylate) (PHPMA), poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate) and N-isopropylacrylamide.

The gel medium placed in the dialysis tube 75 does not need to include a ROCK inhibitor. The ROCK inhibitor may be added to the gel medium placed around the dialysis tube 75 in the vessel 76, to a final concentration of 1000 µmol/L to 0.1 µmol/L, 100 µmol/L to 1 µmol/L, or 5 µmol/L to 20 µmol/L, for example. By adding a ROCK inhibitor to the gel medium surrounding the dialysis tube 75, the ROCK inhibitor will penetrate into the dialysis tube 75 and colony formation by the cells will be promoted.

The gel medium may either include or not include growth factors such as basic fibroblast growth factor (bFGF) or TGF-β.

During suspension culturing of the cells in the dialysis tube 75, the gel medium surrounding the dialysis tube 75 in the vessel 76 is exchanged. Medium exchange includes partial exchange of the culture medium, as well as replenishment. In this case, the gel medium in the dialysis tube 75 does not need to be supplied. The gel medium may instead be supplied into the dialysis tube 75 during suspension culturing of the cells in the dialysis tube 75. In this case, the gel medium surrounding the dialysis tube 75 in the vessel 76 does not need to be supplied.

Figure 21:
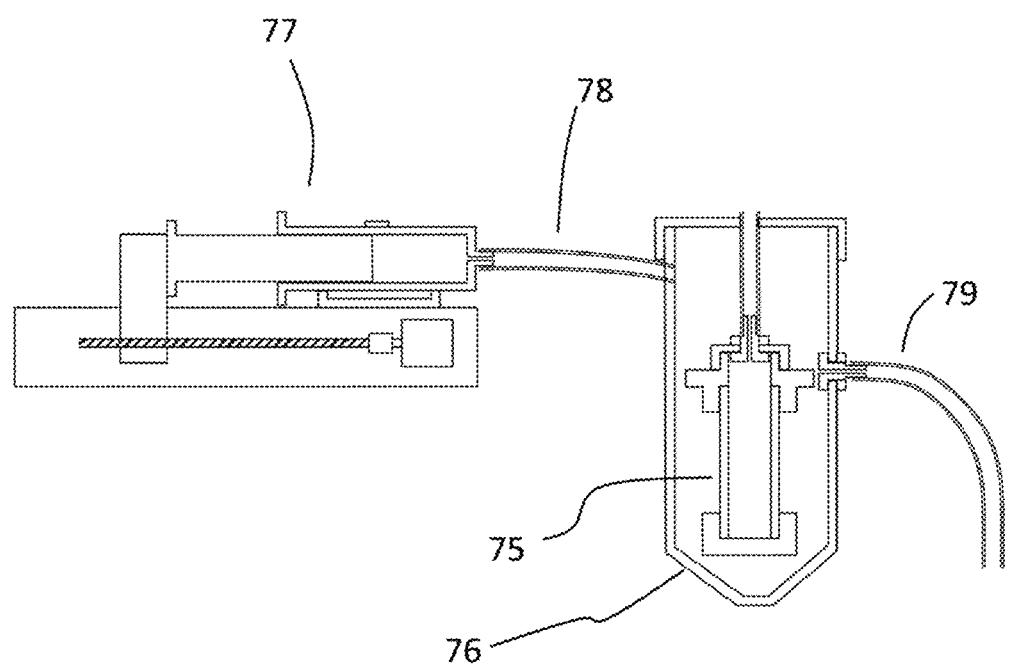
FIG. 21 is a schematic view of a supply culture medium solution-feeding pump and suspension culture vessel according to an embodiment.

As shown in FIG. 21, the cell processing apparatus of this embodiment uses a supply culture medium solution-feeding pump 77 as a culture medium supply device to exchange or supply gel medium surrounding the dialysis tube 75 in the vessel 76. The supply culture medium solution-feeding pump 77 used may be a pump used for drip infusion. The supply culture medium solution-feeding pump 77 and the suspension culture vessel 76 are connected by a solution-feeding tube 78. The supply culture medium solution-feeding pump 77 feeds gel medium into the suspension culture vessel 76 through the solution-feeding tube 78. A waste liquid tube 79 is connected to the suspension culture vessel 76. The gel medium in the suspension culture vessel 76 is discharged through the waste liquid tube 79. The gel medium in the suspension culture vessel 76 may be discharged, for example, by the pressure of fresh gel medium supplied by the supply culture medium solution-feeding pump 77, or it may be discharged utilizing gravity, or it may be discharged by a discharge pump.

The temperature of the gel medium to be delivered from the supply culture medium solution-feeding pump 77 to the culturing vessel is set, for example, so that the temperature of the gel medium in the culturing vessel does not vary drastically. For example, when the temperature of the gel medium in the culturing vessel is 37° C., the temperature of the gel medium delivered to the culturing vessel is set to 37° C. However, the culture medium before it is delivered to the culturing vessel may be set in cold storage at a low temperature of 4° C., for example, at the cold storage unit.

The supply culture medium solution-feeding pump 77 is controlled so that, for example, the amount of the gel medium fed into the suspension culture vessel 76 by the supply culture medium solution-feeding pump 77 and the amount of the gel medium discharged from the suspension culture vessel 76 are equal. The supply culture medium solution-feeding pump 77 may feed the gel medium into the suspension culture vessel 76 constantly, or it may feed the gel medium at appropriate intervals.

When the gel medium is delivered constantly, the flow rate of the gel medium being fed may be either constant or variable. For example, the culture medium and the cell masses in the culture medium may be monitored with a photographing device, as explained below, and the flow rate of the gel medium being fed may be increased or decreased depending on the state of the culture medium and the cell mass in the culture medium.

Also, instead of constant feeding of the gel medium, feeding of the gel medium may be started and stopped depending on the state of the culture medium and the cell masses in the culture medium. In this case as well, the flow rate of the gel medium being fed may be increased or decreased depending on the state of the culture medium and the cell masses in the culture medium.

If the flow rate of the gel medium being fed to the culturing vessel is too high, the cells in the culturing vessel may undergo damage by the pressure of the gel medium. Therefore, the flow rate of the gel medium being delivered to the culturing vessel is set so that the cells do not suffer damage.

When culturing of the cells is to be continued without exchange of the culture medium, accumulation of waste products such as lactic acid discharged by the cells, or variation in pH, can adversely affect the cell culture. In addition, proteins including bFGF or recombinant proteins present in the culture medium may be degraded, resulting in loss of the components necessary for cell culturing.

To counter this, fresh culture medium may be fed to the culturing vessel by the supply culture medium solution-feeding pump 77, and the old culture medium discharged from the culturing vessel, to remove waste products from the culturing vessel, to keep the pH in the culture medium in a suitable range, and to allow supply of the components necessary for culturing of the cells. This will allow the state of the culture medium to be kept nearly constant.

Figure 22:
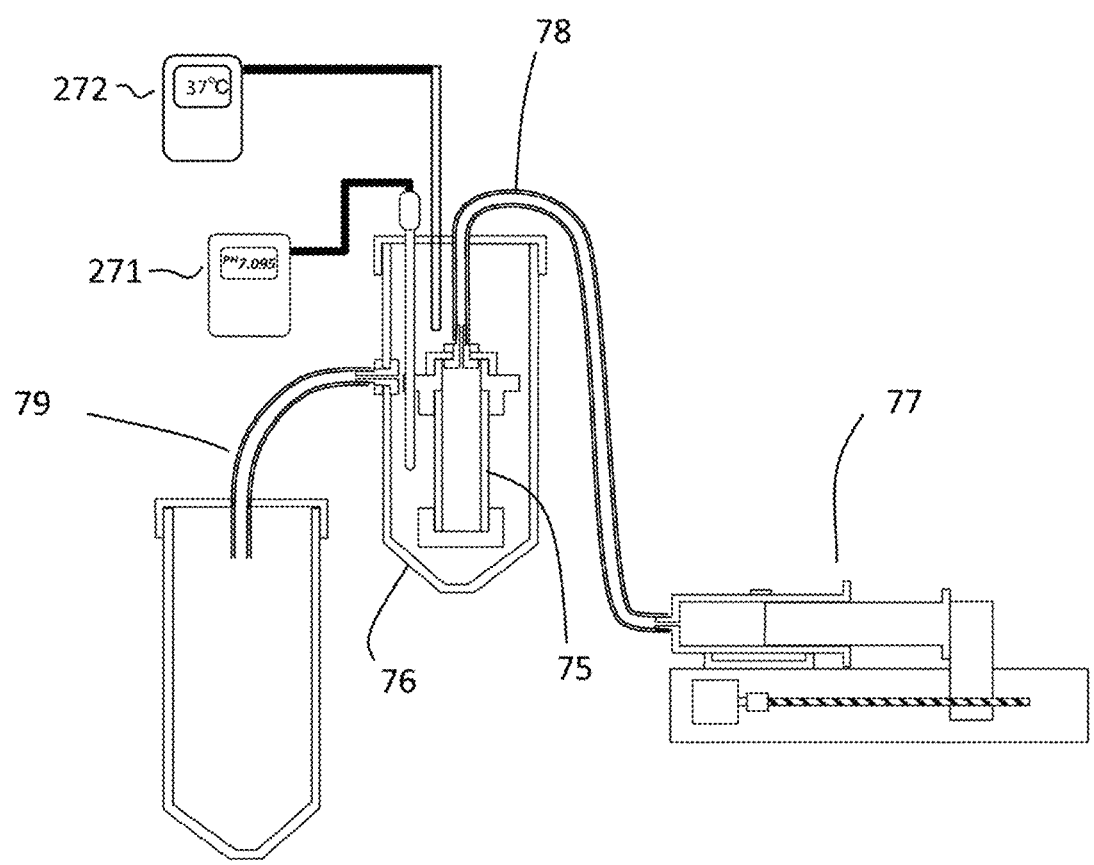
FIG. 22 is a schematic view of a supply culture medium solution-feeding pump and suspension culture vessel according to an embodiment.

FIG. 21 shows an example in which the supply culture medium solution-feeding pump 77 and the suspension culture vessel 76 are connected by the solution-feeding tube 78. Alternatively, as shown in FIG. 22, the supply culture medium solution-feeding pump 77 and the interior of the dialysis tube 75 in the suspension culture vessel 76 may be connected by the solution-feeding tube 78. By feeding fresh gel medium into the dialysis tube 75, waste products present in the culture medium in the dialysis tube 75 are discharged out of the dialysis tube 75. This also allows the pH of the culture medium in the dialysis tube 75 to be kept in a suitable range, and allows the components necessary for culturing of the cells to be supplied to the culture medium in the dialysis tube 75.

The cell processing system may further comprise an initializing culturing photographing device such as a photographing camera or video camera that photographically records culturing in the initializing culturing apparatus 50, as shown in FIG. 16. If a colorless culture medium is used for the culture medium in the initializing culturing apparatus 50, it will be possible to minimize diffuse reflection and autologous fluorescence that may be produced when using a colored culture medium. A pH indicator such as phenol red may be included however, in order to confirm the pH of the culture medium. Moreover, since induced cells and non-induced cells have differences in cellular shape and size, the cell processing system may further comprise an induced state monitoring device that calculates the proportion of induced cells by photographing the cells in the initializing culturing apparatus 50. Alternatively, the induced state monitoring device may determine the proportion of induced cells by antibody immunostaining or RNA extraction. In addition, the cell processing system may comprise a non-induced cell removing device that removes cells that have not been induced, by magnetic-activated cell sorting, flow cytometry or the like.

When the cells are being cultured on a flat dish such as a plate, the region where the cells are present spreads out in a planar manner Thus, if the photographing device and the plate are oriented so that the optical axis of the lens of the photographing device is perpendicular to the dish surface, it will be possible to adjust the focus on essentially all of the cells on the plate.

When the cells are suspended in the culture medium for suspension culture, however, the region where the cells are present will spread out three-dimensionally, and therefore the distance in the optical axis direction from the photographing device to each of the cells will vary. It may therefore be difficult to adjust the focus to all of the cells without using a lens.

However, by using a bright lens (a lens with a low F value) or by imaging with as small an aperture as possible for the lens while illuminating the measuring target with bright lighting, it is possible to increase the depth of the field.

Alternatively, a plurality of images may be taken while gradually varying the focal point of the lens, and the plurality of images synthesized to obtain a pseudo-deep focused image. Each of the plurality of images will be a blend of the focused cells and the blurry non-focused cells. The partial focused images may then be compiled from the plurality of images to produce a single synthetic image.

Figure 23:
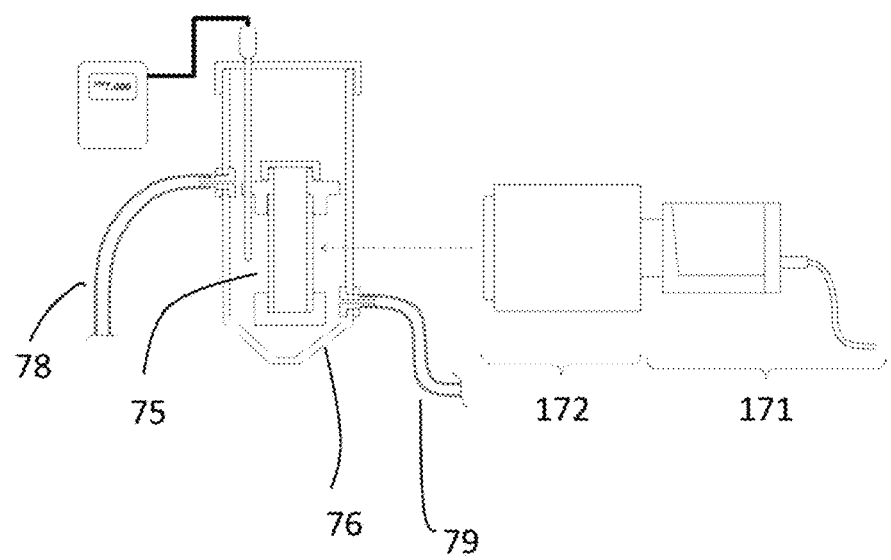
FIG. 23 is a schematic view of a suspension culture vessel and photographing device according to an embodiment.

Alternatively, as shown in FIG. 23, a telecentric lens 172 may be disposed between the initializing culturing photographing device 171 and the object, such as cells, in the suspension culture vessel. With the telecentric lens 172, the principal ray running from the object, such as cells, through the center of the lens aperture is parallel to the lens optical axis, and therefore the sizes of the photographed cells do not vary with distance even if the distances from the initializing culturing photographing device 171 to each of the plurality of cells in the suspension culture vessel are not uniform.

Figure 24:
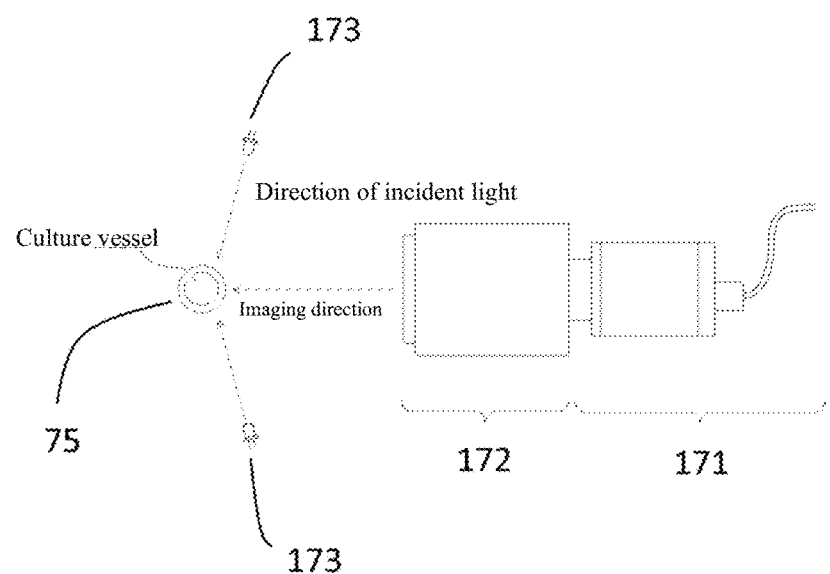
FIG. 24 is a schematic view of a suspension culture vessel and photographing device according to an embodiment.
Figure 25:
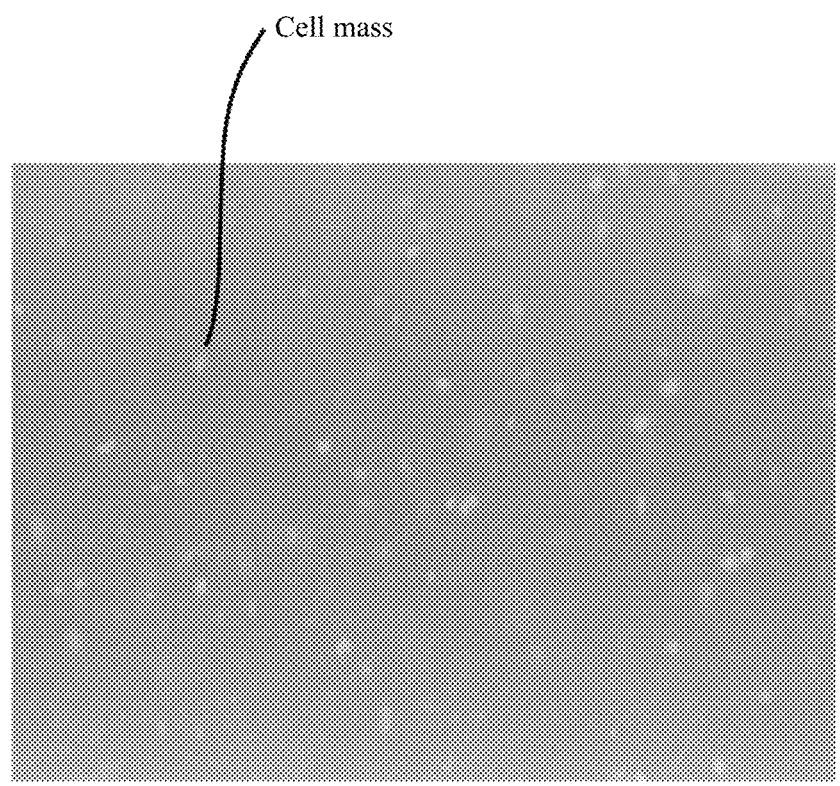
FIG. 25 is an example of an image of cells according to an embodiment.

FIG. 24 is a schematic view of the suspension culture vessel shown in FIG. 23, as seen from above. In FIG. 24, the vessel 76 shown in FIG. 23 is omitted. When cells are to be imaged with the initializing culturing photographing device 171, a scattered light illumination method may be employed, in which a cell observation illumination light source 173 is situated in the direction perpendicular to the optical axis of the initializing culturing photographing device 171, or a direction nearer the photographing device than the perpendicular direction, and illumination light is irradiated on the cells from the cell observation illumination light source 173. Scattered light from the light illuminated on the cells will thus reach the initializing culturing photographing device 171, but the illumination light that has not impacted the cells passes through the culture medium and does not reach the initializing culturing photographing device 171. Thus, the culture medium parts of the image are relatively dark while the cell parts are relatively light. The illumination method is not limited to this method, however, so long as the cells can be recognized in the image. FIG. 25 shows an example of an image of cells taken by a scattered light illumination method. The culture medium parts are relatively dark while the cell parts are relatively light.

Figure 26:
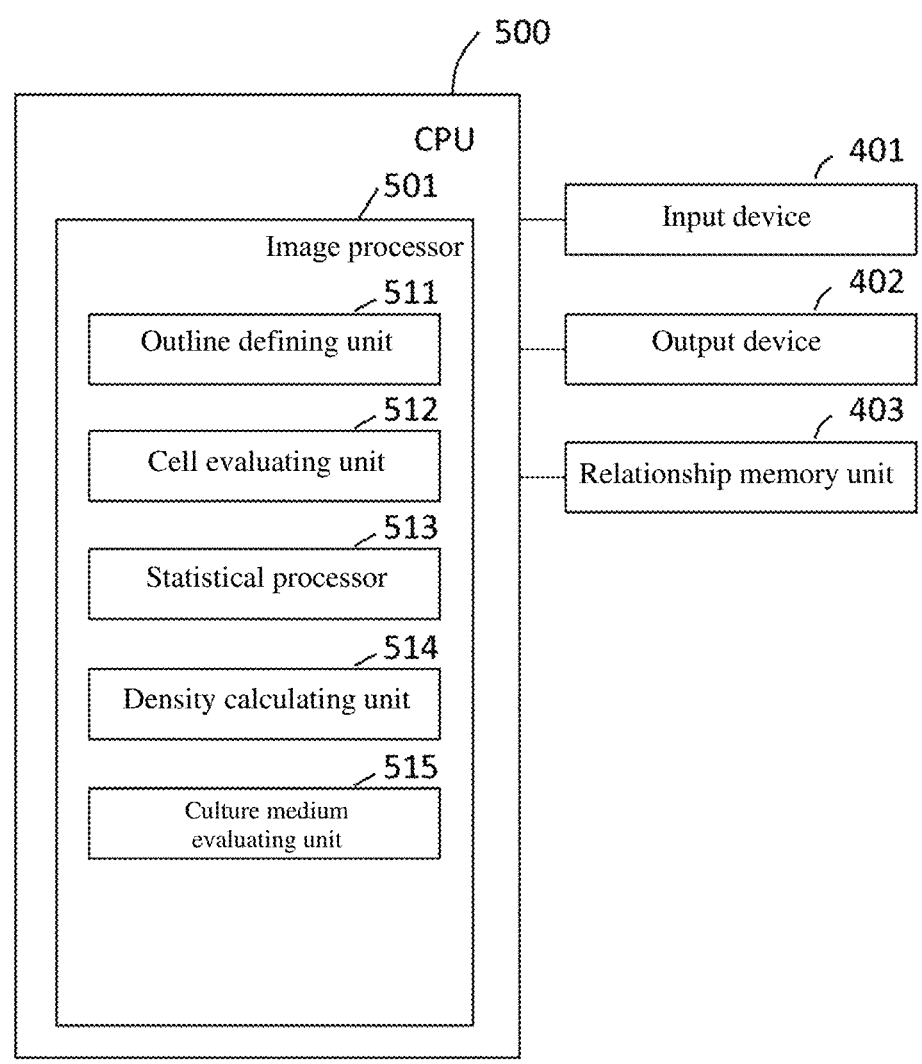
FIG. 26 is a schematic view of a central processing unit according to an embodiment.

As shown in FIG. 26, the cell processing system of this embodiment may also comprise a central processing unit (CPU) 500 provided with an image processor 501 that carries out image processing of the image taken by the initializing culturing photographing device 171. An input device 401 such as a keyboard or mouse and an output device 402 such as a monitor may be connected to the CPU 500. The CPU 500 receives the image from the initializing culturing photographing device 171 via a bus, image interface or the like.

Figure 27:
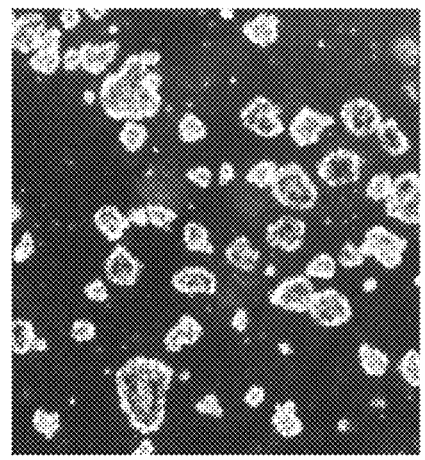
FIG. 27 is an example of an image of cell masses according to an embodiment.

The image processor 501 may also comprise an outline defining unit 511 that defines the outlines of cells or cell masses in the cell image. FIG. 27 is an example of an enlarged image of iPS cell masses taken through a macro zoom lens. In the image shown in FIG. 27, the portions visible as white masses are the iPS cell masses, and the dark background portions are the culture medium.

Figure 28:
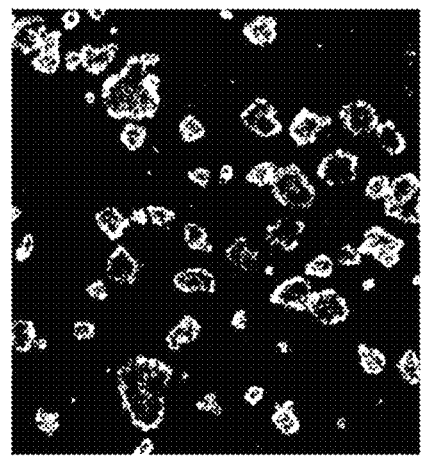
FIG. 28 is an example of a binarized image of cell masses according to an embodiment.

When the image shown in FIG. 27 is an 8-bit grayscale image, and the image is subjected to binarization in which the maximum brightness value of 255, for example, is assigned to the values of the brightness of pixels having brightness values of at least a prescribed threshold value, and the minimum brightness value of 0, for example, is substituted for the values of the brightness of pixels having brightness values less than the prescribed threshold value, then not only the culture medium portions but also the interiors of the cell masses appear as the minimum brightness of black, as shown in FIG. 28, and contiguous portions appear between the interiors of the cell masses and the culture medium portions. Therefore, it may not be possible to extract the cells or cell masses with binarization.

Figure 29:
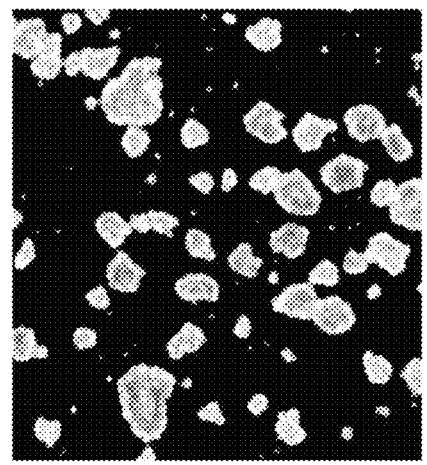
FIG. 29 is an example of an image of cell masses to which a highpass filter has been applied, according to an embodiment.

However, the outline defining unit 511 of the cell processing system according to the embodiment shown in FIG. 26 applies a highpass filter which allows passage of high-frequency components of at least a prescribed frequency in the spatial frequency while blocking low-frequency components of less than the prescribed frequency in the image of the cells, with a brightness value of 0, for example, as the minimum value. Numerous high-frequency components in the spatial frequency are present in the cell or cell mass portions of the cell image, while few high-frequency components in the spatial frequency are present in the culture medium portions. Consequently, in a cell image subjected to a highpass filter as shown in FIG. 29, the brightness values of the culture medium portions are the minimum value of 0, for example, while the cell or cell mass portions retain their brightness values. Therefore, the portions that are not at the minimum value of brightness may be considered to be the cells or cell masses.

In the image shown in FIG. 29, the portions where the brightness was not the minimum value appear as blobs, and even with detection by blob analysis, two mutually adjacent cell masses, for example, may appear to be a single cell mass in some cases.

Therefore, the outline defining unit 511 of the cell processing system of the embodiment shown in FIG. 26 applies a watershed algorithm to the image that was subjected to the highpass filter. A watershed algorithm considers the brightness gradient in the image as mountainous corrugations, and divides the image so that zones formed by water flowing from the high locations of the mountains (the locations of high brightness) to the low locations (the locations of low brightness) are a single region.

Figure 30:
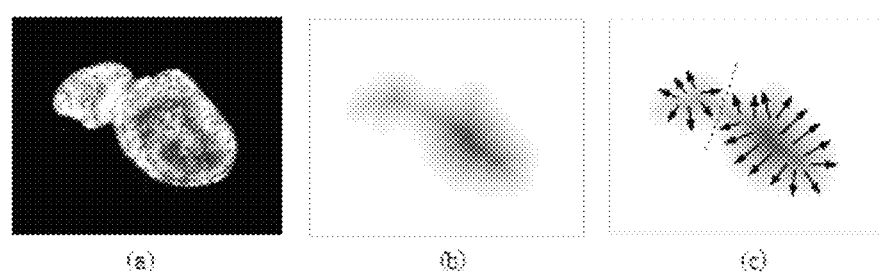
FIG. 30 is an example of images of cell masses to which a watershed algorithm has been applied, according to an embodiment.

For example, the outline defining unit 511 of the cell processing system of this embodiment converts the image by the distance transform method before applying the watershed algorithm to the image. The distance transform method is an image transforming method in which the value of the brightness of each pixel of an image is substituted based on the distance to the nearest background pixel. For example, in an image that has been subjected to a highpass filter, as shown in FIG. 30(*a*), the brightness value in the culture medium region is converted to 255 as the maximum brightness value, to produce a white background as shown in FIG. 30(*b*). Also, the value of the brightness of each pixel in the cell region is converted in a range of 0 up to less than 255, based on the distance to the nearest background pixel. For example, the brightness value is lowered the further it is from the nearest background pixel.

Next, the outline defining unit 511 of the cell processing system of this embodiment applies a watershed algorithm to the image that has been transformed by the distance transform method. In the image shown in FIG. 30(*b*), with the dark portions of low brightness being considered to be the mountain ridges, it is imagined how water that has been poured on the image from the perpendicular direction will flow, as indicated by the arrows in FIG. 30(*c*), and considering the valley to be the location where water flowing from different directions impacts, as indicated by the broken line in FIG. 30(*c*), the cell region is divided at the bottom of the valley.

Figure 31:
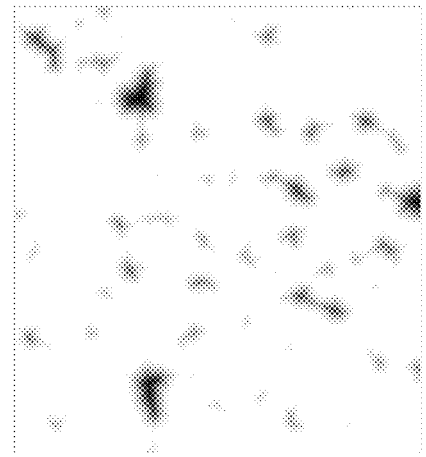
FIG. 31 is an example of an image of cell masses to which a distance transform method has been applied, according to an embodiment.
Figure 32:
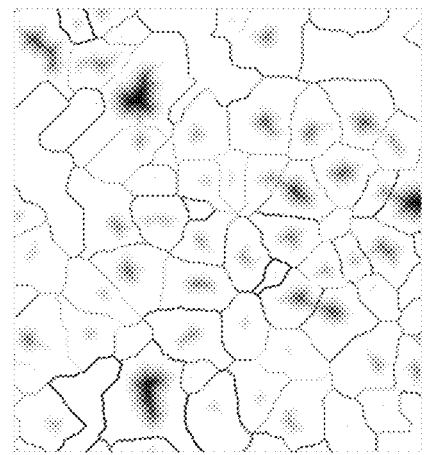
FIG. 32 is an example of images of cell masses to which a watershed algorithm has been applied, according to an embodiment.
Figure 33:
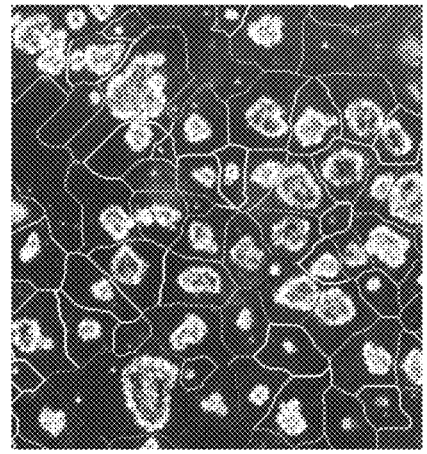
FIG. 33 is an example of an image of cell masses dissociated into multiple regions, according to an embodiment.
Figure 34:
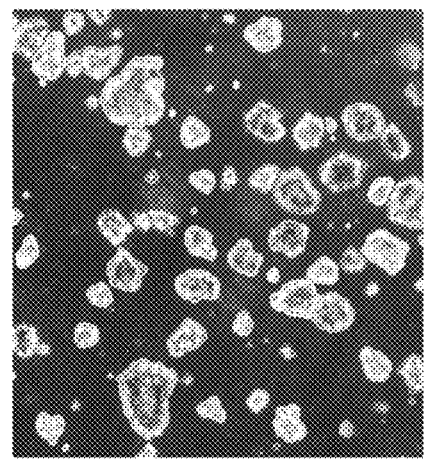
FIG. 34 is an example of an image of cell masses from which the outlines have been extracted, according to an embodiment.

When the pixels in the cell region of the image shown in FIG. 29 are transformed by the distance transform method, the image shown in FIG. 31 is obtained. When a watershed algorithm is applied to the image shown in FIG. 31, the image shown in FIG. 32 is obtained. When the obtained dividing lines are layered over the original image shown in FIG. 27, the image shown in FIG. 33 is obtained. In FIG. 33, the cell masses present in each region divided by the dividing lines are not masses in which a plurality of cell masses are adjacent, but instead they may be considered to be single cell masses. In each region, therefore, the outlines of the cell masses can be extracted to allow accurate extraction of single cell masses, as shown in FIG. 34.

The image processor 501 of the cell processing system of the embodiment shown in FIG. 26 may further comprise a cell evaluating unit 512. The cell evaluating unit 512 evaluates the cell mass size, etc. of each cell mass extracted by the outline defining unit 511. For example, the cell evaluating unit 512 calculates the area of a single cell mass extracted by the outline defining unit 511. When the shape of the single cell mass is considered to be circular, for example, the cell evaluating unit 512 also calculates the diameter of the single cell mass from the area, using the following formula (1).

$$D=2(s/\pi)^{1/2} \quad (1)$$

Here, D represents the diameter and S represents the area.

If the cell mass grows too large, the nutrients and hormones in the culture medium may fail to reach the interior and the cells may differentiate. In addition, if cell masses that are too small are transferred to amplifying culture without using a ROCK inhibitor, cell death or karyotypic abnormalities may occur. Consequently, the cell evaluating unit 512 may emit an alert when the individual cell mass sizes are outside of the suitable range. In addition, the cell evaluating unit 512 may output a timing for transfer to amplifying culture when the individual cell mass sizes are beyond a prescribed threshold value. The supply rate of culture medium at the initializing culturing apparatus 50 may also be varied according to the calculated cell mass sizes. For example, the supply rate of the culture medium may be increased as the cell mass sizes increase.

Figure 35:
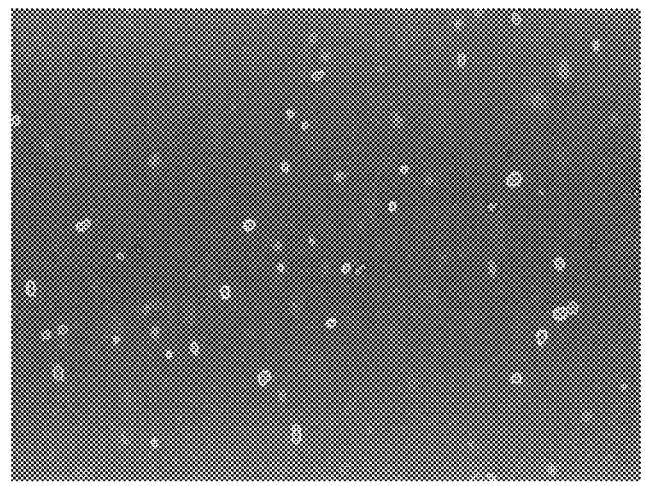
FIG. 35 is an example of an image of cell masses from which the outlines have been extracted, according to an embodiment.
Figure 36:
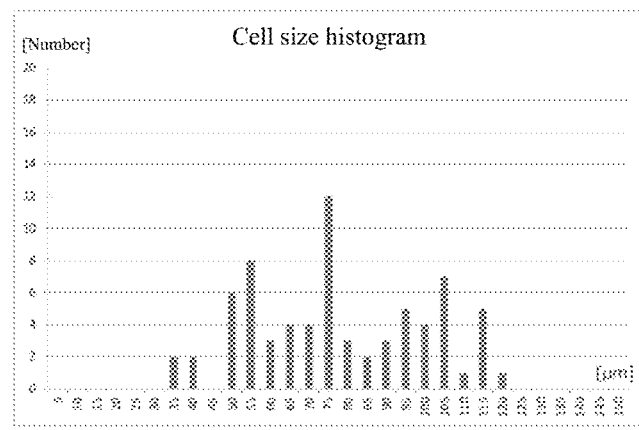
FIG. 36 is an example of a size histogram for cells according to an embodiment.

The image processor 501 of the cell processing system of this embodiment may further comprise a statistical processor 513 that statistically processes data obtained from the image that has undergone image processing. FIG. 35 is an example of image processing of the image shown in FIG. 25, with the cell mass portions extracted and outlined. FIG. 36 is an example of a histogram of cell mass sizes, drawn based on the image shown in FIG. 35. By thus continuously and periodically obtaining cell data, it is possible to quantitatively ascertain the degree of growth, number and compactness of the cell masses, allowing the results of culturing to be stabilized. The supply rate of culture medium at the initializing culturing apparatus 50 may also be varied according to the calculated number of cell masses. For example, the supply rate of the culture medium may be increased as the number of cell masses increases.

The image processor 501 of the cell processing system according to the embodiment shown in FIG. 26 may further comprise a density calculating unit 514 that calculates the turbidity of the culture medium from the image of the culture medium and calculates the cell mass density in the culture medium based on the turbidity of the culture medium.

For example, a relationship memory unit 403 comprising a volatile memory or a non-volatile memory may be connected to the CPU 500. The relationship memory unit 403 stores, for example, the relationship between the turbidity of the culture medium and the cell mass density in the culture medium, that have been previously obtained. The density calculating unit 514 reads out the relationship between turbidity and density from the relationship memory unit 403. The density calculating unit 514 also calculates the density of cell masses in the culture medium, based on the value of the turbidity of the culture medium that has been calculated from the image of the culture medium, and the relationship between turbidity and density. This allows the cell mass density to be measured in a non-destructive manner without harvesting the cell masses from the culture medium.

The density calculating unit 514 may also output a timing for transfer to the amplifying culturing, when the cell mass density has reached at least at prescribed threshold value. In addition, the density calculating unit 514 may calculate the cell mass density in the culture medium with passing time, and may calculate the growth rate of the cell masses. An abnormal growth rate may indicate abnormalities in the cells. For example, the density calculating unit 514 emits an alert when an abnormal growth rate has been calculated. Culturing of the cells may be interrupted when this occurs.

If the cell mass density in the culture medium is high and the distance between cell masses is too close, a plurality of cell masses may adhere together to form a single large cell mass. In a large cell mass, the nutrients and hormones in the culture medium may fail to reach the interior and the cells within it may differentiate. On the other hand, if the cell mass density in the culture medium is lower than the preferred range, the cell mass growth rate and cell mass formability may be significantly reduced.

However, since the cell mass density can be calculated by the density calculating unit 514, it is possible to easily determine whether or not the cell mass density is within the preferred range. When the cell mass density has become lower than the preferred range, a judgment may be made to interrupt the culturing, for example. Furthermore, the supply rate of culture medium at the initializing culturing apparatus 50 may be varied according to the calculated cell mass density. For example, the supply rate of the culture medium may be increased as the cell mass density increases.

Figure 37:
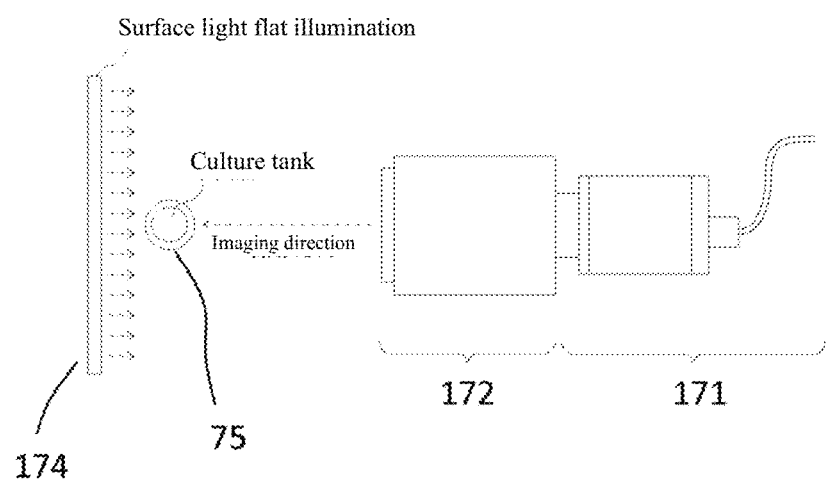
FIG. 37 is a schematic view of a suspension culture vessel and photographing device according to an embodiment.

In addition, in order to observe variation in the culture medium color that takes place with cell metabolism, a culture medium observation illumination light source 174 may be situated at a location facing the initializing culturing photographing device 171 and sandwiching the suspension culture vessel, as shown in FIG. 37. A surface light source, for example, may be used as the medium observation illumination light source 174, with the medium observation illumination light source 174 emitting white parallel rays, for example. The illumination light emitted from the medium observation illumination light source 174 passes through the culture medium and impinges on the initializing culturing photographing device 171, thereby allowing the culture medium color to be imaged by the initializing culturing photographing device 171.

Cell culturing is generally carried out with a constant culture medium pH near 6.8 to 7.2. When the culture medium pH is to be measured, a pH reagent such as phenol red is added to the culture medium. Phenol red changes due to the pH of the culture medium. When the carbon dioxide concentration of the gas contacting the culture medium is insufficient, carbon dioxide in the air does not equilibrate with carbon dioxide from bicarbonate in the culture medium, and therefore the culture medium becomes alkaline and the culture medium color turns reddish violet. Also, with accumulation of waste products consisting mainly of lactic acid discharged by the cells, the culture medium becomes acidic and the culture medium color turns yellow. Acidity of the culture medium indicates that the nutrients in the culture medium have been depleted.

The image processor 501 of the cell processing system according to the embodiment shown in FIG. 26 may further comprise a culture medium evaluating unit 515 that evaluates the culture medium based on the image of the culture medium illuminated by the medium observation illumination light source. The culture medium evaluating unit 515 performs image processing of the culture medium image, for example, and expresses the color of the culture medium as the three parameters HSV: Hue, chroma (Saturation) and brightness (Value). Of these, hue is a parameter corresponding to a concept commonly referred to as "color shade" or "tint". Hue is commonly represented as angle units.

Figure 38:
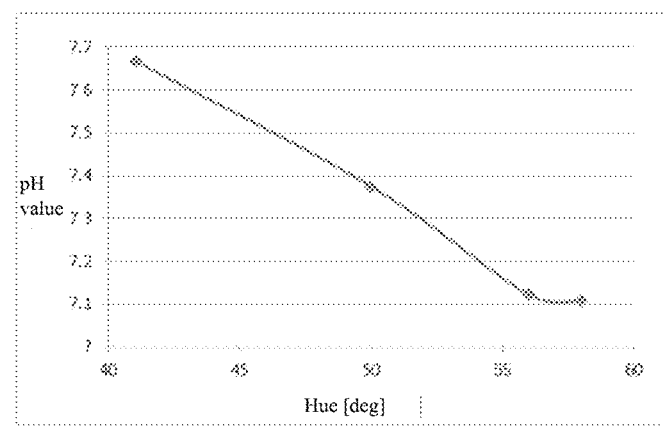
FIG. 38 is an example of a graph showing the relationship between culture medium pH and culture medium hue, according to an embodiment.

FIG. 38 is an example of a graph showing the relationship between change in culture medium hue and change in culture medium pH, during long-term culturing of cells without exchange of the medium. Immediately after the start of culturing, the culture medium pH was near 7.7, but the culture medium pH decreased to near 7.1 as time progressed. At the same time, the culture medium hue was near 40 immediately after the start of culturing, but increased to nearly 60 as time progressed. Thus, culture medium hue is correlated with culturing time and culture medium pH. Therefore, the culture medium evaluating unit 515 shown in FIG. 26 judges the state of the culture medium by monitoring the hue of the culture medium.

The relationship memory unit 403 stores, for example, the relationship between the hue of the culture medium and the pH of the culture medium, that have been previously obtained. The culture medium evaluating unit 515 reads out the relationship between hue and pH from the relationship memory unit 403. The culture medium evaluating unit 515 also calculates the pH value of the photographed culture medium based on the value of the hue of the culture medium that has been calculated from the culture medium image, and the relationship between hue and pH. For example, the culture medium evaluating unit 515 may obtain an image of the culture medium over time and calculate the value of the pH of the culture medium.

Incidentally, the culture medium pH may also be measured with a pH sensor 271, as shown in FIG. 22. The culture medium temperature may also be measured with a thermometer 272. In this case, the culture medium evaluating unit 515 may receive the value of the culture medium pH from the pH sensor 271, and may receive the value of the culture medium temperature from the thermometer 272.

When the culture medium hue or the culture medium pH is outside of the prescribed ranges, the culture medium evaluating unit 515 judges that exchange of culture medium should be accelerated, or that contamination has occurred in the culture medium. Medium exchange includes partial exchange of the culture medium, as well as replenishment.

Chemical analysis of culture medium components is costly, and when the culture medium is taken out of the system for chemical analysis of the culture medium, there is a risk that the aseptic state of the culture medium may not be maintained. In contrast, monitoring the state of a culture medium by monitoring the culture medium hue has low cost and does not affect the aseptic state of the culture medium.

When the culture medium evaluating unit 515 has judged that the culture medium hue or culture medium pH is outside of the prescribed range, the culture medium surrounding the dialysis tube 75 of the suspension culture vessel is exchanged by the supply culture medium solution-feeding pump 77 shown in FIG. 21, for example. Alternatively, when the culture medium is being constantly exchanged, the exchange rate of the culture medium surrounding the dialysis tube 75 of the suspension culture vessel by the supply culture medium solution-feeding pump 77 increases, and the flow rate of the exchanged culture medium increases. This allows the culture medium pH to be maintained within a range suitable for cell culturing, and allows sufficient nutrients to be supplied to the culture medium.

In addition, the culture medium evaluating unit 515 may calculate the growth rate of the cells from the rate of change of the culture medium hue. The relationship memory unit 403 stores, for example, the relationship between the rate of change in the culture medium hue and the growth rate of the cells, that have been previously obtained. The culture medium evaluating unit 515 reads out the relationship between the hue change rate and the growth rate, from the relationship memory unit 403. In addition, the culture medium evaluating unit 515 calculates the value for the growth rate of the cells, based on the calculated value of the hue change rate and the relationship between the hue change rate and the growth rate.

When the culture medium evaluating unit 515 has judged that the temperature of the culture medium is outside of the prescribed range, it may control a temperature regulating device so as to change the temperature surrounding the culturing vessel, or the temperature of the supplied culture medium. For example, when the temperature of the culture medium is lower than the prescribed range, the culture medium evaluating unit 515 regulates the temperature regulating device so that the temperature of the culture medium rises. When the temperature of the culture medium is higher than the prescribed range, the culture medium evaluating unit 515 regulates the temperature regulating device so that the temperature of the culture medium falls.

A first cell mass solution-feeding channel 51 is connected to the initializing culturing apparatus 50 shown in FIG. 16. The initializing culturing apparatus 50 employs a pump or the like to deliver a solution containing trypsin-substituting recombinant enzyme and the cell masses to the first cell mass solution-feeding channel 51. When the cell masses are to be physically disrupted, there is no need for a trypsin-substituting recombinant enzyme. Also, the first cell mass solution-feeding channel 51 may have an inner diameter that allows passage of only induced cells of less than a prescribed size, and it may be connected to a branched fluid channel that removes non-induced cells of a prescribed size or larger. As mentioned above, when a gel medium is used, the cell masses can be collected by suctioning up the gel medium.

The pump that delivers the cell mass-containing solution to the first cell mass solution-feeding channel 51 may be driven when, for example, the value of the cell mass size calculated by the cell evaluating unit 512 shown in FIG. 26 is at least a prescribed threshold value. Alternatively, the pump that delivers the cell mass-containing solution to the first cell mass solution-feeding channel 51 shown in FIG. 16 may be driven when, for example, the value of the cell mass density calculated by the density calculating unit 514 shown in FIG. 26 is at least a prescribed threshold value.

The inner wall of the first cell mass solution-feeding channel 51 shown in FIG. 16 may be coated with polyHEMA to render it non-cell-adherent, so that the cells do not adhere. Alternatively, a material resistant to cell adhesion may be used as the material for the first cell mass solution-feeding channel 51. In addition, if a material with good thermal diffusivity and $CO_2$ permeability is used as the material for the first cell mass solution-feeding channel 51, the conditions in the first cell mass solution-feeding channel 51 will be equivalent to the controlled temperature and $CO_2$ concentration in the enclosure 601. A back-flow valve may also be provided in the first cell mass solution-feeding channel 51 from the viewpoint of preventing contamination.

The first cell mass solution-feeding channel 51 is connected to the first dissociating mechanism 60. The first dissociating mechanism 60 comprises a mesh, for example. The cell masses in the solution are dissociated into a plurality of cell masses corresponding to the sizes of the holes of the mesh, when they pass through the mesh by water pressure. If the mesh hole sizes are uniform, for example, the sizes of the plurality of cell masses after being dissociated will be approximately uniform. Alternatively, the first dissociating mechanism 60 may comprise a nozzle. For example, if the interior of an approximately conical nozzle is micromachined in a step-wise manner, a cell mass in the solution will be dissociated into a plurality of cell masses when it passes through the nozzle.

Figure 39:
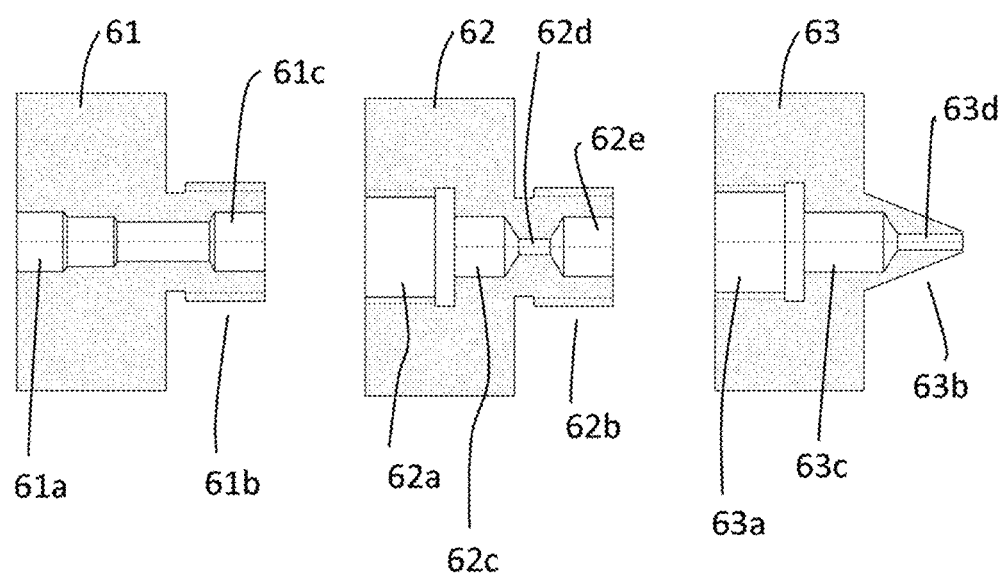
FIG. 39 is a schematic view of a cell mass dissociater according to an embodiment.
Figure 40:
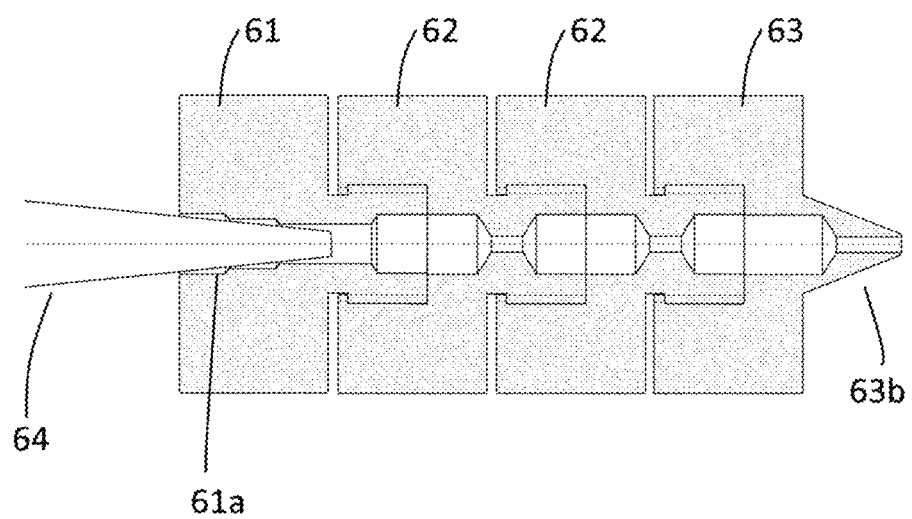
FIG. 40 is a schematic view of a cell mass dissociater according to an embodiment.
Figure 41:
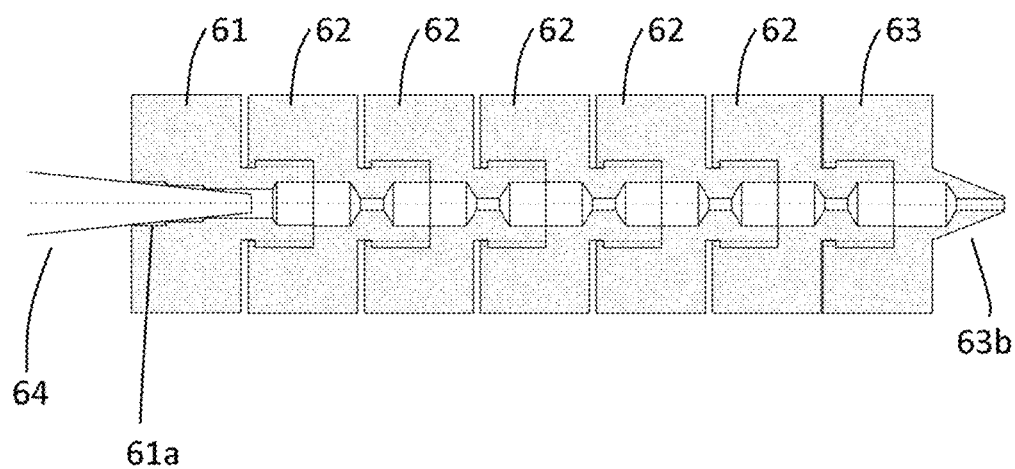
FIG. 41 is a schematic view of a cell mass dissociater according to an embodiment.

As another alternative, shown in FIG. 39, the first dissociating mechanism 60 may comprise a cell mass dissociater comprising a terminal block 61, a connecting block 62 and a tip block 63. The terminal block 61, connecting block 62 and tip block 63 are each provided with a through-hole inside them through which the cell mass-containing culture medium flows. As shown in FIG. 40 and FIG. 41, the terminal block 61, connecting block 62 and tip block 63 are connected. The cell mass dissociater may comprise a single connecting block 62, or it may comprise a plurality of connecting blocks 62.

As shown in FIG. 39, at the first edge of the connecting block 62 there is provided a recess 62*a*, and at the second edge opposite the first edge of the connecting block 62 there is provided a protrusion 62*b*. The protrusion 62*b* is cylindrical, for example. As shown in FIG. 40 and FIG. 41, when a plurality of connecting blocks 62 are used, the protrusions 62*b* engage with the recesses 62*a* of the adjacent connecting blocks 62. The side wall of the protrusion 62*b* shown in FIG. 39 may be smooth, or a male screw form may be provided. The inner wall of the recess 62*a* may be smooth, or a female screw form may be provided.

The through-hole provided in the connecting block 62 has a first large pore size section 62*c* that communicates with the recess 62*a*, a small pore size section 62*d* that communicates with the first large pore size section 62*c* and has a smaller pore size than the first large pore size section 62*c*, and a second large pore size section 62*e* that communicates with the small pore size section 62*d*, has a larger pore size than the small pore size section 62*d*, and has an opening at the tip of the protrusion 62*b*.

The cross-sectional shapes of the first large pore size section 62*c*, small pore size section 62*d* and second large pore size section 62*e* are circular, for example. The pore size of the first large pore size section 62*c* and the pore size of the second large pore size section 62*e* are the same, for example. Thus, when a plurality of connecting blocks 62 are used and the plurality of connecting blocks 62 are connected, as shown in FIG. 40 and FIG. 41, the second large pore size section 62*e* will smoothly communicate with the first large pore size section 62*c* of the adjacent connecting block 62.

The pore sizes of the first and second large pore size sections 62*c*, 62*e* shown in FIG. 39 are, for example, between 2.0 mm and 4.0 mm, inclusive, without any particular restriction to this range. The pore size of the small pore size section 62*d* is, for example, between 0.4 mm and 1.2 mm, inclusive, without any particular restriction to this range. A step is formed at the section connecting from the first large pore size section 62*c* to the small pore size section 62*d*. A step is also formed at the section connecting from the small pore size section 62*d* to the second large pore size section 62*e*. The side walls of the steps may be perpendicular to the central axis of the through-hole, or they may be inclined at less than 90°.

Figure 42:
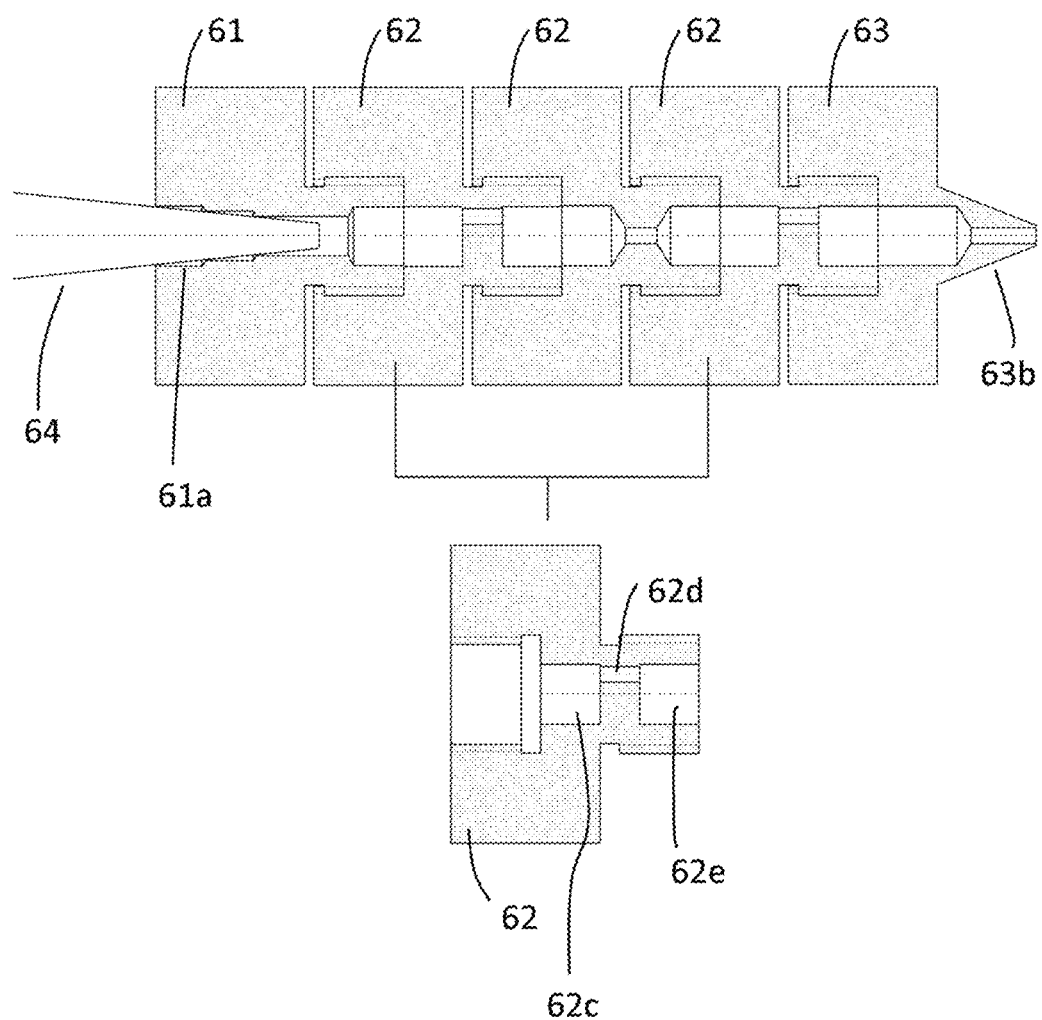
FIG. 42 is a schematic view of a cell mass dissociater according to an embodiment.

The central axes of the first and second large pore size sections 62*c*, 62*e* and the central axis of the small pore size section 62*d* in the connecting block 62 may match. Alternatively, the central axes of the first and second large pore size sections 62*c*, 62*e* and the central axis of the small pore size section 62*d* in the connecting block 62 may be offset, as shown in FIG. 42.

A recess 63*a* is provided at the first edge of the tip block 63 shown in FIG. 39, and a nozzle section 63*b* is provided at the second edge opposite the first edge of the tip block 63. When the tip block 63 and the connecting block 62 are connected, the recess 63*a* of the tip block 63 engages with the protrusion 62*b* of the connecting block 62. The inner wall of the recess 63*a* may be smooth, or a female screw form may be provided.

The through-hole provided in the tip block 63 has a large pore size section 63*c* that communicates with the recess 63*a*, and a small pore size section 63*d* that communicates with the large pore size section 63*c*, has a smaller pore size than the large pore size section 63*c*, and has an opening at the tip of the nozzle section 63*b*.

The cross-sectional shapes of the large pore size section 63*c* and the small pore size section 63*d* are circular, for example. The pore size of the large pore size section 63*c* of the tip block 63 and the pore size of the second large pore size section 62*e* of the connecting block 62 are the same, for example. This will allow the second large pore size section 62*e* of the connecting block 62 and the large pore size section 63*c* of the adjacent tip block 63 to smoothly communicate when the connecting block 62 and the tip block 63 have been connected, as shown in FIG. 40 and FIG. 41.

The pore size of the large pore size section 63*c* shown in FIG. 39 is, for example, between 2.0 mm and 4.0 mm, inclusive, without any particular restriction to this range. The pore size of the small pore size section 63*d* is, for example, between 0.4 mm and 1.2 mm, inclusive, without any particular restriction to this range. A step is formed at the section connecting from the large pore size section 63*c* to the small pore size section 63*d*. The side walls of the steps may be perpendicular to the central axis of the through-hole, or they may be inclined at less than 90°.

A recess 61*a* is provided at the first edge of the terminal block 61, and a protrusion 61*b* is provided at the second edge opposite the first edge of the terminal block 61. When the terminal block 61 and the connecting block 62 are connected, the protrusion 61*b* of the terminal block engages with the recess 62*a* of the connecting block 62. The side wall of the protrusion 61*b* of the terminal block may be smooth, or a male screw may be provided.

The through-hole provided in the terminal block 61 has at least a large pore size section 61*c* that communicates with the recess 61*a* and has an opening at the tip of the protrusion 61*b*.

The cross-sectional shapes of the recess 61*a* and the large pore size section 61*c* are circular, for example. The pore size of the large pore size section 61*c* of the terminal block 61 and the pore size of the second large pore size section 62*e* of the connecting block 62 are the same, for example. This will allow the large pore size section 61*c* of the terminal block 61 and the large pore size section 62*c* of the adjacent connecting block 62 to smoothly communicate when the terminal block 61 and the connecting block 62 have been connected, as shown in FIG. 40 and FIG. 41.

The pore size of the large pore size section 61*c* shown in FIG. 39 is, for example, between 2.0 mm and 4.0 mm, inclusive, without any particular restriction to this range.

The materials of the terminal block 61, the connecting block 62 and the tip block 63 may be, but are not restricted to, resins such as polypropylene.

As shown in FIG. 40, FIG. 41 and FIG. 42, an insertion nozzle 64, for example, is inserted in the recess 61a of the terminal block 61. A suction drainer that suction drains the cell mass-containing culture medium, either directly or through a tube or the like, is connected to the insertion nozzle 64. When the terminal block 61, connecting block 62 and tip block 63 are connected, the nozzle section 63b of the tip block 63 is thrust into the cell mass-containing culture medium, and the suction drainer carries out suction drainage of the culture medium once or repeats suction drainage of the culture medium, the cell mass-containing culture medium is reciprocated in the through-holes in the connecting block 62 and the tip block 63. Because steps are provided in the through-holes of the connecting block 62 and tip block 63, the cell masses in the culture medium are dissociated into small cell masses in an efficient manner.

Figure 47:
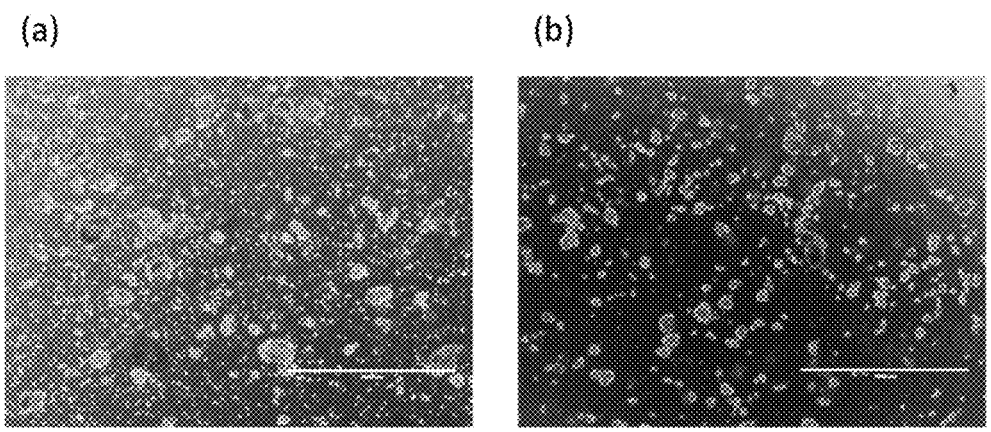
FIG. 47 is an example of an image of dissociated cell masses according to an embodiment.

Conventionally, dissociation of cell masses has been carried out by a technician using a Pipetman or the like. However, as shown in FIG. 47(*a*), cell mass sizes dissociated by the conventional method have been non-uniform. Moreover, the obtained cell mass sizes have been variable depending on the technician. If the dissociated cell masses are too large, the nutrients and hormones in the culture medium may fail to reach the interior and the cells may differentiate. If the cell masses are too small and a ROCK inhibitor is not used, cell death or karyotypic abnormalities may occur. By using the cell mass dissociater illustrated in FIG. 40, FIG. 41 and FIG. 42, however, it is possible to dissociate cell masses into cell masses of uniform sizes, as shown in FIG. 47(*b*). When the cell mass dissociater is used to dissociate cell masses, the culture medium may include enzymes such as trypsin, or TrypLE Express® (Thermo Fisher Scientific), TrypLE Select® (Thermo Fisher Scientific) or TrypLE Select® (Thermo Fisher Scientific). Also, by increasing the number of connecting blocks 62 or raising the pressure during suction drainage of the culture medium, it is possible to degrade the cell masses into single cells.

Figure 43:
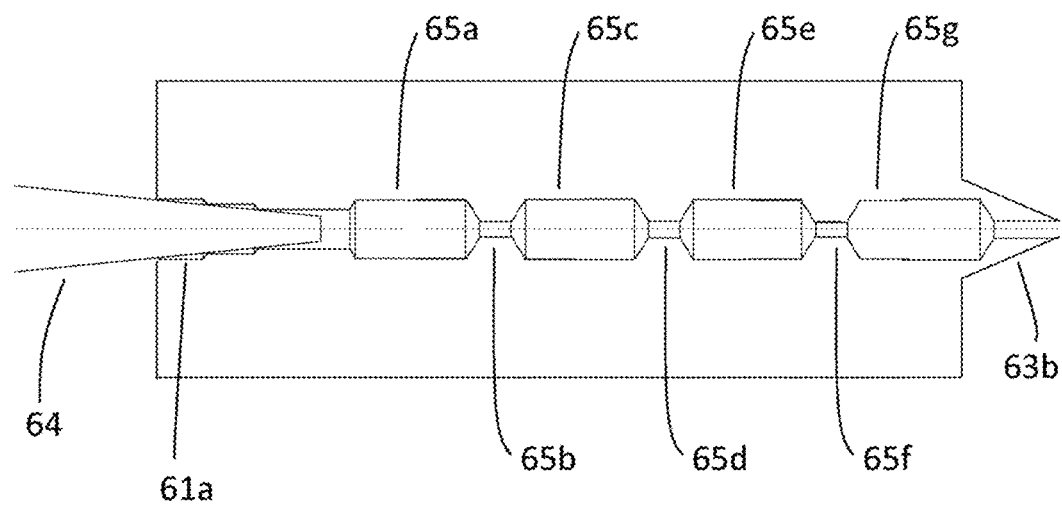
FIG. 43 is a schematic view of a cell mass dissociater according to an embodiment.
Figure 44:
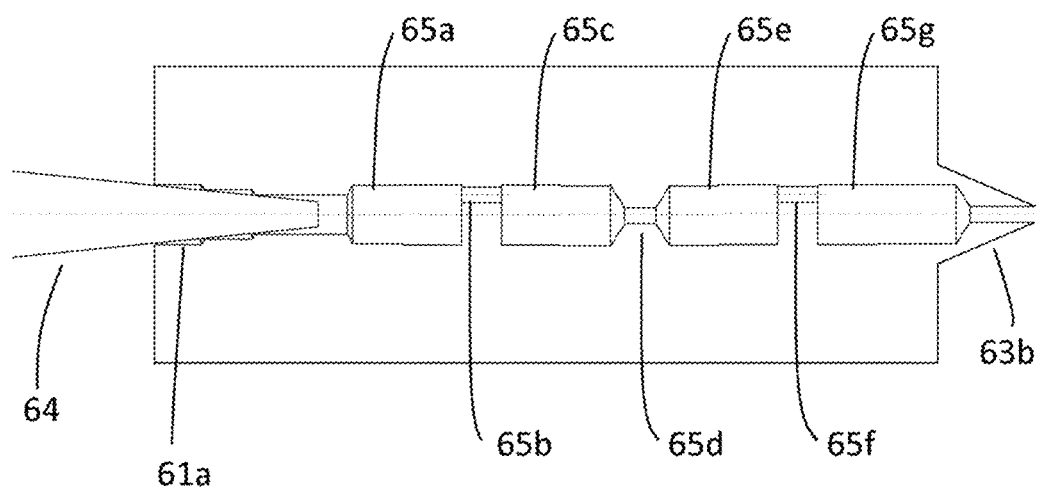
FIG. 44 is a schematic view of a cell mass dissociater according to an embodiment.

If a suitable number and suitable lengths of repeating large pore size sections and small pore size sections have been determined, the cell mass dissociater does not need to be composed of a plurality of blocks. For example, as shown in FIG. 43, the cell mass dissociater may have an integral cylindrical shape with a through-hole in the interior, the through-hole through which the cell mass-containing culture medium flows having, in an alternating manner, large pore size sections 65a, 65c, 65e, 65g, and small pore size sections 65b, 65d, 65f that communicate with the large pore size sections 65a, 65c, 65e, 65g and have smaller pore sizes than the large pore size sections 65a, 65c, 65e, 65g. In this case as well, as shown in FIG. 44, the central axes of the large pore size sections 65a, 65c, 65e, 65g and the central axes of at least some of the small pore size sections 65b, 65d, 65f may be offset.

Figure 45:
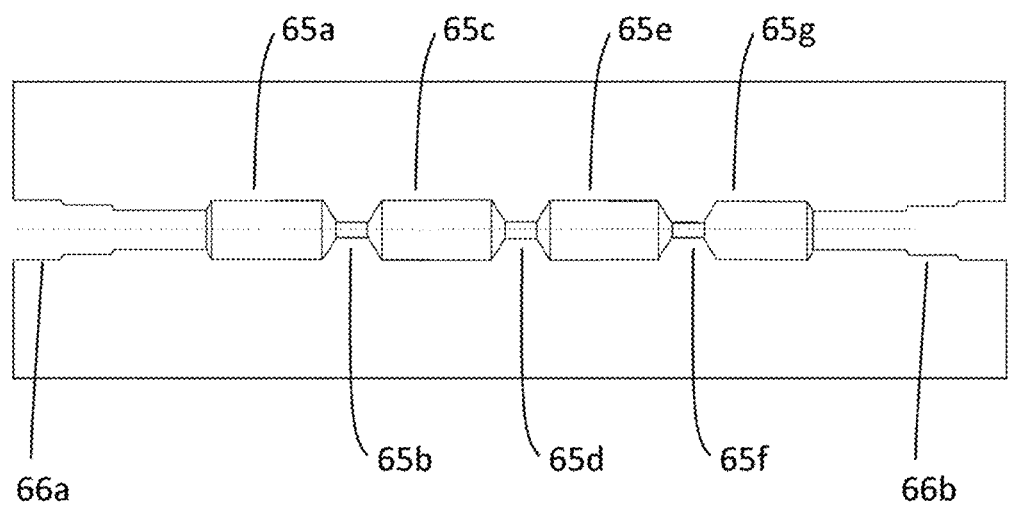
FIG. 45 is a schematic view of a cell mass dissociater according to an embodiment.
Figure 46:
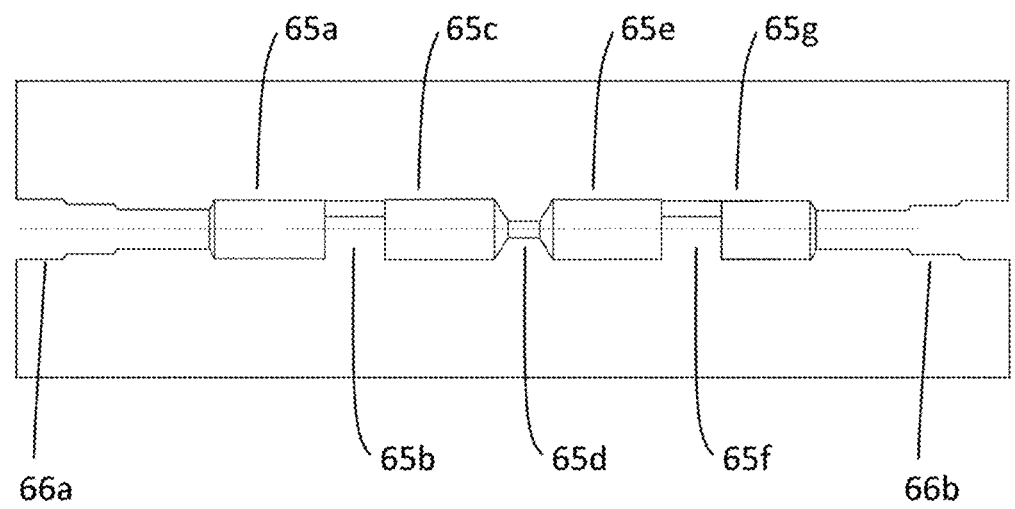
FIG. 46 is a schematic view of a cell mass dissociater according to an embodiment.

The culture medium may pass through the cell mass dissociater only once to dissociate the cell masses in the culture medium into small cell masses. In this case, as shown in FIG. 45, insertion sections 66a, 66b may be provided to allow insertion of a tube or the like at both ends of the cell mass dissociater. The culture medium passes from the insertion section 66a through the through-hole and is discharged from the insertion section 66b, during which time the cell masses in the culture medium are dissociated. In this case as well, as shown in FIG. 46, the central axes of the large pore size sections 65a, 65c, 65e, 65g and the central axes of at least some of the small pore size sections 65b, 65d, 65f may be offset.

The amplifying culturing apparatus 70 is connected to the first dissociating mechanism 60 shown in FIG. 16. The solution including cell masses that have been dissociated at the first dissociating mechanism 60 is fed to the amplifying culturing apparatus 70.

The amplifying culturing apparatus 70 can house a well plate in its interior. The amplifying culturing apparatus 70 also comprises a pipetting machine. The amplifying culturing apparatus 70 receives the solution including the plurality of cell masses from the first dissociating mechanism 60, and the solution is allocated into the wells with a pipetting machine. After allocating the cell masses into the wells, the amplifying culturing apparatus 70 cultures the cell masses for about 8 days, for example, at 37° C., 5% $CO_2$. The amplifying culturing apparatus 70 also carries out appropriate exchange of the culture medium.

The amplifying culturing apparatus 70 then adds a trypsin-substituting recombinant enzyme such as TrypLE Select® (Life Technologies Corp.) to the cell masses. In addition, the amplifying culturing apparatus 70 places a vessel containing the collected cell masses in an incubator, and reacts the cell masses with the trypsin-substituting recombinant enzyme for 1 minute at 37° C., 5% $CO_2$. When the cell masses are to be physically disrupted, there is no need for a trypsin-substituting recombinant enzyme. For example, the amplifying culturing apparatus 70 may disrupt the cell masses by pipetting with a pipetting machine. Alternatively, the amplifying culturing apparatus 70 may disrupt the cell masses by passing the cell masses through a pipe provided with a filter, or a pipe that intermittently varies the inner diameter, similar to the introduced cell solution-feeding channel 31 shown in FIG. 17 or FIG. 18. The amplifying culturing apparatus 70 then adds culture medium such as maintenance culture medium to the solution containing the cell masses. Furthermore, when the amplifying culturing apparatus 70 carries out adhesion culture, the cell masses are scraped from the vessel with an automatic cell scraper or the like, and the cell mass-containing solution is fed to the first dissociating mechanism 60 through an amplifying culturing solution-feeding channel 71.

Culturing in the amplifying culturing apparatus 70 may be carried out in a $CO_2$-permeable bag instead of a well plate. The culturing may also be by adhesion culture, or by suspension culture, or by hanging drop culture. Agitation culture may be carried out in the case of a suspension culture. The culture medium may also be in the form of agar. Agar culture media include gellan gum polymers and deacylated gellan gum polymers. When agar culture medium is used, there is no settling or adhesion of cells, and therefore agitation is not necessary even though it is suspension culture.

The amplifying culturing apparatus 70 may also comprise a second culture medium supply device that supplies culture solution to the well plate or $CO_2$-permeable bag. The second culture medium supply device collects the culture solution in the well plate or $CO_2$-permeable bag, and it may use a filter or dialysis membrane to filter the culture solution, to allow reuse of the purified culture solution. During this time, growth factors or the like may be added to the culture solution that is to be reused. The amplifying culturing apparatus 70 may also comprise a temperature regulating device that regulates the temperature of the culture medium, and a humidity regulating device that regulates the humidity in the vicinity of the culture medium.

In the amplifying culturing apparatus 70, the cells may be placed in a culture solution-permeable bag 301 such as a dialysis membrane as shown in FIG. 19, for example, and the culture solution-permeable bag 301 may be placed in a culture solution-impermeable $CO_2$-permeable bag 302, so that the culture solution is placed in bags 301, 302. The initializing culturing apparatus 50 may have multiple bags 302 prepared containing fresh culture solution, and the bag 302 in which the cell-containing bag 301 is placed may be replaced by a bag 302 containing fresh culture solution, at prescribed intervals of time.

The culturing method in the amplifying culturing apparatus 70 is not limited to the method described above, and may employ a suspension culture vessel such as shown in FIG. 20, similar to the culturing method in the initializing culturing apparatus 50. In the amplifying culturing apparatus 70, the plurality of cell masses are to be placed in the dialysis tube 75 of the suspension culture vessel shown in FIG. 20. The details regarding the suspension culture vessel are as explained above. In the amplifying culturing apparatus 70 as well, a supply culture medium solution-feeding pump 77 may be used as shown in FIG. 21, for exchange and supply of the gel medium surrounding the dialysis tube 75 in the vessel 76. Alternatively, as shown in FIG. 22, the supply culture medium solution-feeding pump 77 and the interior of the dialysis tube 75 in the suspension culture vessel 76 may be connected by the solution-feeding tube 78, to supply the components necessary for culturing of cells in the culture medium in the dialysis tube 75.

The cell processing system may further comprise an amplifying culturing photographing device that photographically records culturing in the amplifying culturing apparatus 70, as shown in FIG. 16. If a colorless culture medium is used for the culture medium in the amplifying culturing apparatus 70, it will be possible to minimize diffuse reflection and autologous fluorescence that may be produced when using a colored culture medium. In order to confirm the pH of the culture medium, however, a pH indicator such as phenol red may be included. Moreover, since induced cells and non-induced cells have differences in cellular shape and size, the cell processing system may further comprise an induced state monitoring device that calculates the proportion of induced cells by photographing the cells in the amplifying culturing apparatus 70. Alternatively, the induced state monitoring device may determine the proportion of induced cells by antibody immunostaining or RNA extraction. In addition, the cell processing system may comprise a non-induced cell removing device that removes cells that have not been induced, by magnetic-activated cell sorting, flow cytometry or the like.

The amplifying culturing photographing device is similar to the initializing culturing photographing device 171 shown in FIG. 23, and it may photograph culturing in the amplifying culturing apparatus 70 through a telecentric lens 172. The illumination method during photography by the amplifying culturing photographing device may also be the same as the illumination method during photography by the initializing culturing photographing device 171, which is as described above.

The amplifying culturing photographing device is also connected to a CPU 500 comprising an image processor 501, as shown in FIG. 26. The image processor 501 comprising the outline defining unit 511, cell evaluating unit 512, statistical processor 513, density calculating unit 514 and culture medium evaluating unit 515, performs image processing on the image taken by the amplifying culturing photographing device, in the same manner as for the image taken by the initializing culturing photographing device 171. The details regarding the image processor 501 are as described above.

For example, if the cell mass grows too large during amplifying culturing, the nutrients and hormones in the culture medium may fail to reach the interior and the cells may differentiate. In addition, if cell masses that are too small are subcultured, without using a ROCK inhibitor, cell death or karyotypic abnormalities may occur. The cell evaluating unit 512 may therefore emit an alert when the individual cell mass sizes are outside of the suitable range. In addition, the cell evaluating unit 512 may output a timing for subculturing when the individual cell mass sizes are beyond a prescribed threshold value. In this case, the cell masses may be fragmented to reduce the sizes of the individual cell masses, and subcultured by resuming culturing in the culturing vessel. In addition, if the individual cell mass sizes after fragmentation of the cell masses are calculated during the subculturing, it is possible to judge whether or not the fragmentation has been adequate. The supply rate of culture medium at the amplifying culturing apparatus 70 may also be varied according to the calculated cell mass sizes. For example, the supply rate of the culture medium may be increased as the cell mass sizes increase.

The supply rate of culture medium at the amplifying culturing apparatus 70 may also be varied according to the number of cell masses calculated by the statistical processor 513. For example, the supply rate of the culture medium may be increased as the number of cell masses increases.

The density calculating unit 514 may also output a timing for subculturing, when the cell mass density has reached at least a prescribed threshold value. When the cell mass density has become higher than the suitable range, the cell mass density may be adjusted to within the suitable range by subculturing, for example. In addition, if the cell mass density after fragmentation of the cell masses is calculated during the subculturing, it is possible to judge whether or not the fragmentation has been adequate. The supply rate of culture medium at the amplifying culturing apparatus 70 may also be varied according to the calculated cell mass density. For example, the supply rate of the culture medium may be increased as the cell mass density increases.

When the culture medium evaluating unit 515 has judged that the culture medium hue or the culture medium pH is outside of the prescribed range, the culture medium surrounding the dialysis tube 75 of the suspension culture vessel is exchanged by the supply culture medium solution-feeding pump 77 shown in FIG. 21, for example, at the amplifying culturing apparatus 70 as well. Alternatively, when the culture medium is being constantly exchanged, the exchange rate of the culture medium surrounding the dialysis tube 75 of the suspension culture vessel by the supply culture medium solution-feeding pump 77 increases, and the flow rate of the exchanged culture medium increases. This allows the culture medium pH to be maintained within a range suitable for cell culturing, and allows sufficient nutrients to be supplied to the culture medium.

The cell masses that have been dissociated by the first dissociating mechanism 60 shown in FIG. 16 are again cultured in the amplifying culturing apparatus 70. Dissociation of the cell masses at the first dissociating mechanism 60 and culturing of the cell masses in the amplifying culturing apparatus 70 are repeated until the necessary cell volume is obtained.

The pump that delivers the cell mass-containing solution in the amplifying culturing apparatus 70 to the first dissociating mechanism 60 through the amplifying culturing solution-feeding channel 71 may be driven when, for example, the value of the cell mass size calculated by the cell evaluating unit 512 shown in FIG. 26 is at least a prescribed threshold value. Alternatively, the pump that delivers the cell mass-containing solution to the first cell mass solution-feeding channel 51 shown in FIG. 16 may be driven when, for example, the value of the cell mass density calculated by the density calculating unit 514 shown in FIG. 26 is at least a prescribed threshold value.

A second cell mass solution-feeding channel 72 is connected to the amplifying culturing apparatus 70. The amplifying culturing apparatus 70 delivers the cell mass-containing solution, that has been amplifying cultured and detached from the vessel, to the second cell mass solution-feeding channel 72 using a pump or the like. Detachment is not necessary, however, in the case of suspension culture. The second cell mass solution-feeding channel 72 may have an inner diameter that allows passage of only induced cells of less than a prescribed size, and it may be connected to a branched fluid channel that removes non-induced cells of a prescribed size or larger.

The inner wall of the second cell mass solution-feeding channel 72 may be coated with poly-HEMA to render it non-cell-adherent, so that the cells do not adhere. Alternatively, a material resistant to cell adhesion may be used as the material for the second cell mass solution-feeding channel 72. Also, by using a material with good thermal diffusivity and $CO_2$ permeability as the material for the second cell mass solution-feeding channel 72, the conditions in the second cell mass solution-feeding channel 72 will be equivalent to the controlled temperature and $CO_2$ concentration in the enclosure 601. A back-flow valve may also be provided in the second cell mass solution-feeding channel 72 from the viewpoint of preventing contamination.

The second cell mass solution-feeding channel 72 is connected to the second dissociating mechanism 80. The second dissociating mechanism 80 comprises a mesh, for example. The cell masses in the solution are dissociated into a plurality of cell masses corresponding to the sizes of the holes of the mesh, when they pass through the mesh by water pressure. If the mesh hole sizes are uniform, for example, the sizes of the plurality of cell masses after being dissociated will be approximately uniform. Alternatively, the second dissociating mechanism 80 may comprise a nozzle. For example, if the interior of an approximately conical nozzle is micromachined in a step-wise manner, a cell mass in the solution will be dissociated into a plurality of cell masses when it passes through the nozzle.

Alternatively, the second dissociating mechanism 80, similar to the first dissociating mechanism 60, may comprise a cell mass dissociater comprising a terminal block 61, connecting block 62 and tip block 63 as shown in FIG. 39 to FIG. 42, or an integral cell dissociater as shown in FIG. 43 to FIG. 46. The details regarding the cell mass dissociater are as explained above.

The cell mass transport mechanism 90 that sends the plurality of cell masses in order to the packaging device 100 is connected to the second dissociating mechanism 80 shown in FIG. 16. A pre-packaging cell channel 91 is connected between the cell mass transport mechanism 90 and the packaging device 100. The cell mass transport mechanism 90 employs a pump or the like to send each of the cell masses that have been dissociated by the second dissociating mechanism 80, to the packaging device 100 through the pre-packaging cell channel 91.

The pre-packaging cell channel 91 is coated with poly-HEMA so that the cells do not adhere. Alternatively, a material resistant to cell adhesion may be used as the material for the pre-packaging cell channel 91. Also, by using a material with good thermal diffusivity and $CO_2$ permeability as the material of the pre-packaging cell channel 91, the conditions in the pre-packaging cell channel 91 will be equivalent to the controlled temperature and $CO_2$ concentration in the enclosure 601. A back-flow valve may also be provided in the pre-packaging cell channel 91 from the viewpoint of preventing contamination.

A cryopreservation liquid-feeding mechanism 110 is connected to the pre-packaging cell channel 91. The cryopreservation liquid-feeding mechanism 110 feeds a cell cryopreservation liquid into the pre-packaging cell channel 91. As a result, the cell masses are suspended in the cell cryopreservation liquid inside the pre-packaging cell channel 91.

The packaging device 100 freezes each of the plurality of cell masses in order, that have been fed through the pre-packaging cell channel 91. For example, each time it receives cell masses, the packaging device 100 places the cell masses in a cryopreservation vessel such as a cryotube, and immediately freezes the cell mass solution at −80° C. or below, for example. When using a cryopreservation vessel with a small surface area per volume, more time will tend to be necessary for freezing, and therefore it is preferred to use a cryopreservation vessel with a large surface area per volume. By using a cryopreservation vessel with a large surface area per volume it is possible to increase the survival rate of the cells after thawing. The shape of the cryopreservation vessel may be capillary-like or spherical, without any particular restrictions. Immediate freezing is not necessarily essential, depending on the survival rate required for the cells after thawing.

Vitrification, for example, may be employed for the freezing. In this case, the cell cryopreservation liquid used may be DAP213 (Cosmo Bio Co., Ltd.) or Freezing Medium (ReproCELL, Inc.). The freezing may also be carried out by a common method other than vitrification. In this case, the cell cryopreservation liquid used may be CryoDefend-Stem Cell (R&D Systems) or STEM-CELLBANKER® (Zenoaq). The freezing may be carried out with liquid nitrogen, or it may be carried out with a Peltier element. When a Peltier element is used, temperature changes can be controlled and temperature variation can be minimized. When the frozen cells are to be used in the clinic, the cryopreservation vessel is preferably a completely closed system. However, the packaging device 100 may package the stem cells in a storage vessel without freezing.

Figure 48:
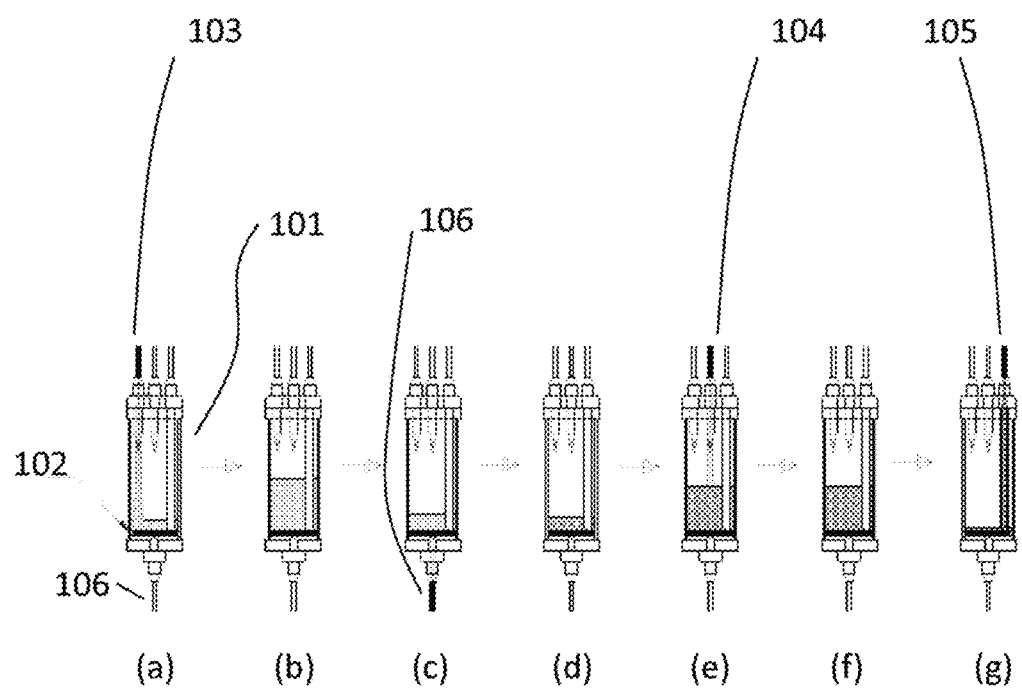
FIG. 48 is a schematic view of a solution exchanger according to an embodiment.

Alternatively, in the packaging device 100, the cell mass solution may be exchanged from the culture medium to the cryopreservation liquid using a solution exchanger 101 as illustrated in FIG. 48. Inside the solution exchanger 101 there is provided a filter 102 having at the bottom a fine hole which does not permit passage of cell masses. In the solution exchanger 101 there is also provided a cell mass introduction hole where a first solution-feeding channel 103 that feeds cell mass-containing culture medium onto the internal filter 102 is connected, an exchange solution introduction hole where a second solution-feeding channel 104 that feeds cell mass-free frozen solution onto the internal filter 102 is connected, and a cell mass outflow hole where a first discharge channel 105 that discharges cell mass-containing frozen solution onto the internal filter 102 is connected. There is also provided in the solution exchanger 101 a waste liquid outflow hole wherein there is connected a second discharge channel 106 that discharges solution that has passed through the filter 102. Tubes or the like may be used for each of the first solution-feeding channel 103, second solution-feeding channel 104, first discharge channel 105 and second discharge channel 106.

First, as shown in FIG. 48(*a*) and FIG. 48(*b*), cell mass-containing culture medium is placed inside the solution exchanger 101 from the first solution-feeding channel 103, while flow of the solution in the second discharge channel 106 is stopped. Next, as shown in FIG. 48(*c*), a state is formed allowing flow of the solution in the second discharge channel 106, and the culture medium is discharged from the solution exchanger 101. The cell masses remain on the filter 102 during this time, as shown in FIG. 48(*d*). As shown in FIG. 48(*e*) and FIG. 48(*f*), the cryopreservation liquid is first placed inside the solution exchanger 101 from the second solution-feeding channel 104, while flow of the solution in the second discharge channel 106 is stopped, and the cell masses are dispersed in the cryopreservation liquid. Next, as shown in FIG. 48(*g*), the cell mass-containing cryopreservation liquid is discharged from the first discharge channel 105. The cell mass-containing cryopreservation liquid is sent to a cryopreservation vessel or the like through the first discharge channel 105.

The solution exchanger 101 shown in FIG. 48 may be used not only for exchange from culture medium to cryopreservation liquid, but also for exchange from old culture medium to fresh culture medium. In this case, the second solution-feeding channel 104 feeds fresh culture medium. Alternatively, when dissociating the cell masses, the solution exchanger 101 may be used for exchange of the culture medium with solution containing a cell mass dissociating enzyme. Examples of cell mass dissociating enzymes include trypsin, and trypsin-substituting recombinant enzymes such as TrypLE Select® (Life Technologies Corp.). In this case, the second solution-feeding channel 104 feeds solution containing a cell mass dissociating enzyme.

The cell processing system may further comprise a packaging step photographing device in which the packaging step is photographed at the packaging device 100, as shown in FIG. 16.

The cell processing system may also record the behavior of the separating device 10, preintroduction cell solution-feeding channel 20, inducing factor solution-feeding mechanism 21, factor introducing device 30, cell mass preparation device 40 and packaging device 100, and may transmit the image taken by the photographing device to an external server, in either a wired or wireless manner. At the external server, factors such as the conditions including the inducing factor introduction conditions, the culturing conditions and the freezing conditions, and results such as incomplete initialization of the stem cells, failed differentiation and growth of the stem cells and chromosomal aberrations, for example, are analyzed by a neural network, and the conditions leading to results may be extracted and results predicted. In addition, the external server may control the separating device 10, inducing factor solution-feeding mechanism 21, factor introducing device 30, cell mass preparation device 40 and packaging device 100 of the cell processing system based on a standard operating procedure (SOP), monitor whether or not each device is running based on the SOP, and automatically produce a running record for each device.

With the cell processing system described above, it is possible to carry out induction, establishment, amplifying culturing and cryopreservation of stem cells such as iPS cells, fully automatically in a single process.

The cell processing apparatus of the cell processing system according to this embodiment is not limited to the construction illustrated in FIG. 16. For example, in the cell processing apparatus shown in FIG. 49, blood is delivered from the blood storing unit 201 to the mononuclear cell separating unit 203, through a blood solution-feeding channel 202. Tubes, for example, may be used as the blood storing unit 201 and mononuclear cell separating unit 203. The blood solution-feeding channel 202 may be a resin tube or silicon tube, for example. This also applies for the other solution-feeding channels described below. An identifier such as a barcode is attached to the blood storing unit 201 for control of the blood information. A pump 204 is used for feeding of the solution. The pump 204 that is used may be a positive-displacement pump. Examples of positive-displacement pumps include reciprocating pumps including piston pumps, plunger pumps and diaphragm pumps, and rotating pumps including gear pumps, vane pumps and screw pumps. Examples of diaphragm pumps include tubing pumps and piezoelectric pumps. Examples of tubing pumps include Perista Pump® (Atto Corp.) and RP-Q1 and RP-TX (Takasago Electric, Inc.). Examples of piezoelectric pumps include SDMP304, SDP306, SDM320 and APP-20KG (Takasago Electric, Inc.). A microflow chip module (Takasago Electric, Inc.) comprising a combination of various different pumps may also be used. When a sealed pump such as a Perista Pump®, tubing pump or diaphragm pump is used, feeding can be accomplished without direct contact of the pump with the blood inside the blood solution-feeding channel 202. The same also applies to the other pumps described below. Alternatively, syringe pumps may be used for the pump 204, and for the pump 207, pump 216, pump 222, pump 225, pump 234, pump 242 and pump 252 described below. Even pumps other than sealed pumps may be reutilized after heat sterilization treatment.

An erythrocyte coagulant is fed to the mononuclear cell separating unit 203 from the separating agent storing unit 205, through a solution-feeding channel 206 and the pump 207. Tubes, for example, may be used as the separating agent storing unit 205. An identifier such as a barcode is attached to the separating agent storing unit 205 for control of the separating agent information. The erythrocyte coagulant used may be, for example, HetaSep® (STEMCELL Technologies) or an Erythrocyte Coagulant (Nipro Corp.). In the mononuclear cell separating unit 203, the erythrocytes precipitate by the erythrocyte coagulant and the mononuclear cells are separated. The mononuclear cell-containing supernatant in the mononuclear cell separating unit 203 is sent to a mononuclear cell purifying filter 210 through a mononuclear cell solution-feeding channel 208 and pump 209. At the mononuclear cell purifying filter 210, components other than the mononuclear cells are removed to obtain a mononuclear cell-containing solution. The mononuclear cell purifying filter 210 used may be Purecell® (PALL), Cellsorba E (Asahi Kasei Corp.), SEPACELL PL (Asahi Kasei Corp.), ADACOLUMN® (Jimro), or a separation bag (Nipro Corp.).

Figure 49:
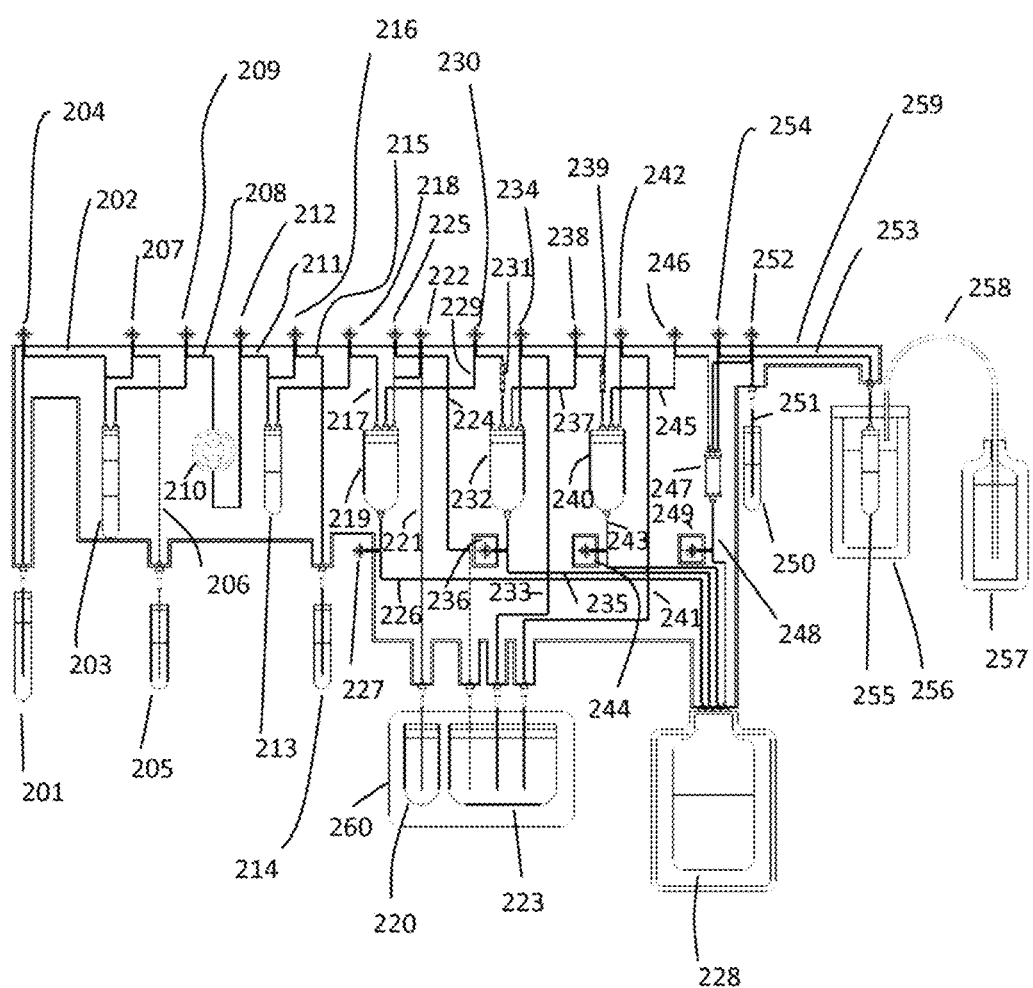
FIG. 49 is a schematic view of a cell processing apparatus according to an embodiment.

In FIG. 49, the mononuclear cell separating unit 203, separating agent storing unit 205, mononuclear cell purifying filter 210 and pumps 204, 207, 209 constitute a separating device.

The mononuclear cell-containing solution is sent to a factor introducing device 213 through a preintroduction cell solution-feeding channel 211 and pump 212. Tubes, for example, may be used as the factor introducing device 213. Pluripotency inducing factor is fed to the factor introducing device 213 from a factor storing unit 214 including pluripotency inducing factor, through a factor solution-feeding channel 215 and the pump 216. Tubes, for example, may also be used as the factor storing unit 214. An identifier such as a barcode is attached to the factor storing unit 214 for control of the pluripotency inducing factor information. The factor storing unit 214 and the pump 216 constitute the inducing factor solution-feeding mechanism. In the factor introducing device 213 as the factor introducing device, the pluripotency inducing factor is introduced into cells by RNA lipofection, for example, and inducing factor-introduced cells are prepared. The method of transfection of the inducing factor, however, is not limited to RNA lipofection. For example, Sendai virus vector including a pluripotency inducing factor may be used. Alternatively, the pluripotency inducing factor may be a protein.

The inducing factor-introduced cells are sent through an introduced cell solution-feeding channel 217 and pump 218 to an initializing culturing vessel 219 as a part of the cell mass preparation device. The introduced cell solution-feeding channel 217 may be temperature-permeable and $CO_2$-permeable, for example. The suspension culture vessel shown in FIG. 20 may be used as the initializing culturing vessel 219. In this case, the inducing factor-introduced cells are placed in a dialysis tube. For the first few days after introduction of the pluripotency inducing factor to the cells, blood cell culture medium is supplied to the initializing culturing vessel 219 shown in FIG. 49 from a blood cell culture medium storing unit 220 including blood cell culture medium, through a culture medium solution-feeding channel 221 and pump 222. The culture medium solution-feeding channel 221 may be temperature-permeable and $CO_2$-permeable, for example. An identifier such as a barcode is attached to the blood cell culture medium storing unit 220 for control of the blood cell culture medium information. The blood cell culture medium storing unit 220, culture medium solution-feeding channel 221 and pump 222 constitute the culture medium supply device. The pump 222 may continuously supply blood cell culture medium, or it may supply blood cell culture medium at a prescribed timing, according to directions by the CPU 500 shown in FIG. 26.

Next, stem cell culture medium is supplied to the initializing culturing vessel 219 shown in FIG. 49, from a stem cell culture medium storing unit 223 including stem cell culture medium, through a culture medium solution-feeding channel 224 and pump 225. An identifier such as a barcode is attached to the stem cell culture medium storing unit 223 for control of the stem cell culture medium information. The culture medium solution-feeding channel 224 may be temperature-permeable and $CO_2$-permeable, for example. The stem cell culture medium storing unit 223, culture medium solution-feeding channel 224 and pump 225 constitute the culture medium supply device. The pump 225 may continuously supply stem cell culture medium, or it may supply stem cell culture medium at a prescribed timing, according to directions by the CPU 500 shown in FIG. 26.

The blood cell culture medium storing unit 220 and stem cell culture medium storing unit 223 may be placed in cold storage in the cold storage unit 260 at a low temperature of 4° C., for example. The culture medium fed from the blood cell culture medium storing unit 220 and the stem cell culture medium storing unit 223 may be fed to the culturing vessel, for example, after having the temperature raised to 37° C. with a heater outside the cold storage unit 260. Alternatively, the temperature surrounding the solution-feeding channel may be set so that the culture medium stored at low temperature increases in temperature to 37° C. while it progresses through the solution-feeding channel. The used culture medium in the initializing culturing vessel 219 is sent to a waste liquid storage section 228 through a waste liquid solution-feeding channel 226 and pump 227. An identifier such as a barcode is attached to the waste liquid storage section 228 for control of the waste liquid information.

The cell masses that have been cultured at the initializing culturing vessel 219 are sent to a first amplifying culturing vessel 232 as a part of the cell mass preparation device, through an introduced cell solution-feeding channel 229, pump 230 and cell mass dissociater 231. The cell mass dissociater 231 may also comprise the construction shown in FIG. 45 or FIG. 46, for example. By passing through the cell mass dissociater 231, the cell masses are dissociated into smaller cell masses. The suspension culture vessel shown in FIG. 20 may be used as the first amplifying culturing vessel 232 shown in FIG. 49. In this case, the cell masses are placed in a dialysis tube. Stem cell culture medium is supplied to the first amplifying culturing vessel 232 shown in FIG. 49, from the stem cell culture medium storing unit 223 including stem cell culture medium, through a culture medium solution-feeding channel 233 and pump 234. The introduced cell solution-feeding channel 229 and culture medium solution-feeding channel 233 may be temperature-permeable and $CO_2$-permeable, for example. The stem cell culture medium storing unit 223, culture medium solution-feeding channel 233 and pump 234 constitute the culture medium supply device. The pump 234 may continuously supply stem cell culture medium, or it may supply stem cell culture medium at a prescribed timing, according to directions by the CPU 500 shown in FIG. 26.

The used culture medium in the first amplifying culturing vessel 232 shown in FIG. 49 is sent to the waste liquid storage section 228 through a waste liquid solution-feeding channel 235 and pump 236.

The cell masses that have been cultured at the first amplifying culturing vessel 232 are sent to a second amplifying culturing vessel 240 as a part of the cell mass preparation device, through an introduced cell solution-feeding channel 237, pump 238 and cell mass dissociater 239. The cell mass dissociater 239 may also comprise the construction shown in FIG. 45 or FIG. 46, for example. By passing through the cell mass dissociater 239, the cell masses are dissociated into smaller cell masses. The suspension culture vessel shown in FIG. 20 may be used as the second amplifying culturing vessel 240 shown in FIG. 49. In this case, the cell masses are placed in a dialysis tube. Stem cell culture medium is supplied to the second amplifying culturing vessel 240 shown in FIG. 49, from the stem cell culture medium storing unit 223 including stem cell culture medium, through a culture medium solution-feeding channel 241 and pump 242. The introduced cell solution-feeding channel 237 and culture medium solution-feeding channel 241 may be temperature-permeable and $CO_2$-permeable, for example. The stem cell culture medium storing unit 223, culture medium solution-feeding channel 241 and pump 242 constitute the culture medium supply device. The pump 242 may continuously supply stem cell culture medium, or it may supply stem cell culture medium at a prescribed timing, according to directions by the CPU 500 shown in FIG. 26.

The used culture medium in the second amplifying culturing vessel 240 shown in FIG. 49 is sent to the waste liquid storage section 228 through a waste liquid solution-feeding channel 243 and pump 244.

The cell masses that have been cultured in the second amplifying culturing vessel 240 are sent to a solution exchanger 247 through an introduced cell solution-feeding channel 245 and pump 246. The solution exchanger 247 comprises the construction shown in FIG. 48, for example. In the solution exchanger 247 shown in FIG. 49, the cell masses are held at a filter while the culture medium is sent to the waste liquid storage section 228 through a waste liquid solution-feeding channel 248 and pump 249.

After stopping flow of the solution in the waste liquid solution-feeding channel 248 by stopping driving of the pump 249, or after closing the waste liquid solution-feeding channel 248 with a valve or the like, cryopreservation liquid is placed in the solution exchanger 247 from a cryopreservation liquid storing unit 250, that contains cryopreservation liquid, through a solution-feeding channel 251 and pump 252. This disperses the cell masses in the cryopreservation liquid.

The cryopreservation liquid that has dispersed the cell masses is fed into a cryopreservation vessel 255 through a solution-feeding channel 253 and pump 254, as parts of the packaging device. The cryopreservation vessel 255 is situated in a low-temperature repository 256. Liquid nitrogen at −80° C., for example, is fed to the low-temperature repository 256 from a liquid nitrogen repository 257, through a solution-feeding channel 258. The cell masses in the cryopreservation vessel 255 are thus frozen. Freezing of the cell masses does not need to be by liquid nitrogen, however. For example, the low-temperature repository 256 may be a freezer such as a compression freezer, an absorption freezer or a Peltier freezer.

Back-flow valves may also be provided in the solution-feeding channels as appropriate. The solution-feeding channels, mononuclear cell separating unit 203, mononuclear cell purifying filter 210, factor introducing device 213, initializing culturing vessel 219, first amplifying culturing vessel 232, second amplifying culturing vessel 240 and solution exchanger 247 are situated in an element 259, for example. The material of the element 259 may be, but is not limited to, a resin, for example. The element 259 is made of a sterilizable heat-resistant material, for example. The element 259 may be in the form of a plate or a cassette. The element 259 may also be a flexible bag. The solution-feeding channel through which the culture medium flows is made of a $CO_2$-permeable material, for example. The solution-feeding channels, mononuclear cell separating unit 203, mononuclear cell purifying filter 210, factor introducing device 213, initializing culturing vessel 219, first amplifying culturing vessel 232, second amplifying culturing vessel 240 and solution exchanger 247 may also be housed in a plurality of separate cases.

The element 259, and the enclosure 601 shown in FIG. 1, comprise, for example, engaging parts that mutually engage. Therefore, the element 259 shown in FIG. 49 is disposed at a prescribed location inside the enclosure 601 shown in FIG. 1. Furthermore, the pump, blood storing unit 201, separating agent storing unit 205, factor storing unit 214, blood cell culture medium storing unit 220, stem cell culture medium storing unit 223, waste liquid storage section 228, cryopreservation vessel 255, low-temperature repository 256 and liquid nitrogen repository 257 shown in FIG. 49 are also disposed at prescribed locations inside the enclosure 601. When the element 259 is disposed at the prescribed location inside the enclosure 601 shown in FIG. 1, the solution-feeding channels in the element 259 shown in FIG. 49 are in contact with the pump, blood storing unit 201, separating agent storing unit 205, factor storing unit 214, blood cell culture medium storing unit 220, stem cell culture medium storing unit 223, waste liquid storage section 228, cryopreservation vessel 255, low-temperature repository 256 and liquid nitrogen repository 257.

The element 259 and the channel provided in the element 259 may be disposable, for example, and upon completion of freezing of the cell masses, they may be discarded and exchanged with new ones. Alternatively, when the element 259 and the channel provided in the element 259 are to be reused, an identifier such as a barcode may be attached to the element 259 to manage the number of times used, etc.

With the cell processing system of the embodiment described above, it is possible to automatically process cryopreserved stem cells such as iPS cells from blood.

Figure 50:
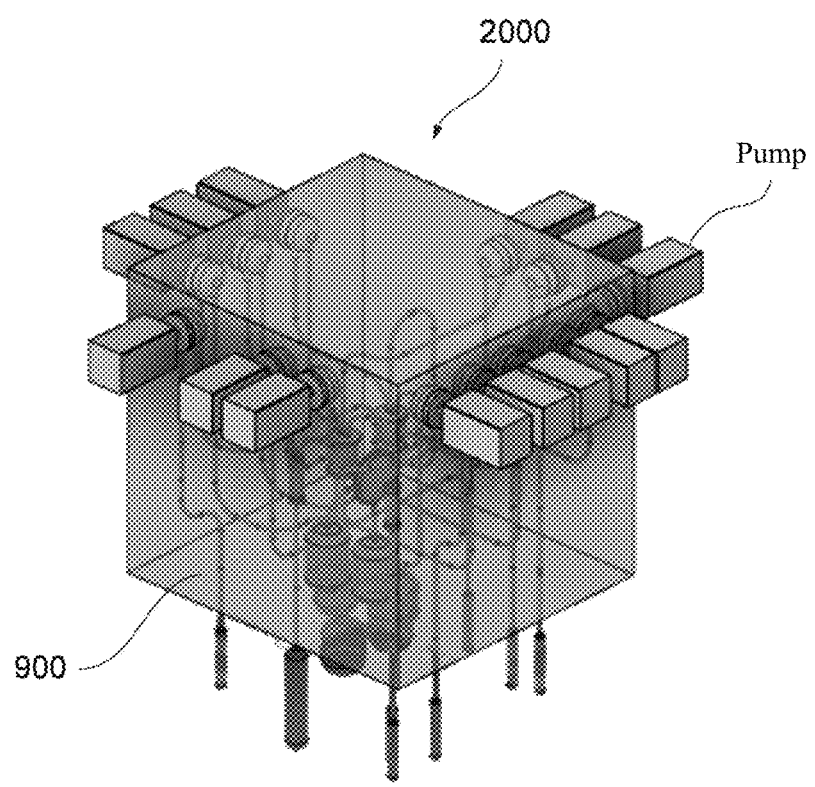
FIG. 50 is a schematic perspective view of a cell processing apparatus according to an embodiment.
Figure 51:
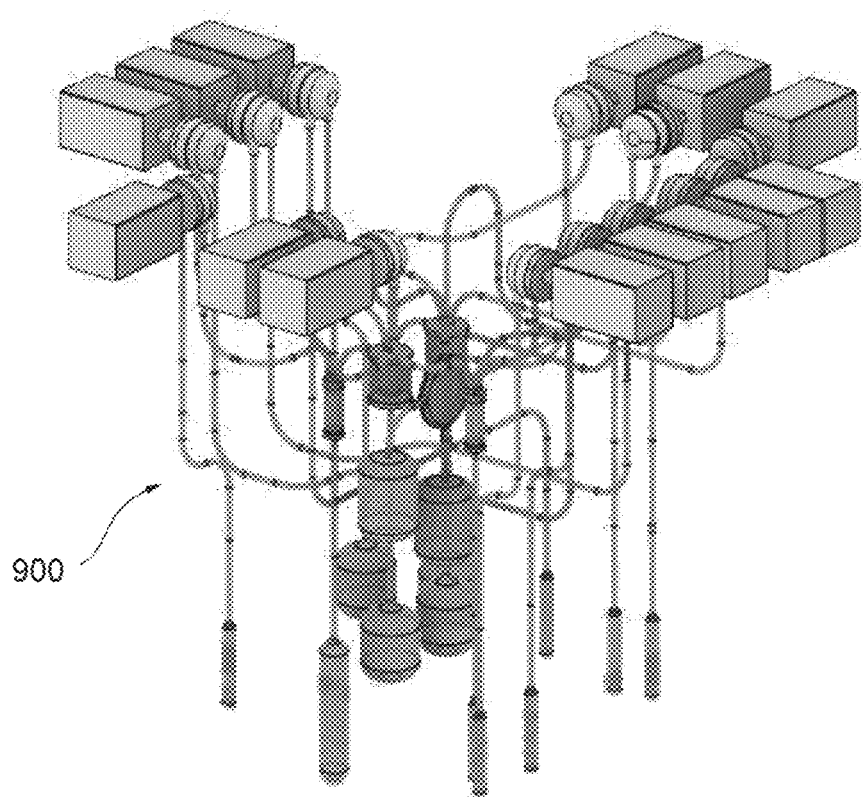
FIG. 51 is a schematic perspective view of a cell processing apparatus according to an embodiment.
Figure 52:
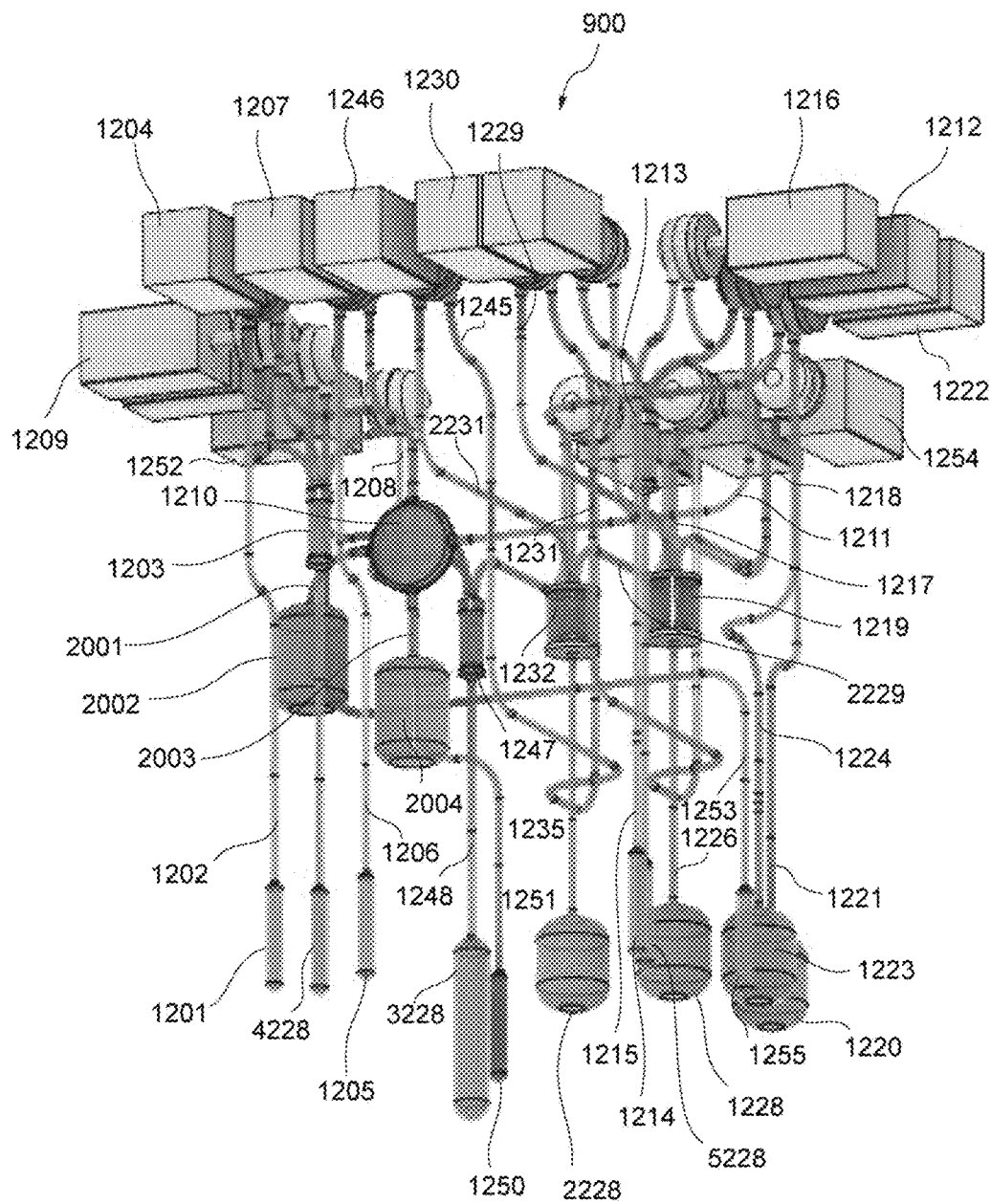
FIG. 52 is a schematic perspective view of a cell processing apparatus according to an embodiment.

Moreover, as shown in FIG. 50, FIG. 51 and FIG. 52, the cell processing apparatus may also comprise a cell culture device 900, an embedding member 2000 that embeds the cell culture device 900, and a communicating solution-feeding channel that allows communication between the outside of the embedding member 2000 and the cell culture device 900 that is inside the embedding member 2000. The embedding member 2000 is omitted in FIG. 51 and FIG. 52.

The material used for the embedding member 2000 may be a resin, glass, a metal, or the like. If the embedding member 2000 is transparent it will be possible to observe the cell culture device 900 disposed inside the embedding member 2000, but it may also be opaque.

In the cell processing apparatus, blood is fed from a blood storing unit 1201, disposed outside the embedding member 2000, that stores blood, to a mononuclear cell separating unit 1203 disposed inside the embedding member 2000, through a blood solution-feeding channel 1202. Tubes, for example, may be used as the blood storing unit 1201 and mononuclear cell separating unit 1203. The blood solution-feeding channel 1202 may be a resin tube or silicon tube, for example. This also applies for the other solution-feeding channels described below. An identifier such as a barcode is attached to the blood storing unit 1201 for control of the blood information.

A driving unit 1204 such as a pump that is attachable to the outer wall of the embedding member 2000 is used for the feeding. The driving unit 1204 that is used may be a positive-displacement pump. Examples of positive-displacement pumps include reciprocating pumps including piston pumps, plunger pumps and diaphragm pumps, and rotating pumps including gear pumps, vane pumps and screw pumps. Examples of diaphragm pumps include tubing pumps and piezoelectric pumps. Examples of tubing pumps include Perista Pump® (Atto Corp.) and RP-Q1 and RP-TX (Takasago Electric, Inc.). Examples of piezoelectric pumps include SDMP304, SDP306, SDM320 and APP-20KG (Takasago Electric, Inc.). A microflow chip module (Takasago Electric, Inc.) comprising a combination of various different pumps may also be used. When a sealed pump such as a Perista Pump®, tubing pump or diaphragm pump is used, feeding can be accomplished without direct contact of the pump with the blood inside the blood solution-feeding channel 1202. The same also applies to the other pumps described below. Alternatively, a syringe pump may be used for the driving unit 1204, as well as for the driving units mentioned below. Even pumps other than sealed pumps may be reutilized after heat sterilization treatment.

Figure 53:
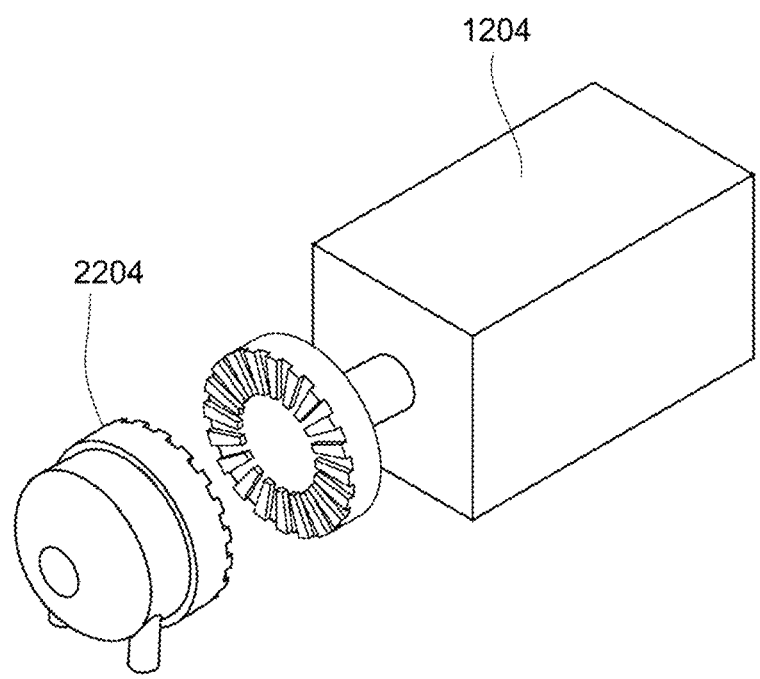
FIG. 53 is a schematic perspective view of a driving unit in a cell processing apparatus according to an embodiment.
Figure 54:
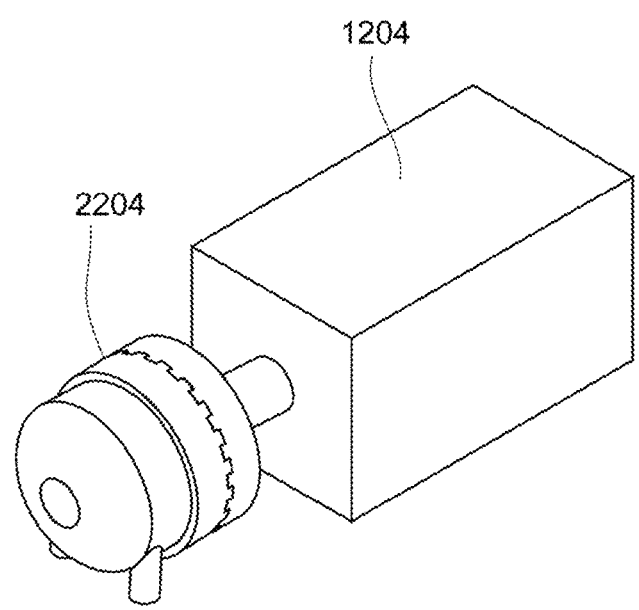
FIG. 54 is a schematic perspective view of a driving unit in a cell processing apparatus according to an embodiment.

For example, a slave unit 2204 to which driving force from the driving unit 1204 is transmitted, may be provided inside the embedding member 2000 as shown in FIG. 53 and FIG. 54, with the slave unit 2204 being connected to the blood solution-feeding channel 1202. The driving unit 1204 and the slave unit 2204 may also be connected by magnetic force. The driving unit 1204 may comprise an electromagnet that generates magnetic force. This also applies to the driving units other than the driving unit 1204.

A separating agent for separation of mononuclear cells of the erythrocyte coagulant is fed from the separating agent storing unit 1205 disposed on the outside of the embedding member 2000, to the mononuclear cell separating unit 1203 disposed inside the embedding member 2000, shown in FIG. 50, FIG. 51 and FIG. 52, through a separating agent solution-feeding channel 1206 and a driving unit 1207 that is attachable to the outer wall of the embedding member 2000. Tubes, for example, may be used as the separating agent storing unit 1205. An identifier such as a barcode is attached to the separating agent storing unit 1205 for control of the separating agent information. The erythrocyte coagulant used may be, for example, HetaSep® (STEMCELL Technologies) or an Erythrocyte Coagulant (Nipro Corp.).

In the mononuclear cell separating unit 1203, the erythrocytes precipitate by the erythrocyte coagulant and the mononuclear cells are separated. The supernatant containing the mononuclear cells in the mononuclear cell separating unit 1203 is fed to a mononuclear cell purifying filter 1210, through a mononuclear cell solution-feeding channel 1208 disposed inside the embedding member 2000 and a driving unit 1209 that is attachable to the outer wall of the embedding member 2000. The precipitated portion produced in the mononuclear cell separating unit 1203 is fed to a waste liquid storage section 4228 disposed on the outside of the embedding member 2000, through a waste liquid solution-feeding channel that allows communication from the inside to the outside of the embedding member 2000.

At the mononuclear cell purifying filter 1210, components other than the mononuclear cells are removed to obtain a mononuclear cell-containing solution. The mononuclear cell purifying filter 1210 used may be Purecell® (PALL), Cellsorba E (Asahi Kasei Corp.), SEPACELL PL (Asahi Kasei Corp.), ADACOLUMN® (Jimro), or a separation bag (Nipro Corp.).

In FIG. 52, the mononuclear cell separating unit 1203, separating agent storing unit 1205, mononuclear cell purifying filter 1210 and driving units 1204, 1207, 1209 constitute a separating device. The solution containing the mononuclear cells, separated at the mononuclear cell purifying filter 1210, may be fed, through a mononuclear cell channel 2001 which is disposed inside the embedding member 2000 and connected to the mononuclear cell purifying filter 1210, to a mononuclear cell storage unit 2002 which is disposed inside the embedding member 2000 and connected to the mononuclear cell channel 2001. The solution containing the separate components other than mononuclear cells separated at the mononuclear cell purifying filter 1210, may be fed, through a non-mononuclear cell component channel 2003 which is disposed inside the embedding member 2000 and connected to the mononuclear cell purifying filter 1210, to a non-mononuclear cell component storage unit 2004 which is disposed inside the embedding member 2000 and connected to the separate component channel 2003.

The solution containing mononuclear cells is fed to a factor introducing device 1213 disposed inside the embedding member 2000, through a preintroduction cell solution-feeding channel 1211 disposed inside the embedding member 2000 and a driving unit 1212 that is attachable to the outer wall of the embedding member 2000. Mononuclear cells separated at the mononuclear cell separating unit 1203 may also be fed to the factor introducing device 1213 without passing through the mononuclear cell purifying filter 1210. Tubes, for example, may be used as the factor introducing device 1213. Pluripotency inducing factor is fed to the factor introducing device 1213 from a factor storing unit 1214 that contains pluripotency inducing factor, disposed outside the embedding member 2000, through a factor solution-feeding channel 1215 provided at least partially inside the embedding member 2000 and a driving unit 1216 disposed outside the embedding member 2000. Tubes, for example, may also be used as the factor storing unit 1214. An identifier such as a barcode is attached to the factor storing unit 1214 for control of the pluripotency inducing factor information. The factor storing unit 1214 and the driving unit 1216 constitute the inducing factor solution-feeding mechanism.

In the factor introducing device 1213, as at least part of the factor introducing device, the pluripotency inducing factor is introduced into cells by RNA lipofection, for example, and inducing factor-introduced cells are prepared. The method of transfection of the inducing factor, however, is not limited to RNA lipofection. For example, Sendai virus vector including a pluripotency inducing factor may be used. Alternatively, the pluripotency inducing factor may be a protein. Another method of transfection is transfection or electroporation using episomal plasmids. The waste liquid produced at the factor introducing device 1213 is fed to a waste liquid storage section 5228 disposed on the outside of the embedding member 2000, through a waste liquid solution-feeding channel that allows communication from the inside to the outside of the embedding member 2000.

The inducing factor-introduced cells are fed to an initializing culturing vessel 1219, as part of the cell mass preparation device, through an introduced cell solution-feeding channel 1217 provided inside the embedding member 2000 and a driving unit 1218 disposed on the outside of the embedding member 2000. The initializing culturing vessel 1219 is embedded in the embedding member 2000. The suspension culture vessel shown in FIG. 20 may be used as the initializing culturing vessel 1219. In this case, the inducing factor-introduced cells are placed in a dialysis tube. For the first few days after introduction of the pluripotency inducing factor to the cells, blood cell culture medium is supplied to the initializing culturing vessel 1219 shown in FIG. 52, from a blood cell culture medium storing unit 1220 disposed outside of the embedding member 2000 and including blood cell culture medium, through a culture medium solution-feeding channel 1221 provided at least partially inside the embedding member 2000 and a driving unit 1254 disposed on the outside of the embedding member 2000. An identifier such as a barcode is attached to the blood cell culture medium storing unit 1220 for control of the blood cell culture medium information. The blood cell culture medium storing unit 1220, culture medium solution-feeding channel 1221 and driving unit 1254 constitute the culture medium supply device. The driving unit 1254 may continuously supply blood cell culture medium, or it may supply blood cell culture medium at a prescribed timing according to directions by the CPU 500 shown in FIG. 26.

Next, stem cell culture medium is supplied to the initializing culturing vessel 1219 shown in FIG. 52, from a stem cell culture medium storing unit 1223 disposed outside of the embedding member 2000 and including stem cell culture medium, through a culture medium solution-feeding channel provided inside the embedding member 2000 and a driving unit disposed on the outside of the embedding member 2000. An identifier such as a barcode is attached to the stem cell culture medium storing unit 1223 for control of the stem cell culture medium information. The stem cell culture medium storing unit 1223, culture medium solution-feeding channel and driving unit constitute the culture medium supply device. The driving unit may continuously supply stem cell culture medium, or it may supply stem cell culture medium at a prescribed timing, according to directions by the CPU 500 shown in FIG. 26.

The blood cell culture medium storing unit 1220 and stem cell culture medium storing unit 1223 may be placed in cold storage in the cold storage unit at a low temperature of 4° C., for example. The culture medium fed from the blood cell culture medium storing unit 1220 and the stem cell culture medium storing unit 1223 may be fed to the culturing vessel, for example, after having the temperature raised to 37° C. with a heater outside the cold storage unit. Alternatively, the temperature surrounding the solution-feeding channel may be set so that the culture medium stored at low temperature increases in temperature to 37° C. while it progresses through the solution-feeding channel. The used culture medium in the initializing culturing vessel 1219 is fed to a waste liquid storage section 1228 disposed on the outside of the embedding member 2000, through a waste liquid solution-feeding channel 1226 that allows communication from the inside to the outside of the embedding member 2000. An identifier such as a barcode is attached to the waste liquid storage section 1228 for control of the waste liquid information.

The cell masses that have been cultured at the initializing culturing vessel 1219 are fed to an amplifying culturing vessel 1232, as part of the cell mass preparation device, through an introduced cell solution-feeding channel 1229 provided inside the embedding member 2000, a driving unit 1230 disposed outside the embedding member 2000, a cell mass dissociater 1231 provided inside the embedding member 2000, a driving unit 1218 disposed outside the embedding member 2000, and an introduced cell solution-feeding channel 2229 provided inside the embedding member 2000. The cell mass dissociater 1231 provided inside the embedding member 2000 may have the construction shown in FIG. 45 or FIG. 46, for example. By passing through the cell mass dissociater 1231, the cell masses are dissociated into smaller cell masses.

The suspension culture vessel shown in FIG. 20 may be used as the first amplifying culturing vessel 1232 shown in FIG. 52. In this case, the cell masses are placed in a dialysis tube. Stem cell culture medium is supplied to the amplifying culturing vessel 1232 shown in FIG. 52, from the stem cell culture medium storing unit 1223 disposed outside the embedding member 2000 and including stem cell culture medium, through a culture medium solution-feeding channel 1224 that allows communication from the outside to the inside of the embedding member 2000, and a driving unit 1222 disposed outside the embedding member 2000. The stem cell culture medium storing unit 1223, culture medium solution-feeding channel 1224 and driving unit 1222 constitute the culture medium supply device. The driving unit may continuously supply stem cell culture medium, or it may supply stem cell culture medium at a prescribed timing according to directions by the CPU 500 shown in FIG. 26.

The used culture medium in the amplifying culturing vessel 1232 shown in FIG. 52 is fed to a waste liquid storage section 2228 disposed outside the embedding member 2000, through a waste liquid solution-feeding channel 1235 that allows communication from the inside to the outside of the embedding member 2000.

The cell masses cultured in the amplifying culturing vessel 1232 are fed to a solution exchanger 1247 provided inside the embedding member 2000, through an introduced cell solution-feeding channel 1245 provided inside the embedding member 2000, a driving unit 1246 that is attachable to the outer wall of the embedding member 2000 and a cell mass dissociater 2231 provided inside the embedding member 2000. The solution exchanger 1247 comprises the construction shown in FIG. 48, for example. In the solution exchanger 1247 shown in FIG. 52, the cell masses are held at a filter while culture medium is fed to a waste liquid storage section 3228 disposed outside the embedding member 2000, through a waste liquid solution-feeding channel 1248 that allows communication from the inside to the outside of the embedding member 2000.

After the waste liquid solution-feeding channel 1248 has been closed with a valve or the like, a cryopreservation liquid is placed in the solution exchanger 1247 from a cryopreservation liquid storing unit 1250 disposed outside the embedding member 2000 and containing the cryopreservation liquid, through a cryopreservation liquid-feeding channel 1251 that allows communication from the outside to the inside of the embedding member 2000 and a driving unit 1252 that is attachable to the outer wall of the embedding member 2000. This disperses the cell masses in the cryopreservation liquid.

The cryopreservation liquid in which the cell masses have been dispersed is fed into a cryopreservation vessel 1255 through a freezing cell solution-feeding channel 1253 which allows communication between the inside and outside of the embedding member 2000, and a driving unit 1209 that is attachable to the outer wall of the embedding member 2000. The solution-feeding channel 1253, driving unit 1254 and cryopreservation vessel 1255 form part of a packaging apparatus. The cryopreservation vessel 1255 is then transferred into the low-temperature repository.

For the cell processing apparatus illustrated in FIG. 50 to FIG. 52, after the factor introducing device 1213, initializing culturing vessel 1219 and amplifying culturing vessel 1232 of the cell culture device 900 have been connected, the embedding member 2000 is molded so as to embed them and they are processed. Alternatively, the factor introducing device 1213, initializing culturing vessel 1219 and amplifying culturing vessel 1232 of the cell culture device 900 of the cell processing apparatus may be formed inside the embedding member 2000 by an apparatus such as a 3D printer. Embedding the factor introducing device 1213, initializing culturing vessel 1219 and amplifying culturing vessel 1232 of the cell culture device 900 with the embedding member 2000 can minimize outward diffusion of the processed cells or the inducing factor introduced into the cells. Likewise, it can minimize contact of outside contaminants with the treated cells.

An embodiment of the invention has been described above, but the description and pertinent drawings that are intended merely to constitute part of the disclosure are not to be understood as limiting the invention. Various alternative embodiments, embodiments and operating technologies will be readily apparent to a person skilled in the art from this disclosure. For example, the factor introducing device 30 may induce the cells not by electroporation or RNA lipofection, but rather by a viral vector such as retrovirus, lentivirus or Sendai virus, or by transfection using plasmids, or by protein transfection. Cells may also be induced by introduction of compounds as factors. The preintroduction cell solution-feeding channel 20, introduced cell solution-feeding channel 31, cell mass solution-feeding channel 51, amplifying culturing solution-feeding channel 71, cell mass solution-feeding channel 72 and pre-packaging cell channel 91 may be provided on a substrate by a microfluidics technique. It will therefore be understood that the invention encompasses various embodiments not described herein.

Example 1

(Preparation)

Human blood cells were acquired from a healthy adult male. There were also prepared modified mRNA (TriLink), a non-adherent dish, a 15 mL tube, a 50 mL tube, Ficoll, a Cytoflowmeter (BD), anti-CD34 antibody (Miltenyi Biotec), anti-CD3 antibody (Miltenyi Biotec), MACS® buffer (Miltenyi Biotec), T cell culture medium, low serum culture medium (Opti-MEM®, Gibco), siRNA introducing reagent (Lipofectamine®, RNAiMAX, Thermo Fisher Scientific) and anti-TRA-1-60 antibody (BD).

The T cell (CD3-positive cell) culture medium was a liquid mixture of the following culture medium A and culture medium B. Culture medium A was a liquid mixture of 15 mL of X vivo-10 (Lonza, 04-743Q) and IL-2 (10 µg/mL). Culture medium B was prepared by mixing X vivo-10 and 50 µL of Dynabeads CD3/CD28 (Life Technologies, 111-31D) in a 1.5 mL tube, vortexing the mixture for 5 seconds, allowing spin-down, stationing the mixture in a DynaMag-2 (Thermo fisher Scientific), and removing the supernatant after one minute of stationing.

There was additionally prepared a blood cell culture medium (blood stem/precursor cell medium) by adding 10 µL of IL-6 (100 µg/mL), 10 µL of SCF (300 µg/mL), 10 µL of TPO (300 µg/mL), 10 µL of Flt3 ligand (300 µg/mL) and 10 µL of IL-3 (10 µg/mL) to 10 mL of serum-free medium (StemSpan H3000, STEMCELL Technologies).

There were further prepared an OCT3/4 mRNA-containing solution, SOX2 mRNA-containing solution, KLF4 mRNA-containing solution, c-MYC mRNA-containing solution, LIN28A mRNA-containing solution and green fluorescent protein (GFP) mRNA-containing solution, each to a concentration of 100 ng/µL. Next, 385 µL of the OCT3/4 mRNA-containing solution, 119 µL of the SOX2 mRNA-containing solution, 156 µL of the KLF4 mRNA-containing solution, 148 µL of the c-MYC mRNA-containing solution, 83 µL of the LIN28A mRNA-containing solution and 110 µL of the GFP mRNA-containing solution were mixed to obtain an initializing factor mixture. The obtained initializing factor mixture was dispensed into 1.5 mL-volume RNase-Free tubes (Eppendorf Tube®, Eppendorf AG) at 50 µL each, and preserved in a freezer at −80° C.

(Preparation of Mononuclear Cells)

A centrifuge was set to 18° C. Blood was sampled in amounts from 5 mL to 50 mL, EDTA was added to the blood, and each mixture was gently mixed. Also, medium for human lymphocyte separation Ficoll-Paque PREMIUM, GE Healthcare, Japan) was dispensed into two 15 mL tubes at 5 mL each. After adding 5 mL of PBS to the blood for dilution, 5 mL of each was overlaid onto the human lymphocyte separation medium in the tubes. During this time, the diluted blood was slowly added onto the medium while causing it to slide on the tube wall, so as not to disturb the interface.

The solutions in the tubes were centrifuged at 400×g, 18° C. for 30 minutes. Acceleration and deceleration were carried out slowly during the procedure. After centrifugation, a white cloudy intermediate layer appeared in the tube. The white cloudy intermediate layer included mononuclear cells. The white cloudy intermediate layer in each tube was slowly collected with a Pipetman and transferred to a new 15 mL tube. The lower layer was not handled during this time. Approximately 1 mL of the white cloudy intermediate layer could be collected from each tube. The intermediate layers of two tubes were combined and transferred to a single tube.

After adding 12 mL of PBS to the collected mononuclear cells, the solution was further centrifuged at 200×g, 18° C. for 10 minutes. Next, an aspirator was used to remove the supernatant of the solution by aspiration, and 3 mL of serum-free hematopoietic cell culture medium of known composition (X-VIVO® 10, Lonza) was added, forming a suspension, thereby obtaining a mononuclear cell suspension. A 10 µL portion of the mononuclear cell suspension was stained with Trypan blue and the count was determined with a hemocytometer.

(Separation of CD34 or CD3-Positive Cells)

Reaction was performed between $1 \times 10^7$ mononuclear cells and CD34 antibody or CD3 antibody for 15 minutes in 100 µL of solution at 4° C. Following the reaction, 5 mL of MACS® buffer (Miltenyi Biotec) was added to the solution, and centrifugation was performed at 270 g. After centrifugation, the supernatant was removed and 1 mL of MACS buffer was added. Next, utilizing the separation program of an automatic magnetic cell separator (autoMACS, Miltenyi Biotec), CD34-positive cells and CD3-positive cells were separated from among the mononuclear cells.

(Culturing of Separated Cells)

After suspending $5 \times 10^6$ of the separated mononuclear cells in 1 mL of T cell culture medium or blood stem/precursor cell culture medium, they were seeded in a 12-well plate and cultured. The culturing conditions were 5% $CO_2$ concentration, 19% oxygen concentration, 37° C. temperature.

(Lipofection of Initializing Factor)

A first mixture was prepared by mixing 100 µL of low serum culture medium (Opti-MEM®, Gibco) and 25 µL of initializing factor mixture. A second mixture was also prepared by mixing 112.5 µL of low serum culture medium (Opti-MEM®, Gibco) and 12.5 µL of siRNA introducing reagent (Lipofectamine®, RNAiMAX, Thermo Fisher Scientific). Next, the first mixture and second mixture were combined and allowed to stand at room temperature for 15 minutes, to prepare a lipofection reaction mixture.

After gently adding 60 µL of the obtained lipofection reaction mixture to the 12-well plate in which the mononuclear cells were being cultured, the mononuclear cells were then cultured in a feeder-free manner at 37° C. for 18 hours. The culturing conditions were 5% $CO_2$ concentration, 19% oxygen concentration, 37° C. temperature. The mononuclear cell density upon addition of the lipofection reaction mixture was $3 \times 10^6$. After 18 hours, the mononuclear cells were collected in a 15 mL tube and centrifuged at 300 g, and the supernatant was removed. Next, 1.25 mL of CD34 blood cell culture medium was added to a 15 mL tube, the mononuclear cell suspension was returned to the same 12-well plate, and feeder-free culturing of the mononuclear cells was carried out overnight at 37 degrees. The culturing conditions were 5% $CO_2$ concentration and 19% oxygen concentration. The steps described above were repeated once every 2 days for 7 days.

(Confirmation of GFP Expression)

Figure 55:
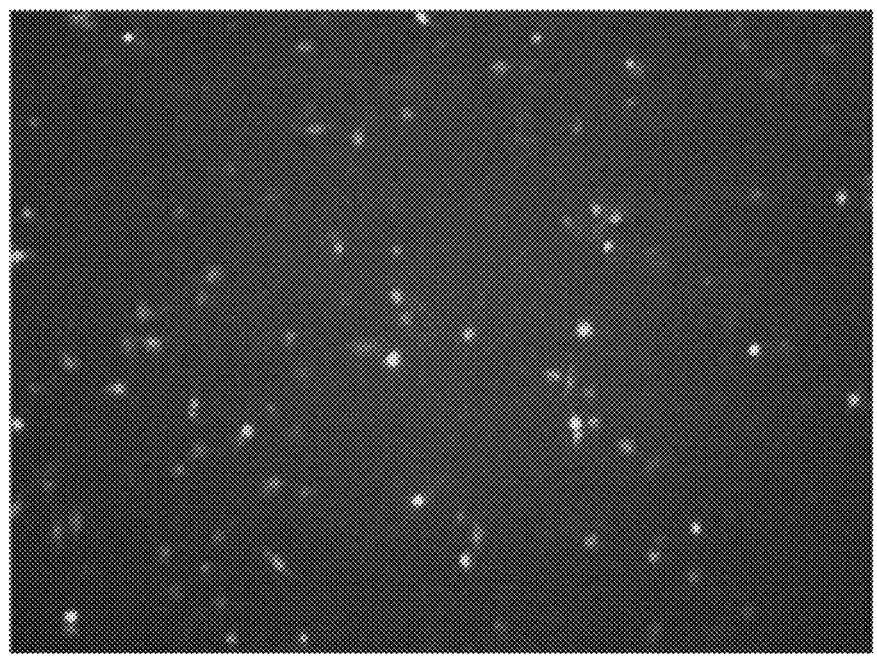
FIG. 55 is a fluorescent microscope photograph for Example 1.

On the 7th day after the start of lipofection, the density of cells after a total of 4 lipofections was $3 \times 10^6$. When a portion of the cells was removed from the 12-well plate and GFP expression was examined with a fluorescent microscope, expression of GFP was confirmed, as shown in FIG. 55. This confirmed that mRNA had been transfected in the mononuclear cells, and that protein had been synthesized from the transfected mRNA.

(Confirmation of TRA-1-60 expression)

On the 7th day after the start of lipofection, a portion of the cells were removed from the 12-well plate, and the removed cells were stained with antibody for TRA-1-60 as a surface antigen specifically expressed on the iPS cells that had begun to be initialized, the antibody being labeled with Allophycocyanin (APC) fluorescent dye. Next, the ratio of TRA-1-60-positive cells was determined with a fluorescence activated cell sorter (FACS®, BD), to confirm that reprogramming of the cells had been initiated, iPS cell genes had been expressed and iPS cells had emerged.

Figure 56:
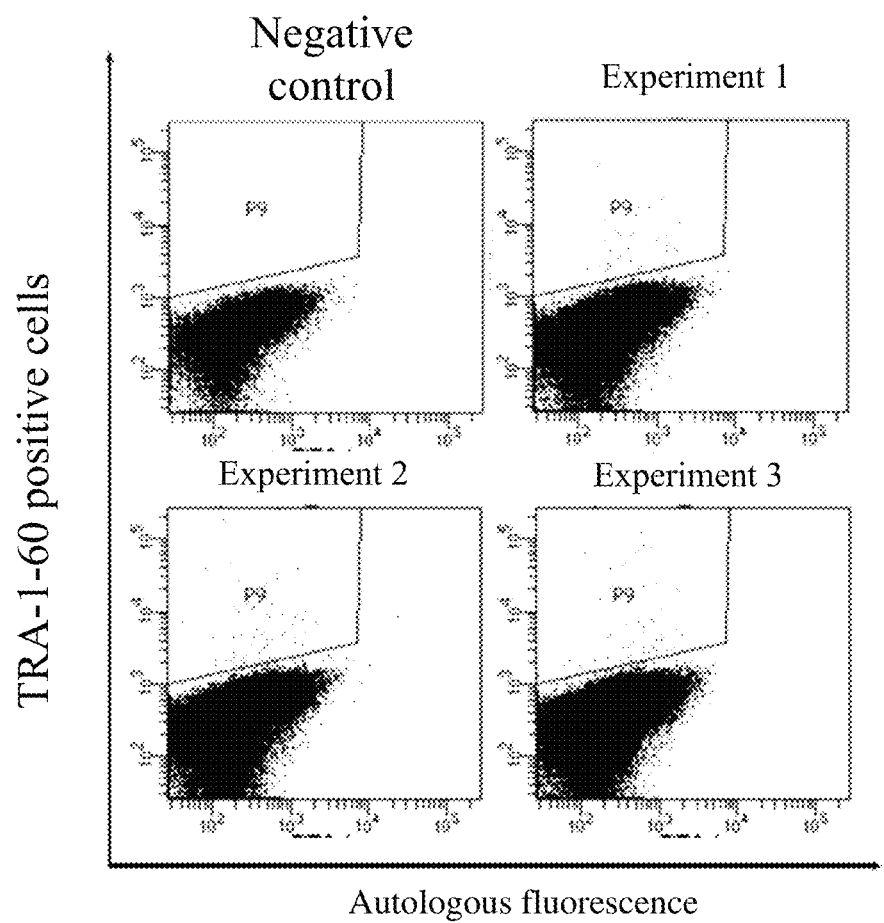
FIG. 56 is a graph showing analysis results for Example 1, using a fluorescence activated flow cytometer.

A dot plot was drawn with autologous fluorescence intensity on the x-axis and fluorescent labeled anti-TRA-1-60 antibody fluorescence intensity on the y-axis, as shown in FIG. 56. No TRA-1-60-positive cells were detected in a negative control without gene introduction. In contrast, TRA-1-60-positive cells were detected in Experiments 1, 2 and 3. Experiment 1 represents the results of induction from all of the mononuclear cells without separation by markers, Experiment 2 represents the results of induction from cells separated as CD3-positive, and Experiment 3 represents the results of induction from cells separated as CD34-positive. It was thus demonstrated that iPS cells can be induced by using lipofection of initializing factor RNA to introduce the initializing factor into blood-derived cells.

Example 2

A bFGF-containing human iPS culture medium was prepared by mixing 500 mL of Primate ES Cell Medium (ReproCELL) and 0.2 mL of bFGF (Gibco PHG0266) at a 10 μg/mL concentration.

Also, deacylated gellan gum (Nissan Chemical Industries, Ltd.) was added to the bFGF-containing human iPS culture medium to a concentration of 0.02 wt %, to prepare a bFGF-containing human iPS gel medium. In addition, 5 mL of trypsin at 2.5 wt % concentration, 5 mL of collagenase IV at 1 mg/mL concentration, 0.5 mL of $CaCl_2$ at 0.1 mol/L concentration, 10 mL of KnockOut Serum Replacement® (Invitrogen 10828-028) and 30 mL of purified water were mixed to prepare a dissociation solution, commonly known as CTK solution.

After adding 300 μL of the CTK solution to a 6-well dish (Thermoscientific 12-556-004) in which iPS cells were being cultured on feeder cells, the mixture was incubated for 3 minutes in a $CO_2$ incubator. After 3 minutes, the dish was removed from the incubator, detachment of the feeder cells alone was confirmed, and an aspirator was used to remove the CTK solution. After removing the CTK solution, 500 μL of PBS (Santa Cruz Biotech sc-362183) was added to the 6-well dish to rinse the iPS cells, and then the PBS was removed from the 6-well dish and 0.3 mL of dissociation solution (Accutase®) was added to the 6-well dish, which was placed in a $CO_2$ incubator and incubated for 5 minutes. Next, 0.7 mL of bFGF-containing iPS culture medium was added to the 6-well dish and the iPS cells were suspended until single cells were obtained.

After suspension of the iPS cells, 4 mL of bFGF-containing human iPS culture medium was added to a 15 mL centrifugation tube, and the iPS cell suspension was centrifuged at 270 g using a centrifuge. After centrifugation, the supernatant was removed, 1 mL of bFGF-containing human iPS culture medium was added to a 15 mL centrifugation tube, and a blood cell counting chamber was used to calculate the cell count. After cell counting, $5 \times 10^5$ of iPS cells each were seeded in a 15 mL Falcon Tube® (Corning 352096) or a non-adherent dish, and suspension culture was carried out without agitation.

A 2 mL portion of bFGF-containing human iPS gel medium was used in a 15 mL tube. A 2 mL portion of non-gelled bFGF-containing human iPS culture medium was used in the non-adherent dish. ROCK inhibitor (Selleck S1049) was added at 10 μmol/L to each medium. Thereafter, 500 μL of bFGF-containing human iPS gel medium was added each day to the 15 mL tube and non-adherent dish and 500 μL of bFGF-containing human iPS culture medium was added each day to the non-adherent dish. Also, ROCK inhibitor was added to the 15 mL tube and non-adherent dish each day to a final concentration of 10 μmol/L, and suspension culture was continued for 7 days.

Figure 57:
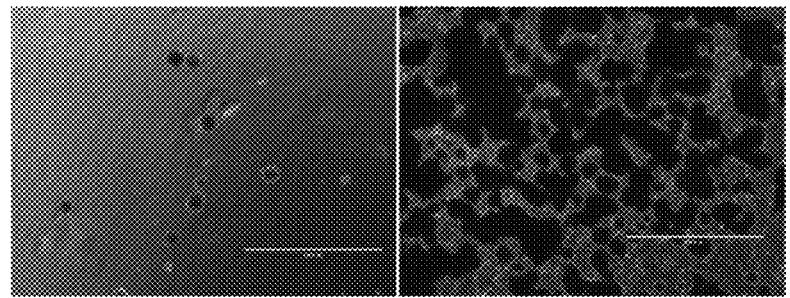
FIG. 57 is a pair of photographs of iPS cell colonies, for Example 2.
Figure 58:
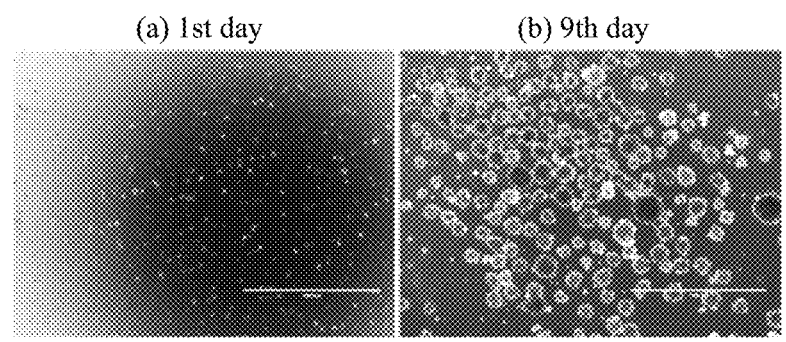
FIG. 58 is a pair of photographs of iPS cell colonies, for Example 2.

The results are shown in FIG. 57. As shown in FIG. 57(b), when iPS cells were cultured in the non-adherent dish using non-gelled bFGF-containing human iPS culture medium, notable aggregation of the iPS cell colonies was observed. In contrast, as shown in FIG. 57(a), when iPS cells were cultured using bFGF-containing human iPS gel medium in the 15 mL tube, no such conspicuous aggregation was observed. FIG. 58(a) is a photograph on the 1st day after culturing of iPS cells using bFGF-containing human iPS gel medium in the 15 mL tube, and FIG. 58(b) is a photograph on the 9th day after culturing of iPS cells using bFGF-containing human iPS gel medium in the 15 mL tube. The photographs of FIG. 58(a) and FIG. 58(b) confirmed colony formation without aggregation between iPS cells of different lines.

Figure 59:
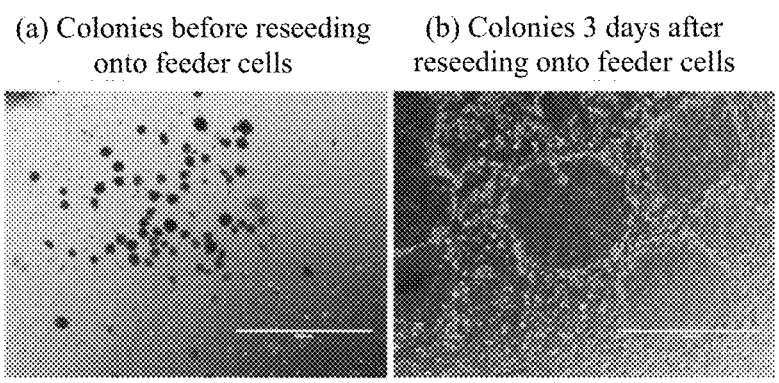
FIG. 59 is a pair of photographs of iPS cell colonies, for Example 2.
Figure 60:
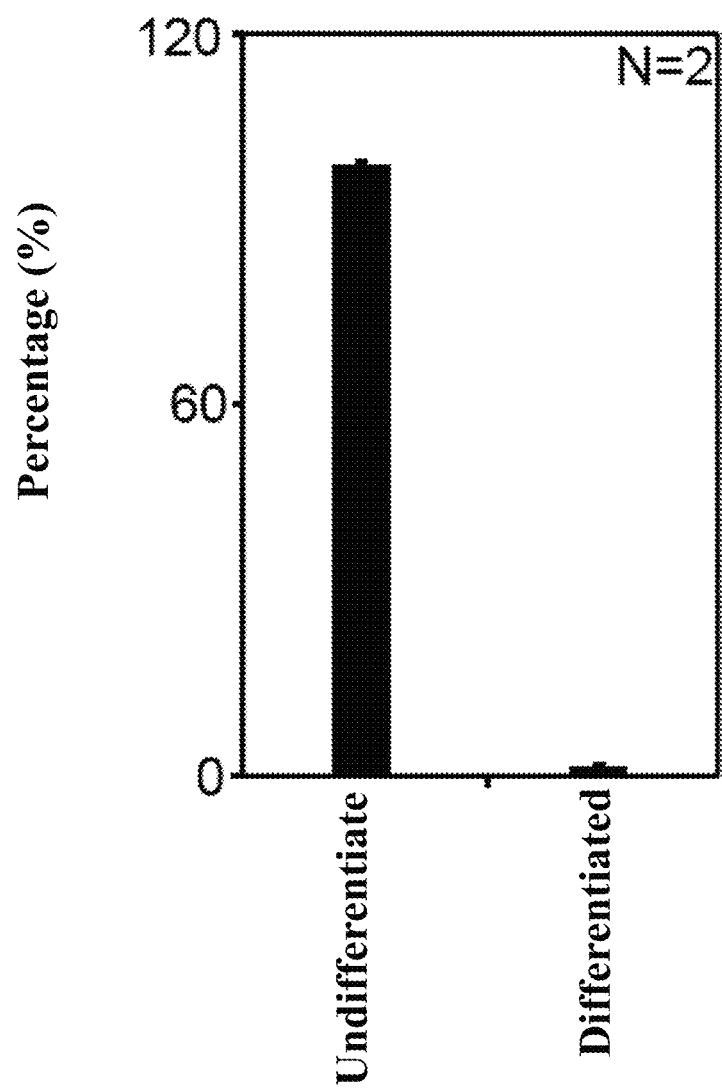
FIG. 60 is a graph showing the state of differentiation of iPS cell colonies, for Example 2.

FIG. 59(a) is a photograph immediately before reseeding of the iPS cell colonies that had been suspension cultured for 7 days in gel medium, onto feeder cells. FIG. 59(b) is a photograph taken when confirming the forms of the colonies after 3 days. As shown in FIG. 60, the results confirmed that at least 95% of the colonies were undifferentiated. It was thus demonstrated that iPS cells can be cultured in gel medium while maintaining their undifferentiated state.

Example 3

The same bFGF-containing human iPS culture medium and bFGF-containing human iPS gel medium were prepared as in Example 2. After adding 300 μL of the CTK solution to a 6-well dish in which iPS cells were being cultured on feeder cells, the mixture was incubated for 3 minutes in a $CO_2$ incubator. After 3 minutes, the dish was removed from the incubator, detachment of the feeder cells alone was confirmed, and an aspirator was used to remove the CTK solution. After removing the CTK solution, 500 μL of PBS was added to the dish to rinse the iPS cells, and then the PBS was removed from the dish and 0.3 mL of Accumax was added to the dish, after which the dish was placed in a $CO_2$ incubator and incubated for 5 minutes. Next, 0.7 mL of bFGF-containing iPS culture medium was added to the dish and the iPS cells were suspended until single cells were obtained.

After suspension of the iPS cells, 4 mL of bFGF-containing human iPS culture medium was added to a 15 mL centrifugation tube, and the iPS cell suspension was centrifuged at 270 g using a centrifuge. After centrifugation, the supernatant was removed, 1 mL of bFGF-containing human iPS culture medium was added to a 15 mL centrifugation tube, and a hemocytometer was used to calculate the cell count. The cells were counted, and then $5 \times 10^5$ iPS cells were seeded in each 15 mL tube and suspension culture was carried out without agitation.

A 2 mL portion of bFGF-containing human iPS gel medium was used in a 15 mL tube. ROCK inhibitor was added at 10 μmol/L to each medium. A 500 μL portion of bFGF-containing human iPS gel medium was added to the 15 mL tube each day thereafter. A 500 μL portion of gel medium includes 0.5 μL of ROCK inhibitor. As a control, iPS cells were also suspension cultured for 7 days under the same conditions, but without addition of a ROCK inhibitor.

Figure 61:
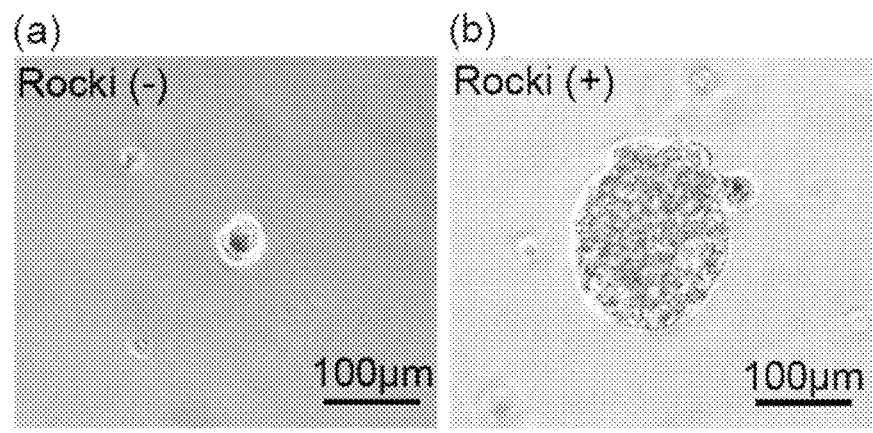
FIG. 61 is a pair of photographs of iPS cell colonies, for Example 3.

As shown in FIG. 61(a), no iPS cell colonies formed when a ROCK inhibitor was not added to the bFGF-containing human iPS culture medium. In contrast, as shown in FIG. 61(b), iPS cell colonies formed when a ROCK inhibitor was added to the bFGF-containing human iPS culture medium. These results demonstrated that a ROCK inhibitor is effective for suspension culturing of iPS cells from single cells.

Example 4

Figure 62:
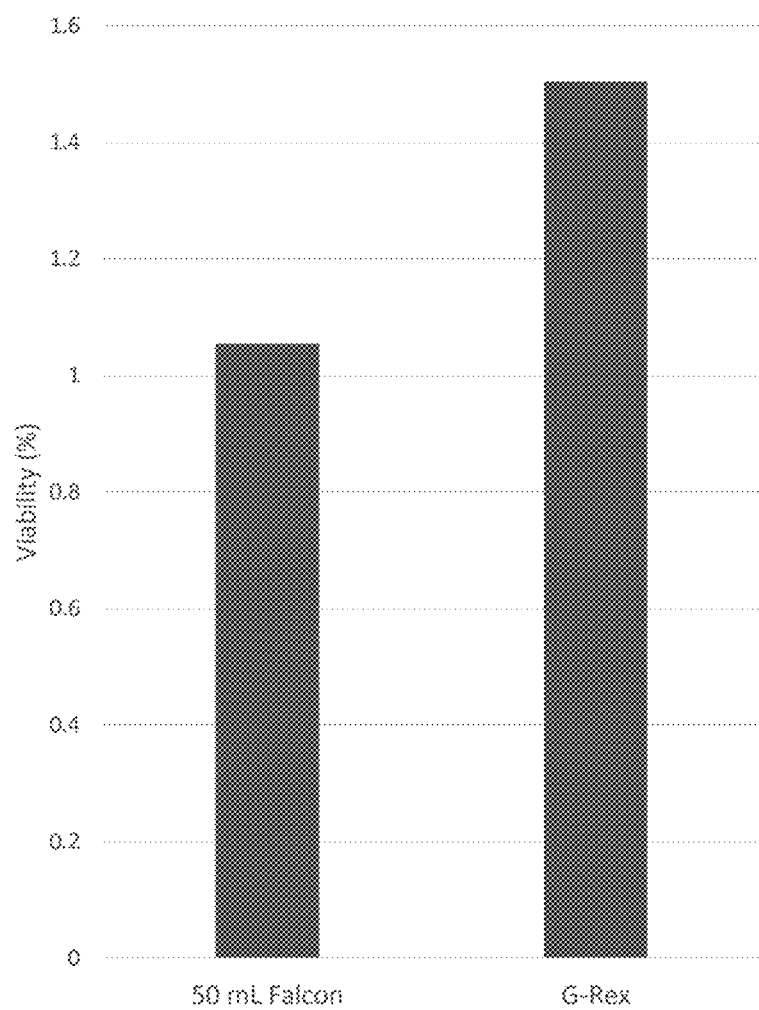
FIG. 62 is a graph showing the results for Example 4.

Using a $CO_2$-non-permeable vessel, Falcon 50 mL Conical Tube®, and a $CO_2$-permeable vessel, G-Rex® (Wilson Wolf), as dialysis tube-housing vessels, cells were suspension cultured under the same conditions, other than the vessels. As a result, culturing using the $CO_2$-permeable vessel had higher cell viability, as shown in FIG. 62.

Example 5

Gel medium containing iPS cells was added to each of two dialysis modules (Spectrum G235035) comprising a dialysis tube with a 100 kDa molecular cutoff. The dialysis modules were each placed in a 50 mL centrifugation tube, and gel medium was placed around the dialysis tubes in the centrifugation tubes. The gel medium containing the iPS cells was also directly placed in a separate 50 mL centrifugation tube.

Next, a pump was connected to one of the centrifugation tubes of the two centrifugation tubes in which dialysis tubes had been placed, as shown in FIG. 21, and the gel medium in the centrifugation tube was continuously exchanged for several days. The gel medium was stored at 4° C., and set so as to be at 37° C. when reaching the centrifugation tube. No pump was connected to the other centrifugation tube of the two centrifugation tubes in which a dialysis tube had been placed, and the gel medium in the centrifugation tube was not exchanged. The gel medium was also not exchanged in the centrifugation tube in which a dialysis tube had not been placed.

Figure 63:
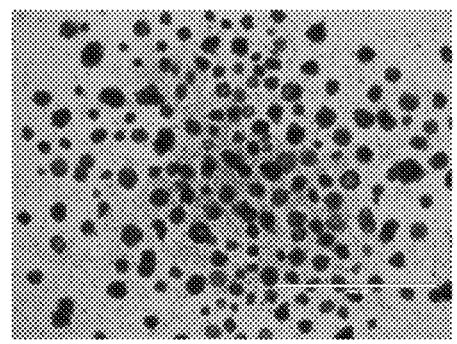
FIG. 63 is a set of photographs of iPS cell masses, for Example 5.
Figure 63:
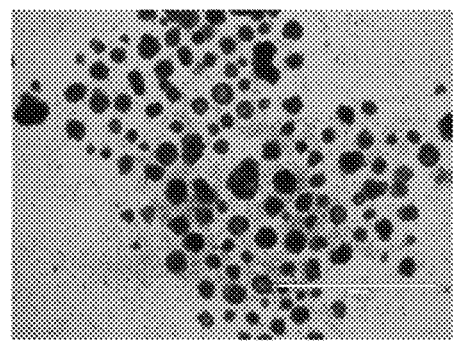
Figure 63:
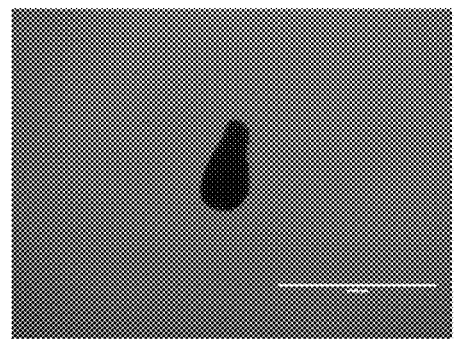
Figure 64:
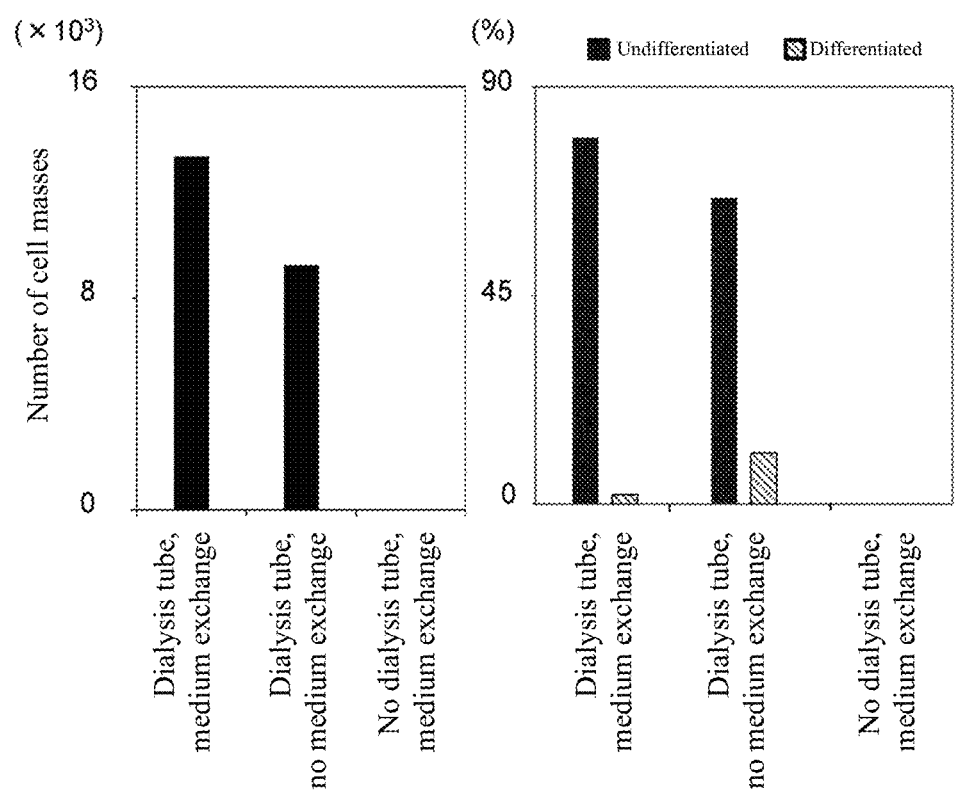
FIG. 64 is a graph showing the results for Example 5.

When the cells cultured in each vessel were observed after culturing for the same period, numerous cell masses formed when the cell masses were cultured in a dialysis tube and the gel medium surrounding the dialysis tube was continuously exchanged with a pump, as shown in FIG. 63 and FIG. 64. The number of differentiated cells was also very low. However, when the cell masses were cultured in a dialysis tube and the gel medium surrounding the dialysis tube was not continuously exchanged with a pump, the number of cell masses was low and the number of differentiated cells increased. Moreover, when the cell masses were cultured without using a dialysis tube and the gel medium was not continuously exchanged with a pump, virtually no cell masses were formed.

EXPLANATION OF SYMBOLS

2: Tube, 10: separating device, 20: preintroduction cell solution-feeding channel, 21: inducing factor solution-feeding mechanism, 30: factor introducing device, 31: introduced cell solution-feeding channel, 40: cell mass preparation device, 50: initializing culturing apparatus, 51: cell mass solution-feeding channel, 60: dissociating mechanism, 61: terminal block, 61a: recess, 61b: protrusion, 61c: large pore size section, 62: connecting block, 62a: recess, 62b: protrusion, 62c: large pore size section, 62d: small pore size section, 62e: large pore size section, 63: tip block, 63a: recess, 63b: nozzle section, 63c: large pore size section, 63d: small pore size section, 64: insertion nozzle, 65a: large pore size section, 65b: small pore size section, 66a: insertion section, 66b: insertion section, 70: amplifying culturing apparatus, 71: amplifying culturing solution-feeding channel, 72: cell mass solution-feeding channel, 75: dialysis tube, 76: vessel, 77: supply culture medium solution-feeding pump, 78: solution-feeding tube, 79: waste liquid tube, 80: dissociating mechanism, 90: cell mass transport mechanism, 91: pre-packaging cell channel, 100: packaging apparatus, 101: solution exchanger, 102: filter, 103: solution-feeding channel, 104: solution-feeding channel, 105: discharge channel, 106: discharge channel, 110: cryopreservation liquid-feeding mechanism, 171: initializing culturing photographing device, 172: telecentric lens, 173: cell observation illumination light source, 174: culture medium observation illumination light source, 201: blood storing unit, 202: blood solution-feeding channel, 203: mononuclear cell separating unit, 204: pump, 205: separating agent storing unit, 206: solution-feeding channel, 207: pump, 208: mononuclear cell solution-feeding channel, 209: pump, 210: mononuclear cell purifying filter, 211: preintroduction cell solution-feeding channel, 212: pump, 213: factor introducing device, 214: factor storing unit, 215: factor solution-feeding channel, 216: pump, 217: introduced cell solution-feeding channel, 218: pump, 219: initializing culturing vessel, 220: blood cell culture medium storing unit, 221: culture medium solution-feeding channel, 222: pump, 223: stem cell culture medium storing unit, 224: culture medium solution-feeding channel, 225: pump, 226: waste liquid solution-feeding channel, 227: pump, 228: waste liquid storage section, 229: introduced cell solution-feeding channel, 230: pump, 231: cell mass dissociater, 232: amplifying culturing vessel, 233: culture medium solution-feeding channel, 234: pump, 235: waste liquid solution-feeding channel, 236: pump, 237: introduced cell solution-feeding channel, 238: pump, 239: cell mass dissociater, 240: amplifying culturing vessel, 241: culture medium solution-feeding channel, 242: pump, 243: waste liquid solution-feeding channel, 244: pump, 245: introduced cell solution-feeding channel, 246: pump, 247: solution exchanger, 248: waste liquid solution-feeding channel, 249: pump, 250: cryopreservation liquid storing unit, 251: solution-feeding channel, 252: pump, 253: solution-feeding channel, 254: pump, 255: cryopreservation vessel, 256: low-temperature repository, 257: liquid nitrogen repository, 258: solution-feeding channel, 259: member, 260: cold storage unit, 271: sensor, 272: thermometer, 301: bag, 302: bag, 401: input device, 402: output device, 403: relationship memory unit, 501: image processor, 511: outline defining unit, 512: cell evaluating unit, 513: statistical processor, 514: density calculating unit, 515: culture medium evaluating unit, 601: enclosure, 602: intake air purification filter, 603: exhaust purification filter, 605: exhaust system, 606: exhaust purification filter, 608: injector, 613: gas discharger, 651: returning member, 652: base, 653: opening, 654: cover, 655: opening, 656: cover, 701: outer enclosure, 702: pressure adjustment hole, 703: occluding member, 800: shielding member, 801: enclosure side shielding member, 802: exhaust system side shielding member, 811: guide, 812: guide, 900: cell culture device, 1201: blood storing unit,

1202: blood solution-feeding channel, 1203: mononuclear cell separating unit, 1204: driving unit, 1205: separating agent storing unit, 1206: separating agent solution-feeding channel, 1207: driving unit, 1208: mononuclear cell solution-feeding channel, 1210: mononuclear cell purifying filter, 1211: preintroduction cell solution-feeding channel, 1212: driving unit, 1213: factor introducing device, 1214: factor storing unit, 1215: factor solution-feeding channel, 1216: driving unit, 1217: introduced cell solution-feeding channel, 1218: driving unit, 1219: initializing culturing vessel, 1220: blood cell culture medium storing unit, 1221: culture medium solution-feeding channel, 1222: driving unit, 1223: stem cell culture medium storing unit, 1224: culture medium solution-feeding channel, 1226: waste liquid solution-feeding channel, 1228: waste liquid storage section, 1229: introduced cell solution-feeding channel, 1230: driving unit, 1231: cell mass dissociater, 1232: amplifying culturing vessel, 1235: waste liquid solution-feeding channel, 1245: introduced cell solution-feeding channel, 1246: driving unit, 1247: solution exchanger, 1248: waste liquid solution-feeding channel, 1250: cryopreservation liquid storing unit, 1251: cryopreservation liquid-feeding channel, 1252: driving unit, 1253: freezing cell solution-feeding channel, 1253: solution-feeding channel, 1254: driving unit, 1255: cryopreservation vessel, 2000: embedding member, 2001: mononuclear cell channel, 2002: mononuclear cell storage unit, 2003: non-mononuclear cell component channel, 2004: non-mononuclear cell component storage unit, 2204: slave unit, 2228: waste liquid storage section, 2229: introduced cell solution-feeding channel, 2231: cell mass dissociater, 3228: waste liquid storage section, 4228: waste liquid storage section, 5228: waste liquid storage section

The invention claimed is:

1. A method for processing cells, comprising:
   providing a cell processing apparatus comprising:
   a first vessel,
   a housing that embeds the first vessel such that the first vessel is entirely disposed inside the housing,
   a stem cell culture medium storage, which is disposed outside the housing and stores stem cell culture medium,
   a waste liquid storage, which is disposed outside the housing and is configured to store waste liquid,
   a culture medium solution-feeding channel connecting the first vessel and the stem cell culture medium storage, and
   a waste liquid solution-feeding channel connecting the first vessel and the waste liquid storage;
   culturing, in the first vessel, inducing factor-introduced cells into which an inducing factor has been introduced;
   transferring the stem cell culture medium from the stem cell culture medium storage to the first vessel by the culture medium solution-feeding channel; and
   transferring waste liquid from the first vessel to the waste liquid storage by the waste liquid solution-feeding channel.

2. The method according to claim 1,
   wherein the cell processing apparatus further comprises a second vessel, which communicates with the first vessel and is disposed inside the housing such that the housing also embeds the second vessel, and
   wherein the method further comprises transferring the inducing factor-introduced cells from the first vessel to the second vessel and amplifying culturing, in the second vessel, the inducing factor-introduced cells.

3. The method according to claim 1,
   wherein the cell processing apparatus further comprises
   a third vessel, which communicates with the first vessel and is disposed inside the housing such that the housing also embeds the third vessel,
   a factor storage, which is disposed outside the housing and stores the inducing factor, and
   a factor solution-feeding channel connecting the third vessel and the factor storage, and
   wherein the method further comprises transferring the inducing factor from the factor storage to the third vessel by the factor solution-feeding channel, and introducing the inducing factor into cells to prepare the inducing factor-introduced cells in the third vessel.

4. The method according to claim 1, wherein the housing is molded around the first vessel.

\* \* \* \* \*